(12) United States Patent
Felden

(10) Patent No.: US 7,794,944 B2
(45) Date of Patent: Sep. 14, 2010

(54) EUBACTERIAL TMRNA SEQUENCES AND USES THEREOF

(75) Inventor: Brice Felden, Le Lou du Lac (FR)

(73) Assignee: University of Utah Research Foundation, Salt Lake City, UT (US)

(*) Notice: Subject to any disclaimer, the term of this patent is extended or adjusted under 35 U.S.C. 154(b) by 228 days.

(21) Appl. No.: 12/163,564

(22) Filed: Jun. 27, 2008

(65) Prior Publication Data

US 2009/0104608 A1   Apr. 23, 2009

Related U.S. Application Data

(62) Division of application No. 11/329,230, filed on Jan. 11, 2006, now Pat. No. 7,611,843, which is a division of application No. 09/958,206, filed as application No. PCT/US00/08988 on Apr. 6, 2000, now Pat. No. 7,115,366.

(60) Provisional application No. 60/128,058, filed on Apr. 7, 1999.

(51) Int. Cl.
*C12Q 1/68* (2006.01)
*A01N 43/04* (2006.01)
*A61K 31/70* (2006.01)
*C07H 21/02* (2006.01)
*C07H 21/04* (2006.01)
*C12P 19/34* (2006.01)

(52) U.S. Cl. .................. 435/6; 435/91.1; 435/91.2; 514/44 R; 536/23.1; 536/23.7

(58) Field of Classification Search .................. None
See application file for complete search history.

(56) References Cited

OTHER PUBLICATIONS

B. Felden et al., "Eubacterial tmRNAs: everywhere except the alpha-Proteobacteria?" Biochimica et Biophysics Acta 1446:145-148, 1999.
N. Nameki et al., "Three of four pseudoknots in tmRNA are interchangeable and are substitutable with single-stranded RNAs," FEBS Lett 470(3):345-349, Mar. 31, 2000.
N. Nameki et al., "Functional and structural analysis of a pseudoknot upstream of the tag-encoded sequence in *E. coli* tmRNA," J. Mol. Biol 286(3):733-744, Feb. 26, 1999.
W. Schönhuber et al., "Utilization of tmRNA squences for bacterial identification," MBC Microbiology 2001, 1:20 (online, 8 pages).
K.P. Williams et al., "Phylogenetic analysis of tmRNA secondary structure," RNA 2:1306-1310, 1996.
C. Zwieb et al., "Survey and Summary, Comparative sequence analysis of tmRNA," Nucleic Acids Research 27(10):2063-2071, 1999.

*Primary Examiner*—Janet Epps-Smith
(74) *Attorney, Agent, or Firm*—Rothwell, Figg, Ernst & Manbeck pc

(57) ABSTRACT

The present invention is directed to eubacterial tmDNA sequences and the corresponding tmRNA sequences. The present invention is further directed to alignments of eubacterial tmDNA sequences and the use of the sequences and sequence alignments for the development of antibacterial drugs. The present invention is also directed to the use of the sequences for the development of diagnostic assays.

6 Claims, 24 Drawing Sheets

```
                    ┌─CODING SEQUENCE                                    H4
Tab.saccha  AUAAACgcaaacgauaau--------------uuagcuuacgcugcuUAAUUA-CAAGCAGC---
C.acetobut  ***************---------------********************----------
C.stercora  AUAAACgcaaacaacgauaacuac---------gcuuuagcugcugcgUAAGUAACACGCAGCC--
C.perfrige  AUAAACgcagaagauaau---------------uuugcauuagcagcuUAAUUUAGCGCUGCU---
C.lentocel  GUAAACgcugaagauaau---------------uuagcaaucgcugcUAAUUA-AGGC-GC----
Hlb.mobili  UUAAUUgccgaagauaac---------------uacgcuuuagcugcuUUAUUGCAGUCUAA----
Hsp.gestii  UUAAUUgccgaagauaac---------------uacgcuuuagcugcuUUAUUGCAGUCUAA----
Bb.brevis   UUAACUggcaacaaacaa---------------cuuucucucgcugcuUAAUAACCAGUGAG----
B.subtilis  AUAACUggcaaaacuaacaguuuuaaccaaaacguagcauuagcugccUAAUAAGCGCAGCGA---
B.badius    AUAACUggcaaaaagau----------------uuagcuuuagcugccUAAUAUAGGUUCAGCU--
B.megateri  AUAACUggcaaaucuaacaauaac---------uucgcuuuagcugcaUAAAGUAGCUUAGC---
B.thermole  AUAACUggcaaacaaaac---------------uacgcuuuagcugccUAAUUGCUGCAGCUA---
Eco.fecium  AUAACUgcuaaaaacgaaaacaacucu------uacgcuuuagcugccUAAAAA-CAGUUAGCGUA
Eco.faecal  AUAACUgcuaaaaacgaaaacaauucu------uucgcuuuagcugccUAAAAACCAGCUAGCGAA
Stc.pyogen  AUAACUgcaaaaaauacaaacucu---------uacgcuuuagcugccUAAAAACCAGCUAGCGU-
Stc.pneumo  AUAACUgcaaaaaauaacacuucu---------uacgcucuagcugccUAAAAACCAGCAGGCGU-
Stc.gordon  AUAACUgcaaaaaauaauacuucu---------uacgcuuuagcugccUAAAAACCAGCGGGCGU-
Stc.mutans  AUAACUgcaaaaaauacaaauucu---------uacgcaguagcugccUAAAAACCAGCCUGUGU-
Stp.epider  AUAACUgacaaaucaaacaauaau---------uucgcaguagcugcgUAAUAGCCACUGC-----
Stp.aureus  AUAACUggcaaaucaaacaauaau---------uucgcaguagcugccUAAUCGCA-CU-CUGC--
L.acidophi  AUAACUgcaaauaacaaaaauucu---------uacgcauuagcugcuUAAUUUAGCGCAUGCGU- Tab.saccha  CGUUCAA-CCUU-UGAU-UCCCAC--AUCA-AAGGAUUGGGCGUCG--AUUUAGUGGGG
C.acetobut  ********-******--*AAUCUGGCGUCG----AGAGCGGGG
C.stercora  CGUCGG-C-CCCGGGGUUCCUGC---GCCUCGGGAUACCGGCGUCA---UCAAGGCAGG
C.perfrige  CAUCCUU---CCU-CAAUUGCCCACG-GUUG-AGAGUAAGGGUGUCAUUUAAAAGUGGGG
C.lentocel  AGUCCU----CCU-AGGUCUUCCGCA-GCCU-AGAUC-AGGGCUUCG---ACUCGCGGAU
Hlb.mobili  CCUCUU-C-UCC-UC-UGUGCUCUCGGUGA-GGAUGUAAGGGGUCA-UUUAAGAGAGCU
Hsp.gestii  CCUCUU-C-UCC-UC-UGUGCUCUCGGUGA-GGAUGUAAGGGGUCA-UUUAAGAGAGCU
Bb.brevis   GCUCUC-CCACU-GCAUCGGCCCGU-GUGC-CGUGGAUAGGGCUCAACUUUAACGGGCU
B.subtilis  GCUCUUC--CUG-ACAU-UGCCAUU-GUGU-CUGU-GAAGAGCACA-UCCAAGUAGGCU
B.badius    GCUCCU--CCCG-CUAU-CGUCCAU-GUAGUCGGGUAAGGGUCCAAACUUAGUGGACU
B.megateri  GUUCCU--CCCU-CCAU-CGCCCAU-GUGGUAGGGUAAGGGACUCACUUUAAGUGGGCU
B.thermole  GCUCCUC--CCG-CCAU-CGCCCGC-GUGG-CGUUCGAGGGGCUCAUAUGGAGCGGGCU
Eco.fecium  GAUCCU--CUCG-GCAU-CGCCCAU-GUGCUCGAGUAAGGGUCUCAAAUUUAGUGGGAU
Eco.faecal  GAUCCU--CCCG-GCAU-CGCCCAU-GUGCUCGGGUCAGGGUCCUAAUCGAAGUGGGAU
Stc.pyogen  GACUUCU--ACA-AGAU-UGCUUGU-GUCC-UGUU-AGAAGUC-UCAAAAUAGCAAGCU
Stc.pneumo  GACCC--GAUUU-GGAU-UGCUCGU-GUUC-AAUGA-CAGGUCUUAUUAUUAGCGAGAU
Stc.gordon  GACCC--GAUUC-GGAU-UGCUUGU-GUCU-GAUGA-CAGGUCUUAUUAUUAGCAAGCU
Stc.mutans  GAUCAAU--AAC-AAAU-UGCUUGU-GUUU-GUUG-AUUGGUCUUAUUGUUAACAAGCU
Stp.epider  AUCGCC-UAACA-GCAU-CUCCAC-GUGC-UGUUAACGCGAUUCAACCCUAGUAGGAU
Stp.aureus  AUCGCC-UAACA-GCAU-UUCCAU-GUGC-UGUUAACGCGAUUCAACCUUAAUAGGAU
L.acidophi  UGCUCU-UUGUC-GGUU-UACUCGU-GGCU-GACAC-UGAGUAUCA-ACUUAGCGAGUU
                                                    PK2
```

FIG. 3B

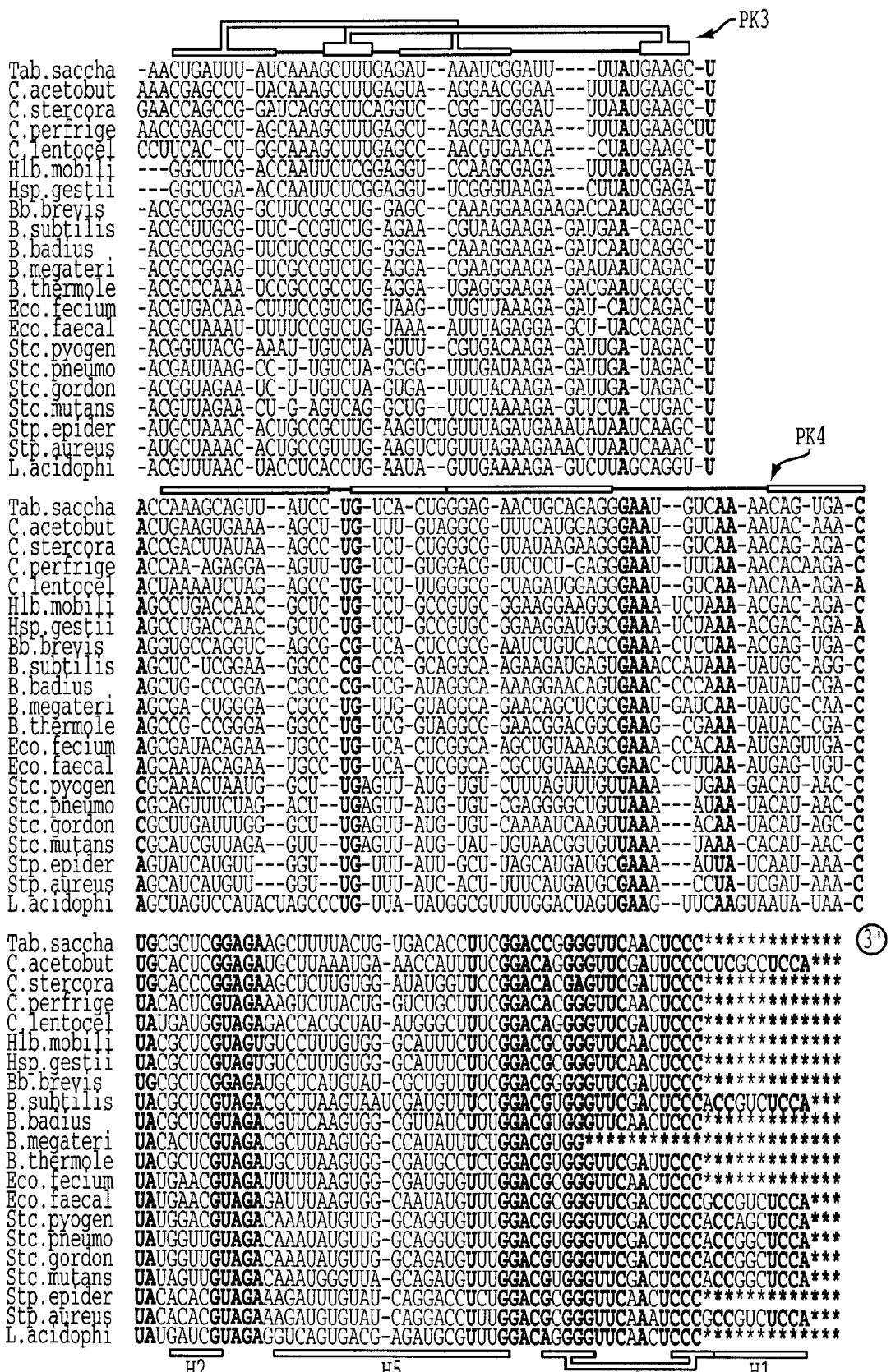
FIG. 3C  +RNA-LIKE DOMAIN H1-H6

```
Aqf.aeolic  CG-GGCUACUCGGU--CGCACGGG-GCUGAGUAGCUGACACCUAACCCGUGCU  ⎫
Tt.maritim  A--CCGAUUCAG--UUCGCCUUCCGGCCUGAAUCGGGAAAACUCAGGAAGGCU  ⎪
Tt.neapoli  A--CCGAUCUGGGCUCCGCCUUCCGGCCCGGAUCGGGAAGGUUCAGGAAGGCU  ⎪
T.thermoph  A--GCCCGGGGC--CACGCCCUCU--AACCCCGGGCGAAGCUUGAAGGGGGCU  ⎪
D.radiodur  A--GCCC-AGGC--GAUUCUCCAU--AGCCGACGGCGAAACU-UUAUGGAGCU  ⎪
D.proteoly  A--GCUU-AGGU--GAGGUUCCAU--AGCCAAAAGUGAAACC-AAAUGGAAAU  ⎬ PK3
Tmc.roseum  GCCCCUGGCCCA--AGCGCCGGUG---CGGGCCAGGUCAAGCGUGAUCCGGCU  ⎪
Ctb.proteo  GC-UCUUAAGCAG--UGGCACCAG--CUGUUUAAGGGUGAAAAGAGUGGUGCU  ⎪
Her.aurant  CGCUCCCCUAGUU--AUGUCUGUG--GGCUAGGGG--CUAAGAUUAACAGGCU  ⎪
Tdb.commun  UU-GGGAGGCUUAA-UCGGUGGGG-UUAAGCCUCCCGAGAUUACAUCCCACCU  ⎪
Ver.spinos  G--GCCAAAAGAGC-GGGCGACCG-GC-CCCAAGGCGAGAUCUACAGGCCGCU  ⎪
Dcg.thermo  GCCCCUUCCG-----ACUCCCCUA-----AGGAAGGGAAAGA-UGUAGGGGAU  ⎭
            ══════════════════════════════════════════════════════

Aqf.aeolic  A--CCCUC-GGGGAGCUUGCCCGUGGGCGACCC-GAGGG--GAAAUCC-UGAACACGGGC  ⎫
Tt.maritim  G-UGGGAGAGGACACCCUGCCCGUGGGAGGUCC-CUCCC--GAGAGCG-AAAACACGGGC  ⎪
Tt.neapoli  G-UGGGAAGCGACACCCUGCCCGUGGGGGGUC-CUUCCC--GAGACAC-GAAACACGGGC  ⎪
T.thermoph  C-GCUCCUGGCC--GCCCGUCCGCGGGCCAAGCCAGGAG--GACACGC-GAAACGCGGAC  ⎪
D.radiodur  A-CGGCCUGCGAGAACCUGCCCACUGGUGAGCGCCGGCCC-GACAAUC-AAACAGUGGGA  ⎪
D.proteoly  A-AGGCGGACGGCAGCCUGUUUGCUGGCAGCCCAGGCCC--GACAAUU-UAAGAGCAGAC  ⎬ PK4
Tmc.roseum  C-GGCUGACCGGGAUCCUGUCGGUGGGAGCCUGG-CAGC--GACAGUA--GAACACCGAC  ⎪
Ctb.proteo  G--GGCAGUGCGGUU-GGGCU-UCCUGGGCUGCACUGUC--GACUU-CACAGGAGGGC  ⎪
Her.aurant  G-GUCGUGGC-CCGCUUUGUCUAUCGGGUGGUGCACCGAU-AAGAUUU-AAUCAAUAGAC  ⎪
Tdb.commun  G--GUAGGGUUGCUUGGUGCCUGUGACAAGCA-CCCUAC--GAGAUUU--UCCCACAGGC  ⎪
Ver.spinos  G--GAUGGACGGCAUCCUGGCAGUAGGAGGCUGGACAUC--GAGAUCA--AAUNAUUGCC  ⎪
Dcg.thermo  AGGUGCUUACAGAAUCCUGCGGGAGGGAGUCUGUAAGUGCCGAAAAGUUAAAACUCCCGC  ⎭
            ════════════════════════════════════════════════════════════

Aqf.aeolic  UAAGCC-UGUAGAGCCUCGGAUGUGGCCGCCGUCCUCGGACGCGGGUUCGAUUCCCGCCGCCUCCACCA
Tt.maritim  UGCGCU-CGGAGAAGCCCAGGGG---CCUCCAUCUUCGGACGGGGGUUCGAAUCCCCCGCCUCCACCA
Tt.neapoli  UGCGCU-CGGAGAAGCCCAGGGG---CCUCCAUCUUCGGACGGGGGUUCGAUUCCCGCCGCCUCCA***
T.thermoph  UACGCG-CGUAGAGGCcacgccc----cggcgaccuucggacgggggguucgauuccccccaccuccacca
D.radiodur  UACACA-CGUAGACGCA-CGCUG---GACGGACCUUUGGACGGCGGGUUCGACUCCGCCACCUCCACCA
D.proteoly  UACGCA-CGUAGAUGCA-CGCUG---GAUGGACCUUUGGACGGCGGGUUCGAUUCCCGCCGCCU-CACCA
Tmc.roseum  UAAGCC-UGUAGCAUAUCCUCGG---CUGAACGCUCUGGACGGGGGUUCAACUCCCGCCAGCUCCACCA
Ctb.proteo  UAAGCC-UGUAGACGCGAAAGGU---GGCGGCUCGUCGGACGCGGGUUCGAUUCCCGCCGCCUCCACCA
Her.aurant  UACGCU-UGUAGAUGCUUGCGGU----UUAACUUUUGGACGCGGGUUCGAUUCCCGCCGCCUCCACCA
Tdb.commun  UAAGCC-UGUAGCGGUUUAAUCU---GAACUAUCUCCGGACGCGGGUUCGAUUCCCGCCGCCUCCACCA
Ver.spinos  UGAGCA-UGGAGACGCUUUCAUA-----AAGGNGUUCGGACAGGG******************
Dcg.thermo  UAAGCU-UGUAGAGGCUUUUGAU---UCUUGCUCUCUGGACGCGGGUUCGAUUCCCGCCGCCUCCACCA ③'
            ═════════  ═════════         ═════════ ══════
               H2         H5                H6      H1
                                              H6
                                    +RNA-LIKE DOMAIN H1-H6
```

FIG. 4B

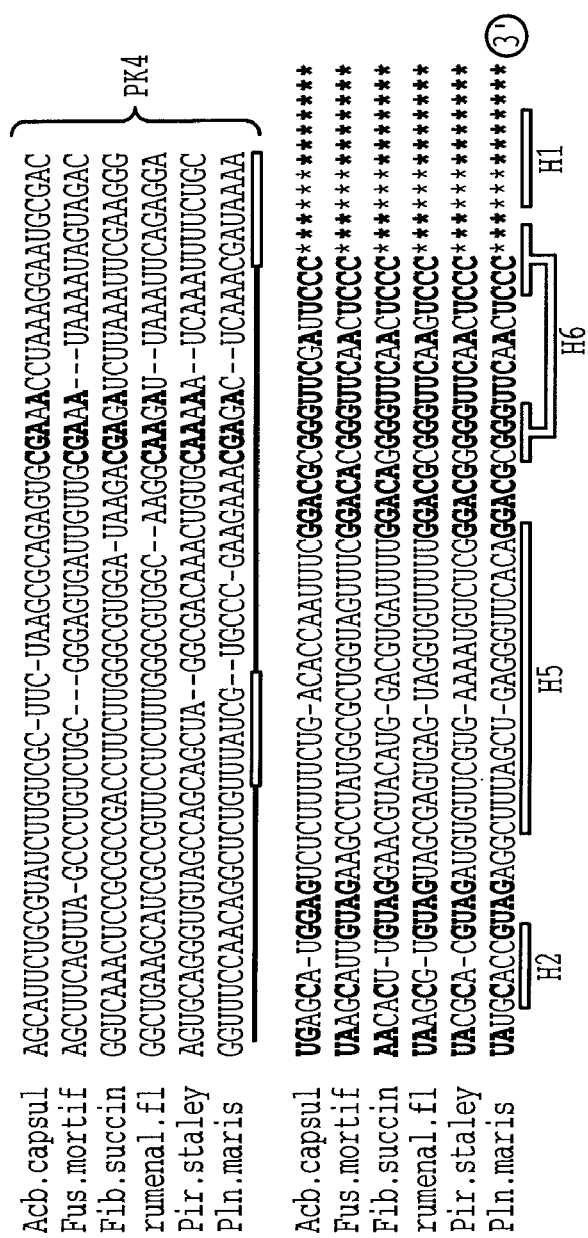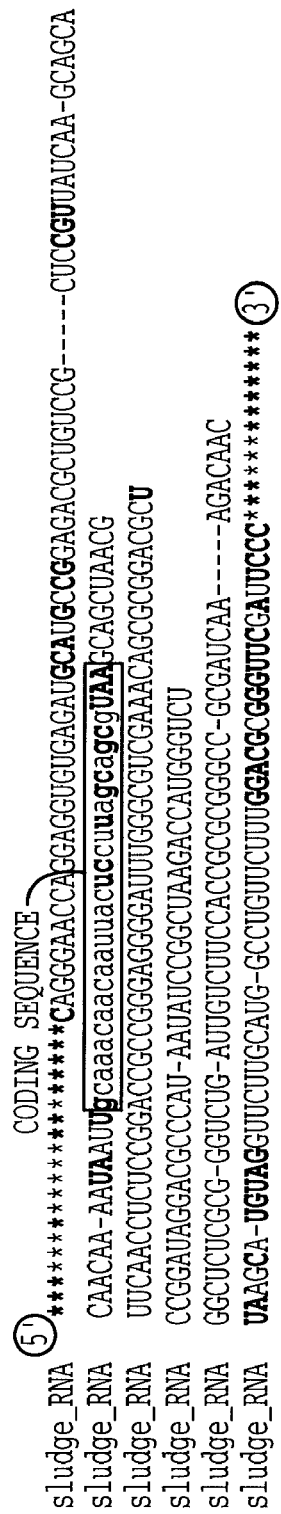
FIG. 7A-2
FIG. 7B

```
Alc.faecal  GCAGUGUUAU-UUACAAAGAAU---C-GAAUCGGUCUGCGCCACGAAGUCCGGUUCUAAAA-CUUAGUGGAU
Alc.eutrop  GCGAGGUCAU-UUACGUCAGAU---A-AGCUCCGGAAGGGUCACGAAGCCGGGGACGAAAA-CCUAGUGACU
Ral.picket  GCGAGGUCAU-UUACGUCAGAU---A-AGCUUUAGGUGAGUCACGGGCCUAGAGACGAAAA-CUUAGUGAAU
Nis.gonorr  GCAACGUCAUCUUACAUUGACU---G-GUUUCCAGCCGGGUUACUUGGCAGGAAAUAAGACUUAAGGUAACU
Nis.meninS  GCAACGUCAUCUUACAUUGACU---G-GUUUCCUGCCGGGUUAUUUGGCAGGAAAUGAGAUUUAAGGUAACU
Chb.violac  GUAGUGUCACUCUACAUCUGCU---A-GUGCUGUUCCGGGUUACUUGGUUCAGUGCGAAAUAAUAGGUAACU    }
Nms.cryoto  GCAGAGUCAU-UAG-CAAGGAU---C-GCGUUCUGUAGGGUCACUUUACAGAACGUUAAACAAUAGGUGACU    } PK3
Mtb.glycog  GCAGCGUCAU-UAAGAGAGGAU---C-GUGCGAUAUUGGGUUACUUAAUAUCGUAUUAAAUCCAAGGUAACU
Ps.testost  GCAAGGGAAU-UUUCAUUAGCU---G-GCUGGAUACCGGGCUUCUUGGUAUUUGGCGAGAUUUUAGGAAGCU
Vx.paradox  GCAAGGAUAA-CUACAUGGGCU---G-GCUCCGAUCCGGGUACCUUGGGUCGGGGCGAGAAAAUAGGGUACU
Hph.paller  GCAAGGUAAU-UUACAUCGGCU---G-GUUCUGCGUCGGGCACCUUGGCGCAGGAUGAGAUUCAAGGAUGCU
Brd.pertus  GCAGCGACAU-UCACAAGGAAU---CGGCCACCGCUGGGGUCACA-CGGCGUUGGUUUAAA-UUACGUGAAU
                PK2
Alc.faecal  CGCCAAGG-AAAGGCCUGUCA-AUUGGCAUAGUCCAAGGUUAAAACUUAAAAUUAAU-UGAC
Alc.eutrop  CGCCGUCG-UAGAGCGUGUUC-GUCCGCGAUG-CGCCGGUUAAAU---CAAA-UGACAGAAC
Ral.picket  CGCCGUCG-UAGAGCGUGUUC-GUCCGCGAUG-CGGCGGUUAAAU---CAAA-UGACAGAAC
Nis.gonorr  GGUUUCCA-AAAGGCCUGUUG-GUCGGCAUGA-UGGAAAUAAGAUUUUCAAAUAGACACAAC
Nis.meninS  GGUUUCCA-AAAGGCCUGUUG-GUCGGCAUGA-UGGAAAUAAGAUUUUCAAAUAGACACAAC
Chb.violac  CGCCAAAGUCCA-GCCUGUCC-GUCGGCGUGG-CAGAGGUUAAAUC--CAAA-UGACACGAC    }
Nms.cryoto  CGCCUGCC-AUCAGCCCGCCA-GCUGGCGGUU-GUCAGGUUAAAU---UAAA-GAGCAUGGC    } PK4
Mtb.glycog  CGCCUGCU-GUUUGCUUGCUC-GUUGGUGAGC-AUCAGGUUAAAU---CAAA-CAACACAGC
Ps.testost  GGCUACCCAAGCAGCGUGUGC-CUGCGGGGUUUGGGUGGCGAGAUU--UAAA-ACAGAGCAC
Vx.paradox  GGCGUCCGGUUUAGCGUGUGA-CUGCGCGACUCCGGAAGCGAGACU--CAAA-ACAGAUCAC
Hph.paller  GGCUUCCCGUUUAGCGUGCCA-CUGCGCGACUCGGGCGGCGAGACC--CAAA-UCAGACGGC
Brd.pertus  CGCCCUGG-UCCGGCCCGUCG-AUCGGCUAAGUCCAGGGUUAAAUC--CAAAUAGAU-CGAC Alc.faecal  UACACAUGUAGAACUGUCUGUGGACGGCUUGCGGACGGGGGUUCGAUUCCC************
Alc.eutrop  UAAGUAUGUAGAACUCUCGUGGAGGGCUUACGGACGCGGGUUCGAUUCCCGCCGGCUCCACCA
Ral.picket  UAAGUAUGUAGAACUCUCGUGGAGGGCUUGCGGACGCGGGUUCGAUUCCC************
Nis.gonorr  UAAGUAUGUAGAACGCUUUGUAGAGGACUUUCGGACGGGGGUUCGAUUCCCCCCGCCUCCACCA
Nis.meninS  UAAGUAUGUAGAACGCUUUGUAGAGGACUUUCGGACGGGGGUUCGAUUCCCCCCGCCUCCACCA
Chb.violac  UAAGUAUGUAGAACUCACUGUAGAGGACUUUCGGACGCGGGUUCAACUCCC************
Nms.cryoto  UAAGUAUGUAGAACUGUCUGUAGGAGGACUUGCGGACGCGGGUUCAACUCCC************
Mtb.glycog  UAAGUAUGUAGAACUGUCUGUGGAGGGCUUGCGGACGGGGGUUCGAUUCCC************
Ps.testost  UAAACAUGUAGAUCUGUCCGGCGAAGGCUUACGGACGCGGGUUCAAUUCCCGCCGGCUCCA***
Vx.paradox  UAAACAUGUAGAACUGCGCGAUGAAGGCUUGCGGACGGGGGUUCAACUCCC************
Hph.paller  UACACAUGUAGAACUGCUCGAAAAAGGCUUGCGGACGGGGGUUCAACUCCC************
Brd.pertus  UAAGCAUGUAGAACUGGUUGCGGAGGGCUUGCGGACGGGGGUUCAAUUCCCCCCGGCUCCACCA  (3')
               H2          H5              H6       H1
```

FIG. 9B

```
                     H1              H5            H2
        5'           ══              ══════════    ═══
Leg.pneumo  *******************CGUGGGUUGCAAAACCGGAAGUGCAUGC
Chr.vinosu  *******************CGUGGGUCGCGAAACCUAAGGUGCAUGC
Dcb.nodosu  ***************************CUCGAGGUGCAUGU
Ps.aerugin  GGGGCCGAUU-AGGAUUCGACGCCGGUAACAAAACUUGAGGGGCAUGC
Ps.fluores  *******************CGCCGGUUGCGAACCUUUAGGUGCAUGC
Mar.hydroc  *******************CGCCGGUGACGAACCCUUGGGUGCAUGC
Shw.putref  GGGGGCGAUUCUGGAUUCGACAGGAUUCACGAAACCCUGGGAGCAUGC
Psm.halopl  *******************CGGAAUUCAAGAAGCCCGAGGUGCAUGU
Ae.salmoni  *******************CAAGAUUCACGAAACCCAAGGUGCAUGC
S.typhimur  GGGGCUGAUUCUGGAUUCGACGGGAUUUGCGAAACCCAAGGUGCAUGC
E.coli      GGGGCUGAUUCUGGAUUCGACGGGAUUUGCGAAACCCAAGGUGCAUGC
Yer.pestis  GGGGCUGAUUCUGGAUUCGACGGGAUUCGCGAAACCCAAGGUGCAUGC
V.cholerae  GGGGCUGAUUCAGGAUUCGACGGGAAUUUUGCAGUCUGAGGUGCAUGC
H.influenz  GGGGCUGAUUCUGGAUUCGACGGGAUUAGCGAAGCCCAAGGUGCACGU
H.actinomy  GGGGCUGAUUCUGGAUUCGACGGGAUUAGCGAAGCCCGAAGUGCACGU
                              PK1
                    ════════════════════════════
Leg.pneumo  CGAG-AAGGAGAUC-UCUCGUAAAUA-AGA-CUCAAUUA-AAU
Chr.vinosu  CGAG-GUGCGGUUGACCUCGUAAAAC--CCUCCGCAAA--CUU
Dcb.nodosu  CGAG-AAUGAGAGAAUCUCGUUAAAU--ACUUUCAAAA--CUU
Ps.aerugin  CGAGCUGGUAGCAGAACUCGUAAAUUCGCUGCUGCAAA--CUU
Ps.fluores  CGAGUUGGUAACAGAACUCGUAAAUCCACUGUUGCAACUUUCU
Mar.hydroc  CGAGAUGGCAGCGAAUCUCGUAAAUCCAAAGCUGCAAC--GUA
Shw.putref  CGAG-GGGCGGUUGGCCUCGUAAA----AAGCCGCAAA--GUU
Psm.halopl  CGAG-GUGCGGUUUGCCUCGUAAAA---AAGCCGCAAUU-UAA
Ae.salmoni  CGAG-GUGCGGUAGGCCUCGUUAAC---AAACCGCAAA--AAA
S.typhimur  CGAG-GGGCGGUUGGCCUCGUAAA----AAGCCGCAAA--AAA
E.coli      CGAG-GGGCGGUUGGCCUCGUAAA----AAGCCGCAAA---AA
Yer.pestis  CGAG-GUGCGGUG-GCCUCGUAAA----AAACCGCAAA-AAAA
V.cholerae  CGAG-GUGCGGUAGGCCUCGUUAAC---AAACCGCAAA--AAA
H.influenz  CGAG-GUGCGGUAGGCCUCGUAAAU---AAACCGCAAA--AAA
H.actinomy  CGAG-GUGCGGUAGGCCUCGUAAAU---AAACCGCAAA--AAA
                                              CODING SEQUENCE
                                                    ↓
Leg.pneumo  A-UAAAUgcaaacgaugaaaacuuugcuggugggggaagcuaucgcugccUAA-----UAAGCACUUU
Chr.vinosu  A-UAGUUgccaacgacgacaacuac-----------gcucucgcugcuUAA-----UCCCAGCGGG
Dcb.nodosu  A-UAGUUgcaaacgacgacaacuac-----------gcuuuagcggcuUAA-----UUCCCGCUUU
Ps.aerugin  A-UAGUUgccaacgacgacaacuac-----------gcucuagcugcuUAA------UGCGGCUAG
Ps.fluores  A-UAGUUgccaaugacgaaaccuac---ggggaauacgcucucgcugcgUAA-------GCAGCCUU
Mar.hydroc  A-UAGUCgcaaacgaaaaacuac-------------gcacuggcggcgUAA---GCCGUU-CCAGU
Shw.putref  A-UAGUUgcaaacgacgauaacuac-----------gcucuagccgcuUAA-----UGCCGCUAG
Psm.halopl  AGUAAUCgcaaacgacgauaacuac-----------ucucuagcagcuUAG------GCUGGCUAG
Ae.salmoni  A-UAGUCgcaaacgacgaaaacuac-----------gcacuagcagcuUAAUAACCUGCAUAGAGC
S.typhimur  A-UAGUCgcaaacgacgaaaccuac-----------gcuuuagcagcuUAAUAACCUGCUUAGAGC
E.coli      A-UAGUCgcaaacgacgaaaacuac-----------gcuuuagcagcuUAAUAACCUGCUUAGAGC
Yer.pestis  A-UAGUUgcaaacgacgaaaacuac-----------gcacuagcagcuUAAUAACCUGCUUAGAGC
V.cholerae  A-UAGUCgcaaacgacgaaaacuac-----------gcacuagcagcuUAAUACCCUGCUCAGAGC
H.influenz  A-UACUCgcaaacgacgaacaauac-----------gcuuuagcagcuUAAUAACCUGCAUUUAGC
H.actinomy  A-UAGUCgcaaacgacgaacaauac-----------gcuuuagcagcuUAAUAACCUGCCUUUAGC
                                                              ══════    ════
                                                                  H4
```

FIG. 10A

```
Leg.pneumo  AGUUAAACCAUCACUGUGUACUGGCCAAUAAACCCAGUAUC
Chr.vinosu
Dcb.nodosu
Ps.aerugin
Ps.fluores  AGCCCUUCCCUCCUGGUACCUUCGGGUCCAG
Mar.hydroc
Shw.putref
Psm.halopl
Ae.salmoni
S.typhimur
E.coli
Yer.pestis
V.cholerae
H.influenz
H.actinomy Leg.pneumo  CCGUUCG-ACCGAGCCC--GCUUAUC-GGUAUCGAA-------UCAACGGUCAU-AAGAGAU-AAGCU
Chr.vinosu  CCUCUGA-CCGUCACUU--GCCUGUGGGCGGCGGAUU------CCAGGGGUAAC-CUCACAC-AGGAU
Dcb.nodosu  CGCUUAC-CUAGAUUU---GUCUGUGGGUUUACC---------GUAAGCGACAU--UAACAC-AGAAU
Ps.aerugin  CAGUCGC-UAGGGGAU---GCCUGUAAACCCGAAA--------CGACUGUCAG-AUAGAAC-AGGAU
Ps.fluores  CAAUCAU-CAGGGGAU---GUCUGUAAACCCAAAG--------UGAUUGUCAU-AUAGAAC-AGAAU
Mar.hydroc  CGUCCUG-GCUGAGGC---GCCUAUAACUCAGUAGCAACAUCCCAGGACGUCAU-CGCUUAU-AGGCU
Shw.putref  CCAUCUA-CCACACGCUUUGCACAUGGGCAGUGGAUU------UGAUGGUCAU-CUCACAUCGUGCU
Psm.halopl  CGCUCCU-UCCAUGUAU--UCUUGUG-GACUGGAUUUU------GGAGUGUCACCCUAACAC-CUGAU
Ae.salmoni  CCUUCUA-CCCUAGCUU--GCCUGUGUCCUAGGGAAUC------GGAAGGUCAU-CCUUCAC-AGGAU
S.typhimur  CCUCUCU-CCCUAGCCUCCGCUCUUAGGACGGGGAUCA----AGAGAGGUCAAACCCAAAA-GAGAU
E.coli      CCUCUCU-CCCUAGCCUCCGCUCUUAGGACGGGGAUCA----AGAGAGGUCAAACCCAAAA-GAGAU
Yer.pestis  CCUCUCU-CCCUAGCCUCCGCUCUUAGGACGGGGAUCA----AGAGAGGUCAAACCUAAAA-GAGCU
V.cholerae  CCUUCCU-CCCUAGCUUCCGCUUGUAAGACGGGGAAAUC----AGGAAGGUCAAACCAAAUC-AGCU
H.influenz  CUUCGCG-CUCCAGCUUCCGCUCGUAAGACGGGGAUAA-----CGCGGAGUCAAACCAAAAC-GAGAU
H.actinomy  CUUCGCU-CCCCAGCUUCCGCUCGUAAGACGGGGAUAA-----AGCGGAGUCAAACCAAAAC-GAGAU
                                         PK2
```

FIG. 10B

```
                          PK3
             ┌────────────────────────────────────────────────┐
Leg.pneumo   -AGCG-UCCU-AAUCU--AUCCC-GGGUU-AUGG-CGCGAAA-CU-CA--GGGAAU
Chr.vinosu   -CGUG-GUGA-CGGGA--GUCCG-GACCU-GAUC-CACUAAAACC-UA-ACGGAAU
Dcb.nodosu   -CGCU-GGUU-AACG--CGUCCGC-UGUU-AAUC-GGUUAAA-UU-AA-GCGGAAU
Ps.aerugin   -CGCC-GCCA-AGUU--CGCUGUA-GACG-UAAC-GGCUAAAACU-CA-UACAGCU
Ps.fluores   -CGCC-GUGC-AGUA--CGUUGUG-GACG-AAGC-GGCUAAAACU-UA-CACAACU
Mar.hydroc   GCUCC-GUUC-ACCAG-AGCUCA-CUGGU-GUUC-GGCUAAG-AU-UA-AAGAGCU
Shw.putref   -AGCGAGGGA-ACCC--UGUCUGG-GGGU-GAAC-CGCGAAACAG-UA-CCGGACU
Psm.halopl   -CGCGACGGA-AACCC-UGGCCG-GGGUU-GAAG-CGUUAAAACU-AA-GCGGCCU
Ae.salmoni   -CGUG-UGGA-AGUCC-UGCUCG-GGGCG-GAAG-CAUUAAAACC-AA-UCGAGCU
S.typhimur   -CGCC-CGGA-UGCCC-UGCCUG-GGGUU-GAAG-CGUUAAAACG-AA-UCAGGCU
E.coli       -CGCC-UGGA-AGCCC-UGCCUG-GGGUU-GAAG-CGUUAAAACUUAA-UCAGGCU
Yer.pestis   -CGUG-UGGA-AACCU-UGCCUG-GGGUG-GAAG-CAUUAAAACU-AA-UCAGGAU
V.cholerae   -GCCG-UGGA-UUCCCCACCUGA-GGGAUGAAG-CGCGAGAUCU-AAUUCAGGUU
H.influenz   -CGUG-UGGA-AGCCACCGUUUGA-GGAUCGAAG-CACUAAAUUG-AA-UCAAACU
H.actinomy   -CGUG-UGGA-AGCCACCGUUUGA-GGAUCGAAG-CAUUAAAUUA-AA-UCAAAGU ┌──────────────────────────────────────────────────────────┐
Leg.pneumo   CGCUGUGUAU-CAUCCUGCCC-GUCGGAGGAGCCACAGUUAAAUUCAAAAGACAAGGC--
Chr.vinosu   CGCCGACUGAUCGCCCUGCCC-UUCGGGCGGCAGAAGGCUAAAAACAAUAGAGUGGGC--
Dcb.nodosu   CGCUUGUAAA-AUGCCUGAGC-GUUGGCUGUUUAUGAGUUAAACCUAAUUAACUGCUC--
Ps.aerugin   CGCUCCAAGC--ACCCUGCCA-CUCGGCGGCGCGGAGUUAA-CUCAGUAGAGCUGGC--
Ps.fluores   CGCCCAAAGC--ACCCUGCCC-GUCGGUCGCUGAGGGUUAA-CUUAAUAGACACGGC--
Mar.hydroc   CGCCUCUUGC--ACCCUGACC-UUCGGGUCGCUUGAGGUUAA-AUCAAUAGAA-GGACAC
Shw.putref   CACCGUGUGG-GAUCCUGUCU-UUCGGAGUUCAAACGGUUAA-ACAAUA-GAA-AGAC--
Psm.halopl   CGCCUUUAUC-UACCGUGUUU-GUCCGGGAUUUAAAGGUUAA-UUAAAU-GACAAUAC-- } PK4
Ae.salmoni   AGUCAAUUCG-UGGCGUGUCU-CUCCGCAGCGGGUUGGCGAA-UGUAAA-GAG-UGAC--
S.typhimur   AGUCUGGUAG-UGGCGUGUCC-GUCCGCAGGUGCCAGGCGAA-UGUAAA-GAC-UGAC--
E.coli       AGUUUGUUAG-UGGCGUGUCC-GUCCGCAGCUGGCAAGCGAA-UGUAAA-GAC-UGAC--
Yer.pestis   AGUUUGUCAG-UAGCGUGUCC-AUCCGCAGCUGGCCGGCGAA-UGUAAU-GAUUGGAC--
V.cholerae   AGCCAUUCGU-UAGCGUGUCG-GUUCGCAGGCG-GUGGUGAA-AUUAAA-GAU-CGAC--
H.influenz   AGCUUAAGUU-UAGCGUGUCU-GUCCGCA-UGCUUAAGUGAA-AUUAAA-GACAGAGAC--
H.actinomy   AGCUUAAUUG-UCGCGUGUCC-GUCAGCA-GGAUUAAGUGAA-UUUAAA-GACCGGAC--

Leg.pneumo   UAUGCAUGUAGAGCUAAAGGCAGAGGACUUGCGGACGCGG**********************
Chr.vinosu   UAAGCAUGUAGGACCGAGGGCAGAGGGCUUGCGGACGCGG**********************
Dcb.nodosu   UAAACAUGUAGUACCAAAAGUUAAGGAUUCGCGGACGGGGGUUCAAAUCCCCCCGCCUCCACCA
Ps.aerugin   UAAGCAUGUAGAACCGAUAGCGGGAGCUGGCGGACGGGGGUUCAAAUCCCCCCGGCUCCACCA
Ps.fluores   UACGCAUGUAGUACCGACAGCAGAGUACUGGCGGACGGGG**********************
Mar.hydroc   UAAGCAUGUAGACCUCAAGGCCUAGUGCUGGCGGACGCGG**********************
Shw.putref   UAAGCAUGUAGCGCCUUGGAUGUAGGUUUUCUGGACGCGGGUUCAAGUCCCGCCGCCUCCACCA
Psm.halopl   UAAACAUGUAGUACCGACGGUCGAGGCUUUUCGGACGGGG**********************
Ae.salmoni   UAAGCAUGUAGUACCGAGGAUGUAGUAAUUUUGGACGGGG**********************
S.typhimur   UAAGCAUGUAGUACCGAGGAUGUAGGAAUUUCGGACGCGGGUUCAACUCCCGCCAGCUCCACCA
E.coli       UAAGCAUGUAGUACCGAGGAUGUAGGAAUUUCGGACGCGGGUUCAACUCCCGCCAGCUCCACCA
Yer.pestis   UAAGCAUGUAGUGCCGACGUGUAGUAAUUUCGGACGGGGGUUCAAAUCCCCCCAGCUCCACCA
V.cholerae   UAAGCAUGUAGUACCAAAGAUGAAUGGUUUUCGGACGGGGGUUCAACUCCCCCCAGCUCCACCA
H.influenz   UAAACGUGUAGUACUGAAGGUAGAGUAAUUUCGGACGGGGGUUCAACUCCCCCCAGCUCCACCA
H.actinomy   UAAACGUGUAGUGCUAACGGCAGAGGAAUUUCGGACGGGGGUUCAACUCCCCCCAGCUCCACCA ③'
             H2            H5                H6          H1
```

FIG. 10C

SEQUENCE LISTING

```
<160> NUMBER OF SEQ ID NOS: 175

<210> SEQ ID NO 1
<211> LENGTH: 21
<212> TYPE: DNA
<213> ORGANISM: Artificial
<220> FEATURE:
<223> OTHER INFORMATION: PCR primer

<400> SEQUENCE: 1
ggggctgatt ctggattcga c                                                21

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
tggagctggc gggagttgaa c                                                21

<210> SEQ ID NO 3
<211> LENGTH: 21
<212> TYPE: DNA
<213> ORGANISM: Artificial
<220> FEATURE:
<223> OTHER INFORMATION: PCR primer

<400> SEQUENCE: 3 ggggcggaa aggattcgac g                                                 21

<210> SEQ ID NO 4
<211> LENGTH: 21
<212> TYPE: DNA
<213> ORGANISM: Artificial
<220> FEATURE:
<223> OTHER INFORMATION: PCR primer
```

<400> SEQUENCE: 4
tggaggcggc gggaatcgaa c                                              21

<210> SEQ ID NO 5
<211> LENGTH: 21
<212> TYPE: DNA
<213> ORGANISM: Artificial
<220> FEATURE:
<223> OTHER INFORMATION: PCR primer

<400> SEQUENCE: 5
ggggatgtca tggttttgac a                                              21

<210> SEQ ID NO 6
<211> LENGTH: 21
<212> TYPE: DNA
<213> ORGANISM: Artificial
<220> FEATURE:
<223> OTHER INFORMATION: PCR primer

<400> SEQUENCE: 6
tggagatggc gggaatcgaa c                                              21

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
ggggatgaca ggctatcgac a                                              21

<210> SEQ ID NO 8
<211> LENGTH: 21
<212> TYPE: DNA
<213> ORGANISM: Artificial
<220> FEATURE:
<223> OTHER INFORMATION: PCR primer

<400> SEQUENCE: 8
tggagatggc gggacttgaa c                                              21

<210> SEQ ID NO 9
<211> LENGTH: 352
<212> TYPE: DNA
<213> ORGANISM: Acidobacterium capsulatum

<400> SEQUENCE: 9
gggggcggaa aggattcgac ggggttgact gcggcaaaga ggcatgccgg ggggtgggca      60
cccgtaatcg ctcgcaaaac aatacttgcc aacaacaatc tggcactcgc agcttaatta    120
aataagttgc cgtcctctga ggcttcgcct gtgggcgag gcaggacgtc atacagcagg     180
ctggttcctt cggctgggtc tgggccgcgg ggatgagatc cacggactag cattctgcgt    240
atcttgtcgc ttctaagcgc agagtgcgaa acctaaagga atgcgactga gcatggagtc    300
tcttttctga caccaatttc ggacgcgggt tcgattcccg ccgcctccac ca            352

<210> SEQ ID NO 10
<211> LENGTH: 353
<212> TYPE: DNA
<213> ORGANISM: Coprothermobacter proteolyticus

<400> SEQUENCE: 10

-continued

```
ggggcggaa aggattcgac ggggagtcgg agccttgagc tgcaggcagg gttggctgcc      60
acaccttaaa aagggtagca aggcaaaaat aaatgccgaa ccagaatttg cactagctgc    120
ttaatgtaag cagccgctct ccaaactgag gctgcataag tttggaagag cgtcaaccca    180
tgcagcggct cttaagcagt ggaccagct gtttaagggt gaaagagtg gtgctgggca     240 gtgcggttgg gcttcctggg ctgcactgtc gagacttcac aggagggcta agcctgtaga    300
cgcgaaaggt ggcggctcgt cggacgcggg ttcgattccc gccgcctcca cca           353
```

<210> SEQ ID NO 11
<211> LENGTH: 399
<212> TYPE: DNA
<213> ORGANISM: Bacteroides thetaiotaomicron

<400> SEQUENCE: 11

```
ggggctgatt ctggattcga cagcgggcag aaatggtagg taagcatgca gtgggtcggt     60
aatttccact taaatctcag ttatcaaaac tttatctggc gaaactaatt acgctcttgc    120
tgcttaatcg aatcacagta gattagctta atccaggcac taggtgccag gacgagacat    180
cactcggaag ctgttgctcc gaagcattcc ggttcagtgg tgcagtaaca tcggggatag    240
tcagaagcgg cctcgcgttt tgatgaaac tttagaggat aaggcaggaa ttgatggctt     300
tggttctgct cctgcacgaa aatttaggca agataagca tgtagaaagc ttatgatttc     360
ctcgtttgga cgagggttca actcccgcca gctccacca                           399
```

<210> SEQ ID NO 12
<211> LENGTH: 352
<212> TYPE: DNA
<213> ORGANISM: Dictyoglomus thermophilum

<400> SEQUENCE: 12

```
ggggctgatt ctggattcga cagggagtac aaggatcaaa agctgcaagc cgaggtgccg     60
ttacctcgta aaacaacggc aaaaagaag tgccaacaca aatttagcat tagctgctta     120
atttagcagc tacgctcttc taacccgggc tggcagggtt agaagggtgt cataatgagc    180
cagctgcccc ttccgactcc cctaaggaag ggaaagatgt aggggatagg tgcttacaga    240
atcctgcggg agggagtctg taagtgccga aaagttaaaa ctcccgctaa gcttgtagag    300
gcttttgatt cttgctctct ggacgcgggt tcaactcccg ccagctccac ca            352
```

<210> SEQ ID NO 13
<211> LENGTH: 313
<212> TYPE: DNA
<213> ORGANISM: Artificial
<220> FEATURE:
<223> OTHER INFORMATION: sequence isolated from rumenal fluid

<400> SEQUENCE: 13

```
acgcccttgt ctcagacgag ggcactcgtt aaaaagtctg aaaagaataa ctgcagaacc     60
tgtagctatg gctgcttaat ttaagggcaa cccttggatc cgcctccatc ccgaagggt    120 ggcatccgag tcgcaaatcg ggataggatg gatcttggca acgaggagta catccgaaat    180
ttgtcgctgc tggctgaagc atcgccgttc ctctttgggc gtggcaaggc aagattaaat    240
tcagaggata agcgtgtagt agcgagtgag taggtgtttt tggacgcggg ttcaagtccc    300
gccatctcca cca                                                      313
```

<210> SEQ ID NO 14

```
<211> LENGTH: 350
<212> TYPE: DNA
<213> ORGANISM: Artificial
<220> FEATURE:
<223> OTHER INFORMATION: sequence isolated from sludge

<400> SEQUENCE: 14
ggggatgtca tggttttgac agggaaccag gaggtgtgag atgcatgccg gagacgctgt      60
ccgctccgtt atcaagcagc aaacaaaact aattgcaaac aacaattact ccttagcagc     120
gtaagcagct aacgttcaac ctctccggac cgccgggagg ggatttgggc gtcgaaacag     180
cgcggacgct ccggatagga cgcccataat atccggctaa gaccatgggt ctggctctcg     240
cgggtctgat tgtcttccac cgcgcgggcc gcgatcaaag acaactaagc atgtaggttc     300
ttgcatggcc tgttctttgg acgcgggttc gattcccgcc atctccacca                350

<210> SEQ ID NO 15
<211> LENGTH: 359
<212> TYPE: DNA
<213> ORGANISM: Fibrobacter succinogenes

<400> SEQUENCE: 15
ggggctgatt ctggattcga cagggttacc gaagtgttag ttgcaagtcg aggtctcaga      60
cgagggctac tcgttaaaaa gtctgaaaaa aaataagtgc tgacgaaaac tacgcactcg     120
ctgcctaatt aacggcaacg ccgggcctca ttccgctccc atcgggtgt acgtccggac      180 gcaatatggg atagggaagt gtcatgcctg ggggcatctc ccgagatttt ctaggctggt     240
caaactccgc gccgaccttc ttgggcgtgg ataagacgag atcttaaatt cgaagggaac     300
acttgtagga acgtacatgg acgtgatttt ggacaggggt tcaactcccg ccagctcca     359

<210> SEQ ID NO 16
<211> LENGTH: 350
<212> TYPE: DNA
<213> ORGANISM: Fusobacterium mortiferum

<400> SEQUENCE: 16
ggggctgatt ctggattcga cggggttatg aggttatagg tagcatgcca ggatgaccgc      60
tgtgagaggt caacacatcg tttagatgga aacagaaatt acgctttagc tgcttaatta     120
gtcagctcac ctctggtttc tctcttctgt aggagaatcc aaccgaggtg ttaccaatat     180
acagattacc tttagtgatt tctctaagct caaagggaca ttttagagaa tagcttcagt     240
tagccctgtc tgcgggagtg attgttgcga aataaaatag tagactaagc attgtagaag     300
cctatggcgc tggtagtttc ggacacgggt tcaactcccg ccagctccaa                350

<210> SEQ ID NO 17
<211> LENGTH: 377
<212> TYPE: DNA
<213> ORGANISM: Corynebacterium xerosis

<400> SEQUENCE: 17
ggggctgatt ctggattcga cttcgtacat tgagccaggg gaagcgtgcc ggtgaaggct      60
ggagaccacc gcaagcgtcg cagcaaccaa ttaagcgccg agaactctca gcgcgactac     120
gccctcgctg cctaagcagc gaccgcgtgt ctgtcagacc gggtaggcct ctgatccgga     180
ccctggcatc gtttagtggg gctcgctcgc cgacttggtc gcaagggtcg gcggggacac     240
tcacttgcga ctgggcccgt catccggtca tgttcgactg aaccgagggg ccgagcagag     300
accacgcgcg aactgcgcac ggagaagccc tggcgaggtg acggaggacc cgggttcaac     360
```

```
tcccgccagc tccacca                                              377

<210> SEQ ID NO 18
<211> LENGTH: 372
<212> TYPE: DNA
<213> ORGANISM: Micrococcus luteus
<220> FEATURE:
<221> NAME/KEY: misc_feature
<222> LOCATION: (1)..(372)
<223> OTHER INFORMATION: n is an unknown base

<400> SEQUENCE: 18
ggggctattc tggattcgac ggtgtgtgtc gcgtcgggag aagcgggccg aggatgcaga    60
gtcatctcgt caaacgctct ctgcaaacca ataagtgccg aatccaagcg cactgacttc   120
gctctcgctg cctgatcagt gatcgagtcc gtcaccccga ggtcgctgtc gcctcggatc   180
gtggcgtcag ctagatagcc actgggcgta accctcgccg ggggtcgtga cgccgacatc   240
aatccggctg ggtccgggtt ggccgcccgt ctgcgggacg gccaggaccg agcaacaccc   300
acagcagact gcgcccggag aagacctggc aacacctcat cggacgcggg ttcaactccc   360
gcantcccac ca                                                      372

<210> SEQ ID NO 19
<211> LENGTH: 372
<212> TYPE: DNA
<213> ORGANISM: Mycobacterium smegmatis

<400> SEQUENCE: 19
tcatctcggc ttgttcgcgt gaccgggaga tccgagtaga gacatagcga actgcgcacg    60
gagaggggct gattcctgga ttcgacttcg agcatcgaat ccaggaaagc gtgccggtgc   120
aggcaagaga ccaccgtaag cgtcgttgca accaattaag cgccgattcc aatcagcgcg   180
actacgccct cgctgcctaa gcgacggctg gtctgtcaga ccgggagtgc cctcggcccg   240
gatcctggca tcagctagag ggacccaccc acgggttcgg tcgcgggacc tgtggggaca   300
tcaaacagcg actgggatcg agcctcgagg acatgccgta ggacccgggt tcaactcccg   360
ccagctccac ca                                                      372

<210> SEQ ID NO 20
<211> LENGTH: 355
<212> TYPE: DNA
<213> ORGANISM: Bacillus badius

<400> SEQUENCE: 20
gggggtgatt ctggattcga cagggatagt tcgagcttgg gctgcgagcc ggagggccgt    60
cttcgtacca acgcaaacgc ctaaatataa ctggcaaaaa agatttagct ttagctgcct   120
aatataggtt cagctgctcc tcccgctatc gtccatgtag tcgggtaagg ggtccaaact   180
tagtggacta cgccggagtt ctccgcctgg ggacaaagga agagatcaat caggctagct   240
gcccggacgc ccgtcgatag gcaaaaggaa cagtgaaccc caaatatatc gactacgctc   300
gtagacgttc aagtggcgtt atctttggac gtgggttcaa ctcccgccag ctcca        355

<210> SEQ ID NO 21
<211> LENGTH: 357
<212> TYPE: DNA
<213> ORGANISM: Bacillus brevis

<400> SEQUENCE: 21
```

```
gggggcggaa aggattcgac ggggatggta gagcatgaga agcgagccgg ggggttgcgg    60
acctcgtcac caacgcaaac gccattaact ggcaacaaac aactttctct cgctgcttaa   120
taaccagtga ggctctccca ctgcatcggc ccgtgtgccg tggatagggc tcaactttaa   180
cgggctacgc cggaggcttc cgcctggagc caaaggaaga agaccaatca ggctaggtgc   240
caggtcagcg cgtcactccg cgaatctgtc accgaaactc taaacgagtg actgcgctcg   300
gagatgctca tgtatcgctg ttttcggacg ggggttcgat tcccgccgcc tcaccca     357
```

<210> SEQ ID NO 22
<211> LENGTH: 354
<212> TYPE: DNA
<213> ORGANISM: Bacillus thermoleovorans

<400> SEQUENCE: 22

```
gggggcggaa aggattcgac gggggtaggt cgagcttaag cggcgagccg aggggggacgt   60 cctcgtaaaa acgtcaccta aagataactg gcaaacaaaa ctacgcttta gctgcctaat   120
tgctgcagct agctcctccc gccatcgccc gcgtggcgtt cgagggggctc atatggagcg   180 ggctacgccc aaatccgccg cctgaggatg agggaagaga cgaatcaggc tagccgccgg   240
gaggcctgtc ggtaggcgga acggacggcg aagcgaaata taccgactac gctcgtagat   300
gcttaagtgg cgatgcctct ggacgtgggt tcgattcccg ccgcctcccc acca          354
```

<210> SEQ ID NO 23
<211> LENGTH: 384
<212> TYPE: DNA
<213> ORGANISM: Clostridium innocuum

<400> SEQUENCE: 23

```
gggggcggaa aggattcgac gggatatgt ctggtacaga ctgcagtcga gtggttacgt    60
aataaccaat taaatttaaa cggaaaaact aaattagcta acctctttgg tggaaaccag   120
agaatggctt tcgctgctta ataaccgata taggttcgca gccgcctctg catgcttctt   180
ccttgaccat gtggatgtgc gcgtaagacg caagggataa ggaatctggt ttgcctgaga   240
tcagattcac gaaaattctt caggcacatt catcagcgga tgttcatgac ctgctgatgt   300
cttaatcttc atggactaaa ctgtagaggt ctgtacgtgg ggctgtttct ggacaggagt   360
tcgattcccg ccgcctcacc acca                                         384
```

<210> SEQ ID NO 24
<211> LENGTH: 349
<212> TYPE: DNA
<213> ORGANISM: Clostridium lentocellum

<400> SEQUENCE: 24

```
gggggcggaa aggattcgac gggggtcaca tctactgggg cagccatccg tagaacgccg    60
gagtctacgt taaaagctgg cacttaaagt aaacgctgaa gataatttag caatcgctgc   120
ctaattaagg cgcagtcctc ctaggtcttc cgcagcctag atcagggctt cgactcgcgg   180
atccttcacc tggcaaagct ttgagccaac gtgaacacta tgaagctact aaaatctaga   240
gcctgtcttt gggcgctaga tggagggaat gtcaaaacaa agaatatgat ggtagagacc   300
acgctatatg ggctttcgga cagggggttcg attcccgccg ccttcacca              349
```

<210> SEQ ID NO 25
<211> LENGTH: 358
<212> TYPE: DNA
<213> ORGANISM: Clostridium perfringens

<400> SEQUENCE: 25

```
ggggctgatt ctggattcga cggggggtaag atgggtttga taagcgagtc gagggaagca    60
tggtgcctcg ataataaagt atgcattaaa gataaacgca aagataatt ttgcattagc     120
agcttaattt agcgctgctc atccttcctc aattgcccac ggttgagagt aagggtgtca    180
tttaaaagtg gggaaccgag cctagcaaag ctttgagcta ggaacggaat ttatgaagct    240
taccaaagag gaagtttgtc tgtggacgtt ctctgaggga attttaaaac acaagactac    300
actcgtagaa agtcttactg gtctgctttc ggacacgggt tcaactcccg ccactcca     358
```

<210> SEQ ID NO 26
<211> LENGTH: 362
<212> TYPE: DNA
<213> ORGANISM: Clostridium stercorarium

<400> SEQUENCE: 26

```
gggggcggaa aggattcgac ggggttattg aagcaagagt agcgggtaga ggattctcgt    60
tggcctcttt aaaaaacgag agctaaaaat aaacgcaaac aacgataact acgctttagc   120
tgctgcgtaa gtaacacgca gcccgtcggc cccggggttc ctgcgcctcg ggataccggc   180
gtcatcaagg cagggaacca gccggatcag gcttcaggtc cggtgggatt taatgaagct   240
accgacttat aaagcctgtc tctgggcgtt ataagaaggg aatgtcaaaa cagagactgc   300
acccggagaa gctcttgtgg atatggttcc ggacacgagt tcgattcccg ccgcctccac   360
ca                                                                  362
```

<210> SEQ ID NO 27
<211> LENGTH: 369
<212> TYPE: DNA
<213> ORGANISM: Enterococcus faecium
<220> FEATURE:
<221> NAME/KEY: misc_feature
<222> LOCATION: (1)..(369)
<223> OTHER INFORMATION: n is an unknown base

<400> SEQUENCE: 27

```
ggggctgatt atggattcga caggatngtt gagcttgaat tgcgtttcgt aggttacggc    60
tacgttaaaa cgttacagtt aaatataact gctaaaaacg aaacaattc tttcgcttta    120
gctgcctaaa aaccagctag cgaagatcct cccggcatcg cccatgtgct cgggtcaggg   180
tcctaatcga agtgggatac gctaaatttt tccgtctgta aaatttagag gagcttacca   240
gactagcaat acaagaatgc ctgtcactcg gcacgctgta aagcgaacct ttaaatgagt   300
gtctatgaac gtagagattt aagtgggaat atgtttgga cgcgggttca actcccgcca   360
gctccacca                                                           369
```

<210> SEQ ID NO 28
<211> LENGTH: 353
<212> TYPE: DNA
<213> ORGANISM: Heliobacillus mobilis

<400> SEQUENCE: 28

```
ggggctgatt ctggattcga cggggaacgt gtttgcttgg gatgcgagcc gggttgccgc    60
caggaccgta aaagggcgg aaggctttaa ttgccgaaga taactacgct ttagctgctt    120
aattgcagtc taacctcttc tcctctgtgc tctcggtgag gatgtaaggg gtcatttaag   180
agagctggct tcgaccaatt ctcggaggtc caagcgagat ttatcgagat agcctgacca   240
```

```
acgctctgtc tgccgtgcgg aaggaaggcg aaatctaaaa cgacagacta cgctcgtagt    300
gtcctttgtg ggcatttctt cggacgcggg ttcaactccc gccagctcca cca           353
```

<210> SEQ ID NO 29
<211> LENGTH: 353
<212> TYPE: DNA
<213> ORGANISM: Heliospirillum gestii

<400> SEQUENCE: 29

```
ggggctgatt ctggattcga cggggaacgt gtttgcttag gacgcgagcc gggttgccgc    60
caggaccgta aaagggcgg aaggcttttaa ttgccgaaga taactacgct ttagctgctt    120
aattgcagtc taacctcttc tcctctgtgc tctcggtgag gatgtaaggg gtcatttaag    180
agagctggct cgaaccaatt ctcggaggtt cgggtaagac ttatcgagat agcctgacca    240
acgctctgtc tgccgtgcgg aaggatggcg aaatctaaaa cgacagaata cgctcgtagt    300
gtcctttgtg ggcatttctt cggacgcggg ttcaactccc gccagctcca cca           353
```

<210> SEQ ID NO 30
<211> LENGTH: 368
<212> TYPE: DNA
<213> ORGANISM: Lactobacillus acidophilus

<400> SEQUENCE: 30

```
ggggctgatt ctggattcga caggcgtaga cccgcattga ctgcggttcg taggttacgt    60
ctacgtaaaa acgttacagt taaatataac tgcaaataac aaaaattctt acgcattagc    120
tgcttaattt agcgcatgcg ttgctctttg tcggtttact cgtggctgac actgagtatc    180
aacttagcga gttacgttta actacctcac ctgaatagtt gaaaagagtc ttagcaggtt    240
agctagtcca tactagccct gttatatggc gttttggact agtgaagttc aagtaatata    300
actatgatcg tagaggtcag tgacgagatg cgtttggaca gcgggttcaa ctcccgccag    360
ctccacca                                                              368
```

<210> SEQ ID NO 31
<211> LENGTH: 360
<212> TYPE: DNA
<213> ORGANISM: Staphylococcus epidermidis

<400> SEQUENCE: 31

```
ggggctgatt ctgcattcga caggggtccc cgagcttatt aagcgtgtgg agggttggct    60
ccgtcatcaa cacatttcgg ttaaatataa ctgacaaatc aaacaataat ttcgcagtag    120
ctgcgtaata gccactgcat cgcctaacag catctcctac gtgctgttaa cgcgattcaa    180
ccctagtagg atatgctaaa cactgccgct gaagtctgt ttagatgaaa tataatcaag     240
ctagtatcat gttggttgtt tattgcttag catgatgcga aaattatcaa taaactacac    300
acgtagaaag atttgtatca ggacctctgg acgcgggttc aactcccgcc agctccacca    360
```

<210> SEQ ID NO 32
<211> LENGTH: 368
<212> TYPE: DNA
<213> ORGANISM: Streptococcus faecium

<400> SEQUENCE: 32

```
ggggctgatt ctggattcga caggcacagt ttgagcttga attgcgtttc gtaggttacg    60
tctacgttaa aacgttacag ttaaatataa ctgctaaaaa cgaaacaac tcttacgctt     120 tagctgccta aaaacagtta gcgtagatcc tctcggcatc gcccatgtgc tcgagtaagg    180
```

```
gtctcaaatt tagtgggata cgtgacaact ttccgtctgt aagttgttaa agagatcatc    240
agactagcga tacagaatgc ctgtcactcg gcaagctgta aagcgaaacc acaaatgagt    300
tgactatgaa cgtagatttt taagtggcga tgtgtttgga cgcgggttca actcccgccg    360
ttccacca                                                             368

<210> SEQ ID NO 33
<211> LENGTH: 328
<212> TYPE: DNA
<213> ORGANISM: Thermoanaerobacterium saccharolyticum

<400> SEQUENCE: 33
ggggtagtag aggtaaaagt agcgagccga ggttccatct gctcgtaaaa cggtggactt     60
aaatataaac gcaaacgata atttagctta cgctgcttaa ttacaagcag ccgttcaacc    120
tttgattccc acatcaaagg attgggcgtc gatttagtgg ggaactgatt tatcaaagct    180
ttgagataaa tcggatttta tgaagctacc aaagcagtta tcctgtcact gggagaactg    240
cagagggaat gtcaaaacag tgactgcgct cggagaagct tttactgtga caccttcgga    300
ccggggttca actcccgcca gcccacca                                       328

<210> SEQ ID NO 34
<211> LENGTH: 379
<212> TYPE: DNA
<213> ORGANISM: Mycoplasma fermentans

<400> SEQUENCE: 34
ggggctgatt ctggattcga catgcattgg gtgatactaa tatcagtagt ttggcagact     60
ataatgcatc taggctttat aatcgcagaa gataaaaaag cagaagaagt taatatttct    120
tcacttatga ttgcacaaaa aatgcaatca caatcaaacc ttgctttcgc ttagttaaaa    180
gtgacaagtg gttttaaagt tgacattttc ctatatattt taaaatcggc ttttaaggag    240
aacaggagtc tgaaagggtt ccaaaaatct atattgtttg catttcggta gtatagatta    300
attagaaatg ataaactgta aaaagtattg gtattgactt ggtgtgtgga ctcgggttca    360
actcccgcca gctccacca                                                 379

<210> SEQ ID NO 35
<211> LENGTH: 373
<212> TYPE: DNA
<213> ORGANISM: Mycoplasma hyorhinis

<400> SEQUENCE: 35
ggggctgatt ctggattcga catacataaa aggatataaa ttgcagtggt cttgtaaacc     60
ataagacaat ttctttacta agcggaaaag aaaacaaaaa agaagattat tcattattaa    120
tgaatgcttc aactcaatca aatctagctt ttgcatttta aaaaactagt agaccaattt    180
gcttctcacg aattgtaatc tttatattag agaatagtta aaaatctgat cactttttaa    240
tgaatttata gatcacaggc ttttttaatc ttttgttat tttagataaa gagtcttctt     300
aaaaataact aaactgtagg aatttatatt taattatgcg tggacccggg ttcaactccc    360
gccagctcca cca                                                       373

<210> SEQ ID NO 36
<211> LENGTH: 399
<212> TYPE: DNA
<213> ORGANISM: Mycoplasma pirum
```

-continued

```
<400> SEQUENCE: 36
ggggagtcat ggttttgaca tgaatgatgg acccatagag gcagtggggt atgcccctta      60
tagctcaagg tttaaattaa ccgacaaaac tgacgaaaac gttgccgttg atacaaattt     120
attaatcaac caacaagctc aatttaacta cgcatttgca tagtataaaa aaataaattg     180
tgctactcat tgtaattagg ttactaaatt actttgtttt atatagtcct gtaactagtt     240
ctagtgatgt ctataaacta gaatgagatt tatagactta tttgttggcg gttgtgccat     300
agcctaaatc aacaaagaca atttatttat ggtactaaac tgtagattct atgatgaaat     360
tatttgtgga acgggttcg  attcccgcca tctccacca                             399

<210> SEQ ID NO 37
<211> LENGTH: 385
<212> TYPE: DNA
<213> ORGANISM: Mycoplasma salivarium

<400> SEQUENCE: 37
ggggctgatt ctggattcga caggcattcg attcattatg ttgcagtggt ttgcaaacca      60
taaggcacta ggcttttta  aacgcaaaag accaaaaaac agaagatcaa gcagttgatc     120
tagcatttat gaataattca caaatgcaat caaatctagt tttcgcttag taaaattagt     180
caatttatta tggtgctcaa cataataaat ggtagtatga gcttaatatc atatgatttt     240
agttaatatg ataggatttg taactaaact atgttataga aatttgtaaa ttatatatat     300
gacataggaa atttaattta ctaaactgta gatgcataat gttgaagatg tgtggaccgg     360
ggttcaactc ccgccagctc cacca                                           385

<210> SEQ ID NO 38
<211> LENGTH: 362
<212> TYPE: DNA
<213> ORGANISM: Herpetosiphon aurantiacus

<400> SEQUENCE: 38 ggggggcggaa aggattcgac ggggagggcc aatcgtaagt ggcaagccga gacgctgagc     60
ctcgttaaat cggcaacgcc attaactggc aaaaacactt tccgcgctcc tgtagcgctt    120
gctgcctaat taaggcaaca cgtctctact agcctcagcc cgatgggctt gtagcggcga    180
cacttagtcg ggtcgctccc ctagttatgt ctgtgggcta ggggctaaga ttaacaggct    240
ggtcgtggcc cgctttgtct atcgggtggt gcaccgataa gatttaatca atagactacg    300
cttgtagatg cttgcggttt aacttttttgg acgcgggttc gattcccgcc gcctcaccac    360
ca                                                                    362

<210> SEQ ID NO 39
<211> LENGTH: 355
<212> TYPE: DNA
<213> ORGANISM: Thermomicrobium roseum

<400> SEQUENCE: 39
ggggctgatt ctggattcga cagggccgta ggtgcgagga ttgcaggtcg aggtcgccca      60
cgaactcgta aaaggggca  gccaagtaac tggcgagcgc gaactcgctc tggctgcgta    120
attcacgcag ccacgtctgc ccggaccctt ccctggtggg ttcggagcgg cgccgcaag     180 accgggggtgc ccctggccca agcgccggtg cgggccaggt caagcgtgat ccggctcggc    240
tgaccgggat cctgtcggtg ggagcctggc agcgacagta gaacaccgac taagcctgta    300
gcatatcctc ggctgaacgc tctggacgcg ggttcaactc ccgccagctc cacca          355
```

<210> SEQ ID NO 40
<211> LENGTH: 405
<212> TYPE: DNA
<213> ORGANISM: Chlorobium limicola

<400> SEQUENCE: 40

| | | | | | |
|---|---|---|---|---|---|
| ggggctgatt | ctggattcga | caggatacgt | gtgagatgtc | gttgcactcc | gagtttcagc | 60 |
| atggacggac | tcgttaaaca | agtctatgta | ccattagatg | cagacgatta | ttcgtatgca | 120 |
| atggctgcct | gattagcaca | agttaactca | gacgccatcg | tcctgcggtg | aatgcgctta | 180 |
| ctctgaagcc | gccggatggc | ataacccgcg | cttgagccta | cgggttcgcg | caagtaagct | 240 |
| ccgtacattc | atgcccgagg | ggctgtgcgg | gtaatttctc | gggataaggg | gacgaacgct | 300 |
| gctggcggtg | taatcggccc | acgaaaaccc | aatcaccaga | gatgagtgtg | gtgactgcat | 360 |
| cgagcagtgt | tttggacgcg | ggttcaactc | ccgccagctc | cacca | | 405 |

<210> SEQ ID NO 41
<211> LENGTH: 362
<212> TYPE: DNA
<213> ORGANISM: Pirellula staleyi

<400> SEQUENCE: 41

| | | | | | |
|---|---|---|---|---|---|
| ggggctgatt | ctggattcga | ccggatagcc | tgaagcgaat | acggcgtgcc | gtggttgatc | 60 |
| agatggccac | gtaaaaagct | gatcacaaac | ttaactgccg | agagcaatct | cgcacttgct | 120 |
| gcctaactaa | acggtagctt | ccgactgagg | gctttagccg | gagaggccca | aaagttggtc | 180 |
| accaaatccg | gaccgcctcg | tgccatgatc | gaaacgcacg | aggtcaaaaa | agtttcgatc | 240 |
| tagtgcaggg | tgtagccagc | agctaggcga | caaactgtgc | aaaaatcaaa | ttttctgcta | 300 |
| cgcacgtaga | tgtgttcgtg | aaaatgtctc | gggacggggg | ttcaactccc | gccactccac | 360 |
| ca | | | | | | 362 |

<210> SEQ ID NO 42
<211> LENGTH: 346
<212> TYPE: DNA
<213> ORGANISM: Planctomyces limnophilus
<220> FEATURE:
<221> NAME/KEY: misc_feature
<222> LOCATION: (1)..(346)
<223> OTHER INFORMATION: n is an unknown base

<400> SEQUENCE: 42

| | | | | | |
|---|---|---|---|---|---|
| ggggctgatt | ctggattcga | caacctctca | agaggagcgt | ggccactatg | ggactcgatt | 60 |
| atgttgaatt | cgtcatggat | cttgaagaga | ccttcgacat | caaactggat | gacaaacatt | 120 |
| tttcagcagt | caaaacacca | cgcgatttgg | caatcattat | tcgggatcaa | ttagctgctg | 180 |
| aaggcagaat | ctgggatgaa | tcgaatgctt | ttcgcaaaat | ctcgaatttg | aattggacga | 240 |
| tgttgcccga | gttccggatg | tggactcaaa | tcaaaagctc | tctaccagtt | tcttttcacc | 300 |
| gactgcgtcc | cagcacccgt | ctcgttcaac | tcccgccant | ccacca | | 346 |

<210> SEQ ID NO 43
<211> LENGTH: 362
<212> TYPE: DNA
<213> ORGANISM: Planctomyces maris

<400> SEQUENCE: 43

| | | | | | |
|---|---|---|---|---|---|
| ggggctgatt | ctggattcga | ctggttcacc | gtatgttaag | gtggcggtgc | cgtggttgat | 60 |

```
cagttggcca cgtaaaaagc tgatcacaat ctaattgcaa acaagcaatt ttcaatggct    120
gcttaataaa agcaaccccg cttaggaat ctctgtctga ggagtccgac agctggtcac    180
aaaatcagac tggtatcaga tcaatgtccg ctccgtctga tacgagattc gtggtggact    240
ggtttccaac aggctctgtt tatcgtgccc gaagaaacga gactcaaacg ataaaatatg    300
caccgtagag gctttagctg agggttcaca ggacgcgggt tcaactcccg ccagctccac    360
ca                                                                   362

<210> SEQ ID NO 44
<211> LENGTH: 360
<212> TYPE: DNA
<213> ORGANISM: Alcaligenes eutrophus

<400> SEQUENCE: 44
ggggttgatt ctggattcga cgtgggttac aaagcagtgg agggcatacc gaggacccgt     60
cacctcgtta atcaatggga atgcaataac tgctaacgac gaacgttacg cactggccgc    120
ttaattgcgg ccgtcctcgc actggctcgc tgacgggcta gggtcgcaag accacgcgag    180
gtcatttacg tcagataagc tccggaaggg tcacgaagcc ggggacgaaa acctagtgac    240
tcgccgtcgt agagcgtgtt cgtccgcgat gcgccggtta aatcaaatga cagaactaag    300
tatgtagaac tctctgtgga gggcttacgg acgcgggttc aactcccgcc agctccacca    360

<210> SEQ ID NO 45
<211> LENGTH: 362
<212> TYPE: DNA
<213> ORGANISM: Alcaligenes faecalis

<400> SEQUENCE: 45
gggggcggaa aggattcgac gggggtcaag aagcagcaca gggcgtgtcg agcaccagta     60
cgctcgtaaa tccactggaa aactataaac gccaacgacg agcgtttcgc tctagccgct    120
taaggctggg ccactgcact aatttgtctt tgggttaggt agggcaacct acagcagtgt    180
tatttacaaa gaatcgaatc ggtctgcgcc acgaagtccg gttctaaaac ttagtggatc    240
gccaaggaaa ggcctgtcaa ttggcatagt ccaaggttaa aacttaaaat taattgacta    300
cacatgtaga actgtctgtg gacggcttgc ggacgggggt tcgattcccg ccgcctccac    360
ca                                                                   362

<210> SEQ ID NO 46
<211> LENGTH: 366
<212> TYPE: DNA
<213> ORGANISM: Chromobacterium violaceum

<400> SEQUENCE: 46
ggggctgatt ctggattcga cgggggttgc gaagcagatg agggcatacc gggatttcag     60
tcaccccgta aaacgctgaa tttatatagt cgcaaacgac gaaacttacg ctctggcagc    120
ctaacggccg ccagacact acaacggttc gcagatgggc cggggcgtc aaaaccctgt    180 agtgtcactc tacatctgct agtgctgttc cgggttactt ggttcagtgc gaaataatag    240
gtaactcgcc aaagtccagc ctgtccgtcg gcgtggcaga ggttaaatcc aaatgacacg    300
actaagtatg tagaactcac tgtagaggac tttcggacgc gggttcaact cccgcagct    360 ccacca                                                               366

<210> SEQ ID NO 47
<211> LENGTH: 378
```

<212> TYPE: DNA
<213> ORGANISM: Hydrogenophaga palleroni

<400> SEQUENCE: 47

```
ggggctgatt ctggattcga cgtgggttcg gacgcgcagc agggcatgtc gaggttctgt      60
cacctcgtaa atcagcagaa aaaaaccaac tgcaaacgac gaacgtttcg cactcgccgc     120
ttaaacaccg gtgagccttg caacagcagg ccgatgggct gggcaagggg gtcgcaagac     180
ctcccggctg caaggtaatt tacatcggct ggttctgcgt cgggcacctt ggcgcaggat     240
gagattcaag gatgctggct cccgtttag cgtgccactg cgcgactcgg gcggcgagac      300
ccaaatcaga cggctacaca tgtagaactg ctcgaaaaag gcttgcggac ggggttcaa      360
ctcccgccag ctccacca                                                   378
```

<210> SEQ ID NO 48
<211> LENGTH: 365
<212> TYPE: DNA
<213> ORGANISM: Methylobacillus glycogenes

<400> SEQUENCE: 48

```
gggggcggaa aggattcgac gggggttgca aagcagcgca gggcataccg aggcctagtc      60
acctcgtaaa taaactagaa caagtatagt cgcaaacgac gaaacttacg ctctagccgc     120
ttaatcccgg ctggacgctg caccgaaggg cctctcggtc gggtggggta acccacagca     180
gcgtcattaa gagaggatcg tgcgatattg ggttacttaa tatcgtatta aatccaaggt     240
aactcgcctc ctgtttgctt gctcgttggt gagcatcagg ttaaatcaaa caacacagct     300
aagtatgtag aactgtctgt ggagggcttg cggacggggg ttcgattccc gccgcctcac     360
cacca                                                                 365
```

<210> SEQ ID NO 49
<211> LENGTH: 362
<212> TYPE: DNA
<213> ORGANISM: Nitrosomonas cryotolerans

<400> SEQUENCE: 49

```
ggggctgatt ctggattcga cgtgggttgc aaagcagcgc agggcatacc gaggaccaga      60
atacctcgta atacatctg gaaaaaata gtcgcaaacg acgaaaacta cgctttagcc       120
gcttaatacg gctagcctct gcaccgatgg gccttaacgt cgggtctggc aacagacagc     180
agagtcatta gcaaggatcg cgttctgtag ggtcacttta cagaacgtta acaataggt      240
gactcgcctg ccatcagccc gccagctggc ggttgtcagg ttaaattaaa gagcatggct     300
aagtatgtag aactgtctgt agaggacttg cggacgcggg ttcaactccc gccagtccac     360
ca                                                                    362
```

<210> SEQ ID NO 50
<211> LENGTH: 378
<212> TYPE: DNA
<213> ORGANISM: Pseudomonas testosteroni

<400> SEQUENCE: 50

```
ggggctgatt ctggattcga cgtgggttcg ggaccggtgc ggtgcatgtc gagcttgagt      60
gacgctcgta aatctccatt caaaaaacta actgcaaacg acgaacgttt cgcactcgcc     120
gcttaatccg gtgagccttg caacagcacg ctagtgggct gggcaagggg gtagcaatac     180
ctcccggctg caagggaatt ttcattagct ggctggatac cgggcttctt ggtatttggc     240
```

-continued

```
gagattttag gaagctggct acccaagcag cgtgtgcctg cggggtttgg gtggcgagat    300
ttaaaacaga gcactaaaca tgtagatctg tccggcgaag gcttacggac gcgggttcaa    360
ctcccgccag ctccacca                                                  378
```

<210> SEQ ID NO 51
<211> LENGTH: 360
<212> TYPE: DNA
<213> ORGANISM: Ralstonia pickettii

<400> SEQUENCE: 51

```
gggggcggaa aggattcgac gggggttgcg aagcagcgga gggcataccg aggacccgtc     60
acctcgttaa tcaatgggaa tgcaataact gctaacgacg aacgttacgc actggcagcc    120
taagggccgc cgtcctcgca ctggctcgct gacgggctag ggtcgcaaga ccagcgaggt    180
catttacgtc agataagctt taggtgagtc acgggcctag agacgaaaac ttagtgaatc    240
gccgtcgtag agcgtgttcg tccgcgatgc ggcggttaaa tcaaatgaca gaactaagta    300
tgtagaactc tctgtggagg gcttgcggac gcgggttcga ttcccgccgc ctcaccacca    360
```

<210> SEQ ID NO 52
<211> LENGTH: 386
<212> TYPE: DNA
<213> ORGANISM: Variovorax paradoxus

<400> SEQUENCE: 52

```
ggggctgatt ctggattcga cgtgggttcg gagtcgcagc ggggcatgtc gagctgaatg     60
cgctcgtaaa acagattcaa acaaactaac tgcaaacgac gaacgtttcg cactcgctgc    120
ttaattgcca gtgagccttg caacagttgg ccgatgggct gggcaagggg gtctggagca    180
atcctgacct cccggctgca aggataacta catgggctgg ctccgatccg ggtaccttgg    240 gtcgggggcga gaaaatagggg tactggcgtc cggtttagcg tgtgactgcg cgactccgga    300
agcgagactc aaaacagatc actaaacatg tagaactgcg cgatgaaggc ttgcggacgg    360
gggttcaact cccgccagct ccacca                                         386
```

<210> SEQ ID NO 53
<211> LENGTH: 346
<212> TYPE: DNA
<213> ORGANISM: Bdellovibrio bacteriovirus

<400> SEQUENCE: 53

```
gggggcggaa aggattcgac gggggtgctg aagcataagg agcataccgg ggcggatgag     60
gacctcgtta aaaacgtcca ctttgtaatt ggcaacgatt acgcacttgc agcttaatta    120
agcagcacga tcaaccttgt ggtggttccg cacttggatt gatcgtcatt tagggacctc    180
ggcgtgttgg gttttctcca gcagacatgc ttaaatttac tgggggagag gtcttaggga    240
ttttgtctgt ggaagcccga ggaccaatct aaaaacactga ctaagtatgt agcgccttat    300
cgtggatcat ttgcggacgg gggttcgatt cccgccgcct ccacca                   346
```

<210> SEQ ID NO 54
<211> LENGTH: 366
<212> TYPE: DNA
<213> ORGANISM: Myxococcus xanthus

<400> SEQUENCE: 54

```
gggggcggaa aggattcgac gggggcattg aagttcgaga cgcgtgccga gcttgtcagg     60
tagctcgtaa attcaacccg gcaaagacac aaaagccaac gacaacgttg agctcgcgct    120
```

```
ggctgcctaa aaacagccca tagtgcgcgg tcccccgcc ctcggcctgt ggggttggga      180
cagaccgtca taatgcaggc tggctgccga gggtgcctgg acccgaggtg gcgagatctt      240
cccaggaccg gctctgagta tcccgtccgt gggagcctca gggacgtagc aaatcgcgga      300
ctacgcacgt agggtcgaag agcggacggc tttcgacgc gggttcgatt cccgccgcct      360
ccacca                                                                 366
```

```
<210> SEQ ID NO 55
<211> LENGTH: 380
<212> TYPE: DNA
<213> ORGANISM: Sulfurospirillum deleyianum

<400> SEQUENCE: 55
ggggctgatt ctggattcga caggagtagt tttagcttat ggctgcatgt cgggagtgag      60
ggtcttccgt tacacaacct tcaaacaata actgctaaca acagtaacta tcgtcctgct     120
tacgcgctag ctgcgtaagt ttaacaaata atggactgct ctcccctttg atgctatctt     180
aggaggtctt ggagagtatc atagatttga tagctatatt acatgaacgc ctttacatgt     240
aatgaagtta aaggctcgtt ttgcgtagtt ttctgattgt tgtacgaagc aaaattaaac     300
actatcaaca atatctaagc atgtagacgt cataggtggc tattttggga ctgcgggttc     360
aactcccgcc agctccacca                                                 380
```

```
<210> SEQ ID NO 56
<211> LENGTH: 359
<212> TYPE: DNA
<213> ORGANISM: Chromatium vinosum

<400> SEQUENCE: 56
ggggctgatt ctggattcga cgtgggtcgc gaaacctaag gtgcatgccg aggtgcggtt      60
gacctcgtaa aaccctccgc aaacttatag ttgccaacga cgacaactac gctctcgctg     120
cttaatccca gcgggcctct gaccgtcact tgcctgtggg cggcggattc caggggtaac     180
ctcacacagg atcgtggtga cgggagtccg gacctgatcc actaaaacct aacggaatcg     240
ccgactgatc gccctgccct tcgggcggca aaggctaaa aacaatagag tgggctaagc     300
atgtaggacc gagggcagag ggcttgcgga cgcgggttca actcccgcca gctccacca     359
```

```
<210> SEQ ID NO 57
<211> LENGTH: 395
<212> TYPE: DNA
<213> ORGANISM: Pseudomonas fluorescens

<400> SEQUENCE: 57
ggggctgatt ctggattcga cgccggttgc gaacctttag gtgcatgccg agttggtaac      60
agaactcgta atccactgt tgcaactttc tatagttgcc aatgacgaaa cctacgggga     120
atacgctctc gctgcgtaag cagccttagc ccttccctcc tggtaccttc gggtccagca     180
atcatcaggg gatgtctgta aacccaaagt gattgtcata tagaacagaa tcgccgtgca     240
gtacgttgtg gacgaagcgg ctaaaactta cacaactcgc ccaaagcacc ctgcccgtcg     300
ggtcgctgag ggttaactta atagacacgg ctacgcatgt agtaccgaca gcagagtact     360
ggcggacgcg ggttcaactc ccgccagctc cacca                                 395
```

```
<210> SEQ ID NO 58
<211> LENGTH: 362
<212> TYPE: DNA
```

<213> ORGANISM: Borrelia afzelii

<400> SEQUENCE: 58

| ggggctgatt | ctggattcga | ctgaaaatgc | taatattgta | agttgcaagc | agagggaatc | 60 |
| tcttaaaact | tctaaaataa | atgcaaaaaa | taataacttt | acaagttcaa | accttgtaat | 120 |
| ggctgcttaa | gttagcagag | agttttgttg | aatttggctt | tgagattcac | ttatactctt | 180 |
| ttagacatcg | aagcttgctt | aaaaatgttt | tcaagttgat | ttttagggac | ttttatactt | 240 |
| gagagcaatt | tggcggtttg | ctagtatttc | caaccatat | tgcttagtaa | aatactagat | 300 |
| aagcttgtag | aagcttatag | tattgttttt | aggacgcggg | ttcaactccc | gccagtccac | 360 |
| ca | | | | | | 362 |

<210> SEQ ID NO 59
<211> LENGTH: 363
<212> TYPE: DNA
<213> ORGANISM: Borrelia crocidurae

<400> SEQUENCE: 59

| ggggctgatt | ctggattcga | ctaagaactt | tagtagcata | aatggcaagc | agagtgaatc | 60 |
| tcttaaaact | tctttaataa | atgcaaaaaa | taataacttt | acaagttcag | atcttgtaat | 120 |
| ggctgcttaa | tttagcagag | agttttgttg | gattttgctt | tgaggttcaa | cttatactct | 180 |
| ttaagacatc | aaagtatgcc | taaaaatgtt | tcaagttgat | ttttagggac | ctttaaactt | 240 |
| gagagtaatt | tggtggtttg | cttgttttcc | aagccttatt | gctttttcta | aaaattagct | 300 |
| aagcttgtag | atatttatga | tattattttt | aggacgcggg | ttcaactccc | gccagttcca | 360 |
| cca | | | | | | 363 |

<210> SEQ ID NO 60
<211> LENGTH: 365
<212> TYPE: DNA
<213> ORGANISM: Borrelia hermsii

<400> SEQUENCE: 60

| ggggctgatt | ctggattcga | ctaaaaactt | tagtagcata | aattgcaagc | agagggaatc | 60 |
| tcttaaaact | tctttaataa | atgcaagaaa | taataacttt | acaagttcaa | atcttgtaat | 120 |
| ggctgcttaa | attagcagag | agttctgctg | gattttgctt | tgaggttcag | cttatactct | 180 |
| tttaagacat | caaagcttgc | ttaaaaatat | ttcaagttga | ttttaggga | cttttaaatt | 240 |
| tgagagtaat | ttggcggttt | gctagttttt | ccaaacctta | ttacttaaag | aaaacactag | 300 |
| ctaagcttgt | agatatttat | gatattattt | taggacgcg | ggttcaactc | ccgccagctc | 360 |
| cacca | | | | | | 365 |

<210> SEQ ID NO 61
<211> LENGTH: 363
<212> TYPE: DNA
<213> ORGANISM: Borrelia garinii

<400> SEQUENCE: 61

| ggggctgatt | ctggattcga | ctgaaaatgc | gaatattgta | agttgcaggc | agagggaatc | 60 |
| tcttaaaact | tctaaaataa | atgcaaaaaa | taataacttt | acaagctcaa | accttgtaat | 120 |
| ggctgcttaa | gttagcaggg | agtttcgttg | aatttggctt | tgaggttcac | ttatactctt | 180 |
| ttcgatatcg | aagcttgctt | aaaaatgttt | tcaagttaat | ttttagggac | ttttgtactt | 240 |
| gagagcaatt | tggcggtttg | ctagtatttc | caaccatat | tgcttaagta | aaatgctaga | 300 |

```
taagcttgta gaagcttata atattgtttt taggacgcgg gttcaactcc cgccagtcca    360
cca                                                                  363

<210> SEQ ID NO 62
<211> LENGTH: 357
<212> TYPE: DNA
<213> ORGANISM: Thermodesulfobacterium commune

<400> SEQUENCE: 62
gggggcggaa aggattcgac ggggataggt aggattaaac agcaggccgt ggtcgcaccc    60
aaccacgtta aatagggtgc aaaaacacaa ctgccaacga atacgcctac gctttggcag   120
cctaagcgtg ctgccacgca cctttagacc ttgcctgtgg gtctaaaggt gtgtgaccta   180
acaggctttg ggaggcttaa tcggtggggt taagcctccc gagattacat cccacctggt   240
agggttgctt ggtgcctgtg acaagcaccc tacgagattt cccacaggc taagcctgta    300 gcggtttaat ctgaactatc tccggacgcg ggttcgattc ccgccgcctc cccacca      357

<210> SEQ ID NO 63
<211> LENGTH: 358
<212> TYPE: DNA
<213> ORGANISM: Thermotoga neapolitana
<220> FEATURE:
<221> NAME/KEY: misc_feature
<222> LOCATION: (1)..(358)
<223> OTHER INFORMATION: n is an unknown base

<400> SEQUENCE: 63
gggggcggaa aggattcgac ggggatggag tccctggga agcgagccga ggtccccacc    60
tcctcgtaaa aaaggtggga acacgaataa gtgccaacga acctgttgct gttgccgcct   120
aatagatagg cggccgtcct ctccggagtt ggctgggctc cggaagaggg cgtgagggat   180
ccagcctacc gatctgggct ccgccttccg gcccggatcg ggaaggttca ggaaggctgt   240
gggaagcgac accctgcccg tgggggtcc ttcccgagac acgaaacacg gctgcgctc    300 ggagaagccc aggggcctcc atcttcngac gcgggttcga ttcccgccac ctccacca    358

<210> SEQ ID NO 64
<211> LENGTH: 347
<212> TYPE: DNA
<213> ORGANISM: Deinococcus proteolyticus

<400> SEQUENCE: 64
gggggcggaa aggattcgac gggggaacgg aaagcgctgc tgcgtgccga ggagccgttg    60
gcctcgtaaa caaacggcaa agccattaac tggcgaaaat aactacgctc tcgctgctta   120
agtgagacag tgaccacgta gccccgcctt tggcgacgtg tgaactgaga caaaagaagg   180
ctagcttagg tgaggttcca tagccaaaag tgaaaccaaa tggaaataag gcggacggca   240
gcctgtttgc tggcagccca ggcccgacaa tttaagagca gactacgcac gtagatgcac   300
gctggatgga cctttggacg cgggttcgat tcccgccagc tccacca                347

<210> SEQ ID NO 65
<211> LENGTH: 352
<212> TYPE: DNA
<213> ORGANISM: Prosthecobacter fusiformis

<400> SEQUENCE: 65
ggggctgatt ctggattcga cggggagtac aaggatcaaa agctgcaagc cgaggtgccg    60
```

-continued

```
ttacctcgta aaacaacggc aaaaaagaag tgccaacaca aatttagcat tagctgctta    120
atttagcagc tacgctcttc taacccgggc tggcagggtt agaagggtgt cataatgagc    180
cagctgcccc ttccgactcc cctaaggaag ggaaagatgt aggggatagg tgcttacaga    240
atcctgcggg agggagtctg taagtgccga aaagttaaaa ctcccgctaa gcttgtagag    300
gcttttgatt cttgctctct ggacgcgggt tcaactcccg ccagctccac ca            352
```

<210> SEQ ID NO 66
<211> LENGTH: 329
<212> TYPE: DNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 66

```
gggnnnnatt tggaattcgc cgaatgctag aagtggaggc tgcatgccgc ggatgattcg    60
ttggccgctt taccaattcg gatcaaacaa ctaaatgcgg actctaacga gcttgccctc    120
gccgcttaat tgacggtgac gttcctccag tgaagtctgt gaattggagg agcgactact    180
tacaggctgg ccaaaagagc gggcgaccgg ccccaaggcg agatctacag gccgctggat    240
ggacggcatc ctggcagtag gaggctggac atcgagatca aatnattgcc tgagcatgga    300
gacgctttca taaaggngtt cggacaggg                                      329
```

<210> SEQ ID NO 67
<211> LENGTH: 318
<212> TYPE: RNA
<213> ORGANISM: Thermoanaerobacterium saccharolyticum

<400> SEQUENCE: 67

```
cgggggutagu agagguaaaa guagcgagcc gagguuccau cugcucguaa aacgguggac    60
uuaaauauaa acgcaaacga uaauuuagcu uacgcugcuu aauuacaagc agccguucaa    120
ccuuugauuc ccacaucaaa ggauggggcg ucgauuuagu ggggaacuga uuuaucaaag    180
cuuugagaua aaucggauuu uaugaagcua ccaaagcagu uauccuguca cugggagaac    240
ugcagaggga augucaaaac agugacugcg cucggagaag cuuuuacugu gacaccuucg    300
gaccgggguu caacucccc                                                 318
```

<210> SEQ ID NO 68
<211> LENGTH: 187
<212> TYPE: RNA
<213> ORGANISM: Clostridium acetobutylicum

<400> SEQUENCE: 68

```
aaucuggcgu cgagagcggg gaaacgagcc uuacaaagcu uugaguaagg aacggaauuu    60
augaagcuac ugaagugaaa agcuuguuug uaggcguuuc auggagggaa uguuaaaaua    120
caaacugcac ucggagaugc uuaaaugaaa ccauuuucgg acaggguuc gauuccccuc    180 gccucca                                                              187
```

<210> SEQ ID NO 69
<211> LENGTH: 335
<212> TYPE: RNA
<213> ORGANISM: Clostridium stercorarium

<400> SEQUENCE: 69

```
cgggguuauu gaagcaagag uagcgggguag aggauucucg uuggccucuu uaaaaaacga    60
```

-continued gagcuaaaaa uaaacgcaaa caacgauaac uacgcuuuag cugcugcgua aguaacacgc 120
agcccgucgg ccccggguu ccugcgccuc gggauaccgg cgucaucaag gcagggaacc 180
agccggauca ggcuucaggu ccggugggau uuaaugaagc uaccgacuua uaaagccugu 240
cucugggcgu uauaagaagg gaaugucaaa acagagacac caaugcaccc ggagaagcuc 300
uuguggauau gguuccggac acgaguucga uuccc 335

<210> SEQ ID NO 70
<211> LENGTH: 336
<212> TYPE: RNA
<213> ORGANISM: Clostridium perfringens

<400> SEQUENCE: 70 cgggggguaag augggguuuga uaagcgaguc gagggaagca uggugccucg auaauaaagu 60
augcauuaaa gauaaacgca gaagauaauu uugcauuagc agcuuaauuu agcgcugcuc 120
auccuuccuc aauugcccac gguugagagu aagggguguca uuuaaaagug gggaaccgag 180
ccuagcaaag cuuugagcua ggaacggaau uuaugaagcu uagaggaagu uugucugugg 240
acguucucug agggaauuuu aaaacacaag acacuaaaau cuaguacacu cguagaaagu 300
cuuacugguc ugcuuucgga cacggguuca acuccc 336

<210> SEQ ID NO 71
<211> LENGTH: 305
<212> TYPE: RNA
<213> ORGANISM: Clostridium lentocellum

<400> SEQUENCE: 71 cggggggucac aucuacuggg gcagccaucc guagaacgcc ggagucuacg uuaaaagcug 60
gcacuuaaag uaaacgcuga agauaauuua gcaaucgcug ccuaauuaag gcgcaguccu 120
ccuaggucuu ccgcagccua gaucagggcu ucgacucgcg gauccuucac cuggcaaagc 180
uuugagccaa cgugaacacu augaagcuag ccugucuuug ggcgcuagau ggagggaaug 240
ucaaaacaaa gaauaugaug guagagacca cgcuauaugg gcuuucggac aggggguucga 300 uuccc 305

<210> SEQ ID NO 72
<211> LENGTH: 319
<212> TYPE: RNA
<213> ORGANISM: Heliobacillus mobilis

<400> SEQUENCE: 72
cggggaacgu guuugcuugg gaugcgagcc ggguugccgc caggaccgua aaaagggcgg 60
aaggcuuuaa uugccgaaga uaacuacgcu uuagcugcuu uauugcaguc uaaccucuuc 120
uccucugugc ucucggugag gauguaaggg gucauuuaag agagcuggcu ucgaccaauu 180
cucggagguc caagcgagau uuaucgagau agccugacca acgcucuguc ugccgugcgg 240
aaggaaggcg aaaucuaaaa cgacagauac gcucguagug uccuuugugg gcauuucuuc 300
ggacgcgggu ucaacuccc 319

<210> SEQ ID NO 73
<211> LENGTH: 321
<212> TYPE: RNA
<213> ORGANISM: Heliospirillum gestii

<400> SEQUENCE: 73

```
cggggaacgu guuugcuuag gacgcgagcc ggguugccgc caggaccgua aaaagggcgg    60
aaggcuuuaa uugccgaaga uaacuacgcu uuagcugcuu aauugcaguc uaccucuuc   120 uccucugugc ucucggugag gauguaaggg gucauuuaag agagcuggcu cgaaccaauu   180
cucggagguu cgguaagac uuaucgagau cagccugacc aacgcucugu cugccgugcg   240
gaaggauggc gaaaucuaaa acgacagaau acgcucguag uguccuuugu gggcauuucu   300
ucggacgcgg guucaacucc c                                             321

<210> SEQ ID NO 74
<211> LENGTH: 325
<212> TYPE: RNA
<213> ORGANISM: Brevibacillus brevis

<400> SEQUENCE: 74
cggggauggu agagcaugag aagcgagccg ggggguugcg gaccucguca ccaacgcaaa    60
cgccauuaac uggcaacaaa caacuuucuc ucgcugcuua auaaccagug aggcucuccc   120
acugcaucgg cccgugugcc guggauaggg cucaacuuua cgggcuacg ccggaggcuu   180 ccgccuggag ccaaaggaag aagaccaauc aggcuaggug ccaggucagc gcgucacucc   240
gcgaaucugu caccgaaacu cuaaacgagu gacugcgcuc ggagaugcuc auguaucgcu   300 guuucggac ggggguucga uuccc                                          325

<210> SEQ ID NO 75
<211> LENGTH: 360
<212> TYPE: RNA
<213> ORGANISM: Bacillus subtilis

<400> SEQUENCE: 75
ggggacguua cggauucgac agggauggau cgagcuugag cugcgagccg agaggcgauc    60
ucguaaacac gcacuuaaau auaacuggca aaacuaacag uuuuaaccaa aacguagcau   120
uagcugccua auaagcgcag cgagcucuuc cugacauugc cuauguqucu gugaagagca   180 cauccaagua ggcuacgcuu gcguucccgu cugagaacgu aagaagagau gaacagacua   240
gcucucggaa ggcccgcccg caggcaagaa gaugagugaa accauaaaua ugcaggcuac   300
gcucguagac gcuuaaguaa ucgauguuuc uggacguggg uucgacuccc accgucucca   360

<210> SEQ ID NO 76
<211> LENGTH: 325
<212> TYPE: RNA
<213> ORGANISM: Bacillus badius

<400> SEQUENCE: 76
cagggauagu ucgagcuugg gcugcgagcc ggagggccgu cuucguacca acgcaaacgc    60
cuaaauauaa cuggcaaaaa agauuuagcu uuagcugccu aauauagguu cagcugcucc   120
ucccgcuauc guccauguag ucggguaagg gguccaaacu uaguggacua cgccggaguu   180
cuccgccugg ggacaaagga agagaucaau caggcuagcu gcccggacgc ccgucgauag   240
gcaaaaggaa cagugaaccc caaauauauc gacuacgcuc guagacguuc aaguggcguu   300
aucuuuggac gugggguucaa cuccc                                        325

<210> SEQ ID NO 77
<211> LENGTH: 341
<212> TYPE: RNA
<213> ORGANISM: Bacillus megaterium

<400> SEQUENCE: 77
```

```
ggggacguua cggauucgac aggguaguuc gagcuuaggu ugcgagucga ggagauggcc    60
ucguuaaaac aucaacgcca auaauaacug gcaaaucuaa caauaacuuc gcuuuagcug   120
cauaauagua gcuuagcguu ccucccucca ucgcccaugu gguaggguaa gggacucacu   180
uuaagugggc uacgccggag uucgccgucu gaggacgaag aagagaauaa ucagacuag    240 cgacugggac gccuguuggu aagcagaaca gcucgcgaau gaucaauaug ccaacagccg   300
uacacucgua gacgcuuaag uggccauauu ucggacgug g                       341
```

<210> SEQ ID NO 78
<211> LENGTH: 315
<212> TYPE: RNA
<213> ORGANISM: Bacillus thermoleovorans

<400> SEQUENCE: 78

```
cgggggguagg ucgagcuuaa gcggcgagcc gaggggacg uccucguaaa aacgucaccu    60
aaagauaacu ggcaaacaaa acuacgcuuu agcugccuaa uugcugcagc uagcuccucc   120
cgccaucgcc cgcguggcgu ucgaggggcu cauauggagc gggcuacgcc caaauccgcc   180
gccugaggau gagggaagag acgaaucagg cuccggagg ccugucggua ggcggaacgg    240
acggcgaagc gaaauauacc gacuacgcuc guagaugcuu aaguggcgau gccucuggac   300
guggguucga uuccc                                                   315
```

<210> SEQ ID NO 79
<211> LENGTH: 335
<212> TYPE: RNA
<213> ORGANISM: Enterococcus faecium

<400> SEQUENCE: 79

```
caggcacagu uugagcuuga auugcguuuc guagguuacg ucuacguuaa acguuacag     60 uuaaauauaa cugcuaaaaa cgaaaacaac ucuuacgcuu uagcugccua aaaacaguua   120
gcguagaucc ucucggcauc gcccaugugc ucgaguaagg gucucaaauu uaguggaua    180 cgugacaacu uuccgucugu aaguuguaa agagaucauc agacuagcga uacagaaugc    240
cugucacucg gcaagcugua aagcgaaacc acaaaugagu ugauaugaac guagauuuuu   300
aaguggcgau guguuuggac gcgggguucaa cuccc                             335
```

<210> SEQ ID NO 80
<211> LENGTH: 364
<212> TYPE: RNA
<213> ORGANISM: Enterococcus faecalis

<400> SEQUENCE: 80

```
ggggggcguua cggauucgac aggcauaguu gagcuugaau ugcguuucgu agguuacggc    60
uacguuaaaa cguuacaguu aaauauaacu gcuaaaaacg aaaacaauuc uuucgcuuua   120
gcugccuaaa aaccagcuag cgaagauccu cccggcaucg cccaugugcu cgggucaggg   180
uccuaaucga aguggggauac gcuaaauuuu uccgucugua aauuuagag gagcuuacca    240 gacucagcaa uacagaaugc cugucacucg gcacgcugua aagcgaaccu uuaaaugagu   300
guuaugaacg uagagauuua aguggcaaua uguuuggacg cggguucgac ucccgccguc   360
ucca                                                              364
```

<210> SEQ ID NO 81
<211> LENGTH: 346
<212> TYPE: RNA

<213> ORGANISM: Streptococcus pyogenes

<400> SEQUENCE: 81

| | | | | | |
|---|---|---|---|---|---|
| gggguuguua | cggauucgac | aggcauuaug | aggcauguuu | ugcgucccau | cggcagaugu | 60 |
| aaauugccag | uuaaauauaa | cugcaaaaaa | uacaaacucu | uacgcuuuag | cugccuaaaa | 120 |
| accagcuagc | gugacuucua | caagauugcu | uguguccugu | uagaagucuc | aaaauagcaa | 180 |
| gcuacgguua | cgaaauuguc | uaguuucgug | acaagagauu | gauagacccc | gcaaacuaau | 240 |
| ggcuugaguu | augugucuuu | aguuuguuaa | augaagacau | aaccuaugga | cguagacaaa | 300 |
| uauguuggca | gguguuugga | cgugggucg | acucccacca | gcucca | | 346 |

<210> SEQ ID NO 82
<211> LENGTH: 344
<212> TYPE: RNA
<213> ORGANISM: Streptococcus pneumoniae

<400> SEQUENCE: 82

| | | | | | |
|---|---|---|---|---|---|
| gggggucguua | cggauucgac | aggcauuaug | aggcauauuu | ugcgacucgu | guggcgacgu | 60 |
| aaacgcucag | uuaaauauaa | cugcaaaaaa | uaacacuucu | uacgcucuag | cugccuaaaa | 120 |
| accagcaggc | gugacccgau | uuggauugcu | cguguucaau | gacaggucuu | auuauuagcg | 180 |
| agauacgauu | aagccuuguc | uagcgguuug | auaagagauu | gauagacucg | caguuucuag | 240 |
| acuugaguua | ugugucgagg | ggcuguuaaa | auaauacaua | acuaugguug | uagacaaaua | 300 |
| uguuggcagg | uguuuggacg | uggguucgac | ucccaccggc | ucca | | 344 |

<210> SEQ ID NO 83
<211> LENGTH: 364
<212> TYPE: RNA
<213> ORGANISM: Streptococcus gordonii

<400> SEQUENCE: 83

| | | | | | |
|---|---|---|---|---|---|
| gggggucguua | cggauucgac | aggcauuaug | aggcauauuu | ugcgacucau | cuagcggaug | 60 |
| uaaaacgcca | guuaaauaua | acugcaaaaaa | auaaauacuuc | uuacgcuuua | gcugccuaaa | 120 |
| aaccagcggg | cgugacccga | uucggauugc | uuguguucuga | ugacaggucu | uauuauuagc | 180 |
| aagcuacggu | agaaucuugu | cuagugauuu | uacaagagau | ugauagacua | cguuagaacu | 240 |
| gagucagccg | cuugauuugg | gcuugaguua | ugugucaaaa | ucaaguuaaa | acaauacaua | 300 |
| gcuauguuug | uagacaaaua | uguuggcaga | guuuggacg | uggguucgac | ucccaccggc | 360 |
| ucca | | | | | | 364 |

<210> SEQ ID NO 84
<211> LENGTH: 329
<212> TYPE: RNA
<213> ORGANISM: Streptococcus mutans

<400> SEQUENCE: 84

| | | | | | |
|---|---|---|---|---|---|
| gggggucguua | cggauucgac | aggcauuaug | agaccuauuu | ugcgacucau | cuagcggaug | 60 |
| uaaaacgcca | guuaaauaua | acugcaaaaaa | auacaaauuc | uuacgcagua | gcugccuaaa | 120 |
| aaccagccug | ugugaucaau | aacaaauugc | uuguguuugu | ugauuggucu | uauuguuaac | 180 |
| aagcugcugu | ucuaaaagag | uucuacgac | uccgcaucgu | uagaguuuga | guuauguauu | 240 |
| guaacggugu | uaaauaaaca | cauaaccuau | aguuguagac | aaaugggguua | gcagauguuu | 300 |
| ggacguggg | ucgaucccca | ccggcucca | | | | 329 |

<210> SEQ ID NO 85
<211> LENGTH: 328
<212> TYPE: RNA
<213> ORGANISM: Staphylococcus epidermidis

<400> SEQUENCE: 85

```
cagggguccc cgagcuuauu aagcgugucg gaggguuggc uccgucauca acacauuucg    60
guuaaauaua acugacaaau caaacaauaa uuucgcagua gcugcguaau agccacugca   120
ucgccuaaca gcaucuccua cgugcuguua acgcgauuca acccuaguag gauaugcuaa   180
acacugccgc uugaagucug uuuagaugaa auauaaucaa gcaguauca uguugguugu   240
uuauugcuua gcaugaugcg aaaauuauca auaaacuaca cacguagaaa gauuuguauc   300
aggaccucug gacgcggguu caacuccc                                      328
```

<210> SEQ ID NO 86
<211> LENGTH: 359
<212> TYPE: RNA
<213> ORGANISM: Staphylococcus aureus

<400> SEQUENCE: 86

```
ggggacguuc auggauucga caggggcccc cgagcucau uaagcgugc ggaggguugu     60
cuucgucauc aacacacaca guuuauaaua acuggcaaau caaacaauaa uuucgcagua   120
gcugccuaau cgcacucugc aucgccuaac agcauuuccu augugcuguu aacgcgauuc   180
aaccuuaaua ggauaugcua aacacugccg uugaagucu guuuagaaga aacuuaauca   240
aacuagcauc auguugguug uuuaucacuu ucaugaugc gaaaccuauc gauaaacuac   300
acacguagaa agauguguau caggaccuuu ggacgcgggu ucaaucccg ccgucucca    359
```

<210> SEQ ID NO 87
<211> LENGTH: 334
<212> TYPE: RNA
<213> ORGANISM: Lactobacillus acidophilus

<400> SEQUENCE: 87

```
caggcguaga cccgcauuga cugcgguucg uagguuacgu cuacguaaaa acguuacagu    60
uaaauauaac ugcaaauaac aaaaauucuu acgcauuagc ugcuuaauuu agcgcaugcg   120
uugcucuuug ucgguuuacu cguggcugac acugaguauc aacuuagcga guuacguuua   180
acuaccucac cugaauaguu gaaaagaguc uuagcagguu agcuaguccca uacuagcccu   240
guuauauggc guuuuggacu agugaaguuc aaguaauaua acaugaucg uagaggucag   300
ugacgagaug cguuuggaca gggguucaac uccc                               334
```

<210> SEQ ID NO 88
<211> LENGTH: 347
<212> TYPE: RNA
<213> ORGANISM: Aquifex aeolicus

<400> SEQUENCE: 88

```
gggggcggaa aggauucgac ggggacaggc gguccccgag gagcaggccg gguggcuccc    60
guaacagccg cuaaaacagc ucccgaagcu gaacucgcuc ucgcugccua auuaaacggc   120
agcgcgucccc cgguagguuu gcgguggcc uaccggaggg cgucagagac acccgcucgg   180
gcuacucggu cgcacgggggc ugaguagcug acaccuaacc cgugcuaccc ucggggagcu   240
ugcccguggg cgaccccgagg ggaaauuccg aacacgggcu aagccuguag agccucggau   300
guggccgccg uccucggacg cggguucgau ucccgccgcc uccacca                 347
```

<210> SEQ ID NO 89
<211> LENGTH: 355
<212> TYPE: RNA
<213> ORGANISM: Thermotoga maritima

<400> SEQUENCE: 89

| | | | | | | |
|---|---|---|---|---|---|---|
| gggggcgaac | gguuucgacg | gggauggagu | ccccugggaa | gcgagccgag | guccccaccu | 60 |
| ccucguaaaa | aaggugggac | aaagaauaag | ugccaacgaa | ccuguugcug | uugccgcuua | 120 |
| auagauaagc | ggccguccuc | uccgaaguug | gcugggcuuc | ggaagagggc | gugagagauc | 180 |
| cagccuaccg | auucaguucg | ccuuccggcc | ugaaucggga | aaacucagga | aggcuguggg | 240 |
| agaggacacc | cugcccgugg | gagguccccuc | ccgagagcga | aaacacgggc | ugcgcucgga | 300 |
| gaagcccagg | ggccuccauc | uucggacggg | gguucgaauc | cccccgccuc | cacca | 355 |

<210> SEQ ID NO 90
<211> LENGTH: 355
<212> TYPE: RNA
<213> ORGANISM: Thermotoga neapolitana

<400> SEQUENCE: 90

| | | | | | | |
|---|---|---|---|---|---|---|
| ggggcggaa | aggauucgac | ggggauggag | uccccuggga | agcgagccga | gguccccacc | 60 |
| uccucguaaa | aaggguggga | acacgaauaa | gugccaacga | accguugcu | guugccgccu | 120 |
| aauagauagg | cggccguccu | cuccggaguu | ggcugggcuc | cggaagaggg | cgugagggau | 180 |
| ccagccuacc | gaucugggcu | ccgccuuccg | gcccggaucg | ggaagguuca | ggaaggcugu | 240 |
| gggaagcgac | acccugcccg | uggggggucc | uucccgagac | acgaaacacg | ggcugcgcuc | 300 |
| ggagaagccc | aggggccucc | aucuucggac | ggggguucga | uucccgccgc | cucca | 355 |

<210> SEQ ID NO 91
<211> LENGTH: 350
<212> TYPE: RNA
<213> ORGANISM: Thermus thermophilus

<400> SEQUENCE: 91

| | | | | | | |
|---|---|---|---|---|---|---|
| gggggugaaa | cggucucgac | ggggucgcc | gagggcgugg | cugcgcgccg | aggugcgggu | 60 |
| ggccucguaa | aaacccgcaa | cggcauaacu | gccaacacca | acuacgcucu | cgcggcuuaa | 120 |
| ugaccgcgac | cucgcccggu | agcccugccg | ggggcucacc | ggaagcgggg | acacaaaccc | 180 |
| ggcuagcccg | ggccacgcc | cucuaacccc | gggcgaagcu | ugaaggggc | ucgcuccugg | 240 |
| ccgcccgucc | gcgggccaag | ccaggaggac | acgcgaaacg | cggacuacgc | gcguagaggc | 300 |
| cacgccccgg | cgaccuucgg | acggggguuc | gauucccccc | accuccacca | | 350 |

<210> SEQ ID NO 92
<211> LENGTH: 349
<212> TYPE: RNA
<213> ORGANISM: Deinococcus radiodurans

<400> SEQUENCE: 92

| | | | | | | |
|---|---|---|---|---|---|---|
| gggggugacc | cgguuucgac | aggggaacug | aaggugaugu | ugcgugucga | ggugccguug | 60 |
| gccucguaaa | caaacggcaa | agccauuuaa | cuggcaacca | gaacuacgcu | cucgcugcuu | 120 |
| aagugagaug | acgaccgugc | agcccggccu | uggcgucgc | ggaagucacu | aaaaaagaag | 180 |
| gcuagcccag | gcgauucucc | auagccgacg | gcgaaacuuu | auggagcuac | ggccugcgag | 240 |
| aaccugccca | cuggugagcg | ccggcccgac | aaucaaacag | ugggauacac | acguagacgc | 300 |
| acgcuggacg | gaccuuugga | cggcgguucg | acuccgccca | ccuccacca | | 349 |

<210> SEQ ID NO 93
<211> LENGTH: 347
<212> TYPE: RNA
<213> ORGANISM: Deinococcus proteolyticus

<400> SEQUENCE: 93

| | | | | | |
|---|---|---|---|---|---|
| gggggcggaa | aggauucgac | gggggaacgg | aaagcgcugc | ugcgugccga | ggagccguug | 60 |
| gccucguaaa | caaacggcaa | agccauuaac | uggcgaaaau | aacuacgcuc | ucgcugcuua | 120 |
| agugagagca | gugaccacgu | agccccgccu | uggcgacgu | gugaacugag | acaaaagaag | 180 |
| gcuagcuuag | gugagguucc | auagccaaaa | gugaaaccaa | auggaaauaa | ggcggacggc | 240 |
| agccuguuug | cuggcagccc | aggcccgaca | auuuaagagc | agacuacgca | cguagaugca | 300 |
| cgcuggaugg | accuuuggac | ggcgguucga | uucccgccgc | cucacca | | 347 |

<210> SEQ ID NO 94
<211> LENGTH: 334
<212> TYPE: RNA
<213> ORGANISM: Thermomicrobium roseum

<400> SEQUENCE: 94

| | | | | | |
|---|---|---|---|---|---|
| cagggccgua | ggugcgagga | uugcaggucg | aggucgccca | cgaacucgua | aaaaggggca | 60 |
| ccaaguaacu | ggcgagcgcg | aacucgcucu | ggcugcguaa | uucacgcagc | cacgucugcc | 120 |
| cggacccuuc | ccugguggu | ucggagcggg | cgccgcaaga | ccggggugcc | ccuggcccaa | 180 |
| gcgccggugc | gggccagguc | aagcgugauc | cggcucggcu | gaccgggauc | cugucggugg | 240 |
| gagccuggca | gcgacaguag | aacaccgacu | aagccuguag | cauauccucg | gcugaacgcu | 300 |
| cuggacgggg | guucaacucc | cgccagcucc | acca | | | 334 |

<210> SEQ ID NO 95
<211> LENGTH: 353
<212> TYPE: RNA
<213> ORGANISM: Coprothermobacter proteolyticus

<400> SEQUENCE: 95

| | | | | | |
|---|---|---|---|---|---|
| gggggcggaa | aggauucgac | ggggagucgg | agccuugagc | ugcaggcagg | guuggcugcc | 60 |
| acaccuuaaa | aagguagca | aggcaaaaau | aaaugccgaa | ccagaauuug | cacuagcugc | 120 |
| uuaauguaag | cagccgcucu | ccaaacugag | gcugcauaag | uuuggaagag | cgucaaccca | 180 |
| ugcagcggcu | cuuaagcagu | ggcaccagcu | guuuaagggu | gaaagagug | gugcugggca | 240 |
| gugcgguugg | gcuuccuggg | cugcacuguc | gagacuucac | aggagggcua | agccuguaga | 300 |
| cgcgaaaggu | ggcggcucgu | cggacgcggg | uucgauuccc | gccgccucca | cca | 353 |

<210> SEQ ID NO 96
<211> LENGTH: 360
<212> TYPE: RNA
<213> ORGANISM: Herpetosiphon aurantiacus

<400> SEQUENCE: 96

| | | | | | |
|---|---|---|---|---|---|
| gggggcggaa | aggauucgac | ggggagggcc | aaucguaagu | ggcaagccga | gacgcugagc | 60 |
| cucguuaaau | cggcaacgcc | auuaacuggc | aaaaacacuu | uccgcgcucc | uguagcgcuu | 120 |
| gcugccuaau | uaaggcaaca | cgucucuacu | agccucagcc | cgaugggcuu | guagcggcga | 180 |
| cacuuagucg | ggucgcuccc | cuaguuaugu | cugugggcua | gggcuaaga | uuaacaggcu | 240 |
| ggucgguggcc | cgcuuugucu | aucgggugu | gcaccgauaa | gauuuaauca | auagacuacg | 300 |

```
cuuguagaug cuugcgguuu aacuuuuugg acgcgggulc gauucccgcc gccuccacca    360
```

<210> SEQ ID NO 97
<211> LENGTH: 355
<212> TYPE: RNA
<213> ORGANISM: Thermodesulfobacterium commune

<400> SEQUENCE: 97

```
gggggcggaa aggauucgac ggggauaggu aggauuaaac agcaggccgu ggucgcaccc     60
aaccacguua aauagggugc aaaaacacaa cugccaacga auacgccuac gcuuggcag    120
ccuaagcgug cugccacgca ccuuuagacc uugccuguqg gucuaaaggu gugugaccua   180
acaggcuuug ggaggcuuaa ucggugqggu uaagccuccc gagauuacau cccaccuggu   240
aggguugcuu ggugccugug acaagcaccc uacgagauuu ucccacaggc uaagccugua   300
gcgguuuaau cugaacuauc uccggacgcg gguucgauuc ccgccgccuc cacca        355
```

<210> SEQ ID NO 98
<211> LENGTH: 329
<212> TYPE: RNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 98

```
gggnnnnauu uggaauucgc cgaaugcuag aaguggaggc ugcaugccgc ggaugauucg     60
uuggccgcuu uaccaauucg gaucaaacaa cuaaaugcgg acucuaacga gcuugcccuc   120
gccgcuuaau ugacggugac guuccuccag ugaagucugu gaauuggagg agcgacuacu   180
uacaggcugg ccaaaagagc gggcgaccgg ccccaaggcg agaucuacag gccgcuggau   240
ggacggcauc cuggcaguag gaggcuggac aucgagauca aaunauugcc ugagcaugga   300
gacgcuuuca uaaaggnguu cggacaggg                                    329
```

<210> SEQ ID NO 99
<211> LENGTH: 351
<212> TYPE: RNA
<213> ORGANISM: Dictyoglomus thermophilum

<400> SEQUENCE: 99

```
gggggcggaa aggauucgac ggggaguaca aggaucaaaa gcugcaagcc gaggugccgu     60
uaccucguaa aacaacggca aaaagaagu gccaacacaa auuuagcauu agcugcuuaa    120
uuuagcagcu acgcucuucu aacccgggcu ggcagggquua gaaggguguc auaaugagcc   180
agcugcccu uccgacuccc cuaaggaagg gaaagaugua ggggauaggu gcuuacagaa   240
uccugcggga gggagucugu aagugccgaa aaguuaaaac ucccgcuaag cuuguagagg   300
cuuuugauuc uugcucucug gacgcggguu cgauucccgc cgccuccacc a           351
```

<210> SEQ ID NO 100
<211> LENGTH: 399
<212> TYPE: RNA
<213> ORGANISM: Synechocystis sp. PCC 6803

<400> SEQUENCE: 100

```
ggggccgcaa ugguuucgac agguuggcga aagcuugccc gugauacagg ucgagaguga     60
gucccucuc gcaaaucaaa ggcucaaaaa aaaguaacug cgaauaacau cgucagcuuc    120
aaacggguag ccauagcagc cuagucugua aaagcuacau uuucuugca aagaccguuu    180
```

-continued

```
acuucuuuuc ugacuccguu aaggauuaga gguuaacccc aacggaugcu uuguuuggcu    240
cuucucuagu uagcuaaaca aucaagacuc agacuagagc aucccaccau cagggauaau    300
cgaugguccc cguccaggg cuagaaggac uaaaccugug aaugagcgga aaguuaauac    360
ccaguuugga cagcaguuca auucugcucg gcuccacca                          399

<210> SEQ ID NO 101
<211> LENGTH: 385
<212> TYPE: RNA
<213> ORGANISM: Nostoc muscorum

<400> SEQUENCE: 101
ggguccgucg guuucgacag guuggcgaac gcuacucugu gauucagguc gagagugagu     60
cuccucugca aaucaaggcu caaaacaaaa guaaaugcga auaacaucgu uaaauuugcu    120
cguaaggacg cucuaguagc ugccuaaaua gccucuuuca gguucgagcg cuuucgguuu    180
gacuccguua aggacugaag accaacccccc aacggaugcu cuagcaaugu ucucggguug    240
gcuugcuagc uaagauuuaa ucagagcauc cuacguucgg gauaaugaac gauucccgcc    300
uugaggguca gaaaggcuaa accugugaau gagcgggggg ucaauaccca auuggacag    360 caguucgacu cugcucgauc cacca                                          385

<210> SEQ ID NO 102
<211> LENGTH: 393
<212> TYPE: RNA
<213> ORGANISM: Synechococcus PCC 6301

<400> SEQUENCE: 102
ggggcuguaa ugguuucgac guuggguga auccuucacc gugauucagg ccgagaggga     60
guccacucuc guaaauccag gcucaaccaa aaguaacugc gaacaacauc guuccuuucg    120
cucguaaggc ugcccugua gcugcuuaaa cgccacaaac uuucuggcuc gagcgucuag    180
ucguagacuc cguuaauacg ccuagacuua aaccccccaac ggaugcugag uggcggccuc    240
aggccguucc ucucgcuaag caaaaaccug agcaucccgc caacggggau aaucguuggc    300
ucccgcacag uggggucaacc gugcuaagcc ugugaacgag cggaaaguua cuagucaaug    360
cggacagcgg uucgauuccg cucagcucca cca                                 393

<210> SEQ ID NO 103
<211> LENGTH: 312
<212> TYPE: RNA
<213> ORGANISM: Leptolyngbya sp. (ATCC 27894)

<400> SEQUENCE: 103
ggcucaaaaa aauagaugca aacaacaucg uaccuuucgc ucguaaaacu gcaccuguug     60
cagcauaaaa caccucuaau ucagguucga gcgcuuaccg ucugacaccg uuaaagauag    120
uaagcacaac cccaacgguu gcucuagaau uucgccuuug gucggcauuc uagcuaagac    180
aauaccaaag cauccuauug uccgggacaa aggacaguuc ccgcuucgag gauuagagaa    240
gcuaaaccug ugaaugauug auagagcuaa uaccccaguuu ggacacgggu caacucccg     300 ccagcuccac ca                                                        312

<210> SEQ ID NO 104
<211> LENGTH: 323
<212> TYPE: RNA
<213> ORGANISM: Porphyra purpurea
```

<400> SEQUENCE: 104

```
gggcugcaa gguuucuaca uugugaaaaa acaaauauau gaaaguaaaa cgagcucauu     60
auuagagcuu uuaguuaaau aaaugcagaa aauaauauua uugcuuuuuc ucgaaaauua   120
gcuguugcau aaauagucuc aauuuugua auucgaagug auagacucuu auacacuacg    180
aauauucugu uagaguugcu cuuaauaaaa gaaaaguaaa aaaauacaaa uccuuauguu    240
uuuuaccuga auugauucaa uuuaagguua guauuuuug auuuuacaa uggacgugggg    300
uucaagucccc accagcucca cca                                         323
```

<210> SEQ ID NO 105
<211> LENGTH: 294
<212> TYPE: RNA
<213> ORGANISM: Cyanophora paradoxa

<400> SEQUENCE: 105

```
ggggcuguuu agguucgac guuuuuucu aauuauguuu guuaagcaag ucgaggauuu     60
guucuaucuc gaaaucaag aacucucaaa auuuaaacgc aacuaauauu guacguuuua   120
accguaaagc agcuucgcu guuuaauaau acuuuuaau uuaaaaaccu aauuuuuuua   180
ggaauuuauu uauuuaugu uuauccgcu uaaugaauua aaaaaagcua acuugugaa    240
uaaacgcaua auuuaaaaaa acggacgugg guucaaauccc accagcuccc acca      294
```

<210> SEQ ID NO 106
<211> LENGTH: 371
<212> TYPE: RNA
<213> ORGANISM: Odontella sinensis

<400> SEQUENCE: 106

```
ggggcugacu ugguuucgac auuuaaaaau uguuacagua ugaugcaggu cgaaguuucu    60
aaucuucgua aaaaaagaga aauuuauaau aaaugcuaau aauuuaauuu cuucuguguu   120
uaaaaguuua ucaacuaagc aaaauagguu aaauuuaagu uuugcuguuu aaguuuuaug   180
cacauuuaau gaucuaguaa auaacuuugu ucgcuauaau uuauauuuau aacuagacuu   240
uugucuuuuu uauaguuuag aauaacuuua ucauucaaa cccgguucca ucaguugaa    300
cuaaaccugu gaacgaauac uauaauaaaa uuuuuagaug gacgugggu cgacucccau   360
cagcuccacc a                                                     371
```

<210> SEQ ID NO 107
<211> LENGTH: 348
<212> TYPE: RNA
<213> ORGANISM: Thls. weiss*

<400> SEQUENCE: 107

```
ggggcugauu ugguucgac auuuaaaacu ucuuucuaug ugucagguca aaguuuguau    60
ucuuuguaaa aaaauacuaa aauacuaaua aaugcuaaua auauauacc guuuauuuu    120
aaagcaguaa aaacaaaaaa agaagcaaug gcuuuaaauu uugcuguaua guucauuaac  180
uuagguuauu aaauauuuuu ucauuauaac uggacuuuu cucaguuuau aguuuagaau  240
aaauuaaau uugcaaaac ucguucgaaa auuucggc uaaaccugua aacgcaaaua     300
cuaagaaauu uuagauggac augguucaa uucccaucag uuccacca                348
```

<210> SEQ ID NO 108
<211> LENGTH: 330
<212> TYPE: RNA
<213> ORGANISM: Guillardia theta -continued

<400> SEQUENCE: 108
ggggcugauu uggauucgac auauaaauuu gcguguuuca uuaugaagca agucaaguuu 60
aaugaucuug uaaaaaacau uaaaguacaa auaaaugcaa gcaauauagu uucauuuagu 120
ucaaaacguu uagucucuuu ugcauaagca aaauguguua auaacuuucu uaguagaaau 180
uggagaaguu uacuaagauu uauauuuacu ccauaauuau uuuaaagaug guaaaaaggu 240
gauucaucau uuguauguuu cuaaacuuug ugaaagaaua gugggcucca uuuauaauga 300 acgugggguuc aaaucccacc agcuccacca 330

<210> SEQ ID NO 109
<211> LENGTH: 353
<212> TYPE: RNA
<213> ORGANISM: Mycoplasma hyorhinis

<400> SEQUENCE: 109
cauacauaaa aggauauaaa uugcaguggu cuuguaaacc auaagacaau uucuuuacua 60
agcggaaaag aaaacaaaaa agaagauuau ucauuauuaa ugaaugcuuc aacucaauca 120
aaucuagcuu uugcauuuua aaaaacuagu agaccaauuu gcuucucacg aauuguaauc 180
uuuauauuag agaauaguua aaaaucugau cacuuuuuaa ugaauuuaua gaucacaggc 240
uuuuuuaauc uuuuuguuau uuuagauaaa gagucuucuu aaaaauaacu aaacuguagg 300
aauuuauauu uaauuaugcg uggacccggg uucaacuccc gccagcucca cca 353

<210> SEQ ID NO 110
<211> LENGTH: 411
<212> TYPE: RNA
<213> ORGANISM: Mycoplasma capricolum

<400> SEQUENCE: 110
ggggauguca uggauuugac aggauaucuu uaguacauau aagcaguagu guuguagacu 60
auaaauacua cuagguuuaa aaaaacgcaa auaaaaacga agaaacuuuu gaaaugccag 120
cauuuaugau gaauaaugca ucagcuggag caaacuuuau guuugcuuaa uaacuacuag 180
uuuaguuaua guauuucacg aauuauagau auuuuaagcu uuauuuuaaa ccguauuacc 240
caagcuuaau agaauauaug auugcaauaa auauauuuga aaucuaauug caaaugauau 300
uuaaccuuua guuaauuuua guuaaauauu uuaauuagaa aauuaacuaa acuguagaaa 360
guauguauua auauaucuug gacgcgaguu cgauucucgc caucuccacc a 411

<210> SEQ ID NO 111
<211> LENGTH: 381
<212> TYPE: RNA
<213> ORGANISM: Mycoplasma pirum

<400> SEQUENCE: 111
caugaaugau ggacccauag aggcaguggg guaugccccu uauagcucaa gguuuaaauu 60
aaccgacaaa acugacgaaa acguugccgu ugauacaaau uuauuaauca accaacaagc 120
ucaauuuaac uacgcauuug cauaguauaa aaaaauaaau ugugcuacuc auuguaauua 180
gguuacuaaa uuacuuuguu uuauauaguc cuguaacuag uucuagugau gucuauaaac 240
uagaaugaga uuuauagacu uauuuguugg cgguugugcc auagccuaaa ucaacaaaga 300
caauuuauuu augguacuaa acuguagauu cuaugaugaa auuauuugug gaaacggguu 360
cgauucccgc caucuccacc a 381

<210> SEQ ID NO 112
<211> LENGTH: 387
<212> TYPE: RNA
<213> ORGANISM: Mycoplasma pneumoniae

<400> SEQUENCE: 112

| | | | | | | |
|---|---|---|---|---|---|---|
| ggggauguag | agguuuugac | auaauguuga | aaggaaaaca | guugcagugg | gguaugcccc | 60 |
| uuacagcucu | agguauaaua | accgacaaaa | auaacgacga | aguuuggua | gauccaaugu | 120 |
| ugaucgcuaa | ccaacaagca | aguaucaacu | acgcuuucgc | uuagaacaua | cuaaagcuac | 180 |
| acgaauugaa | ucgccauagu | uugguucgug | ucacaguuua | uggcucgggg | uuaacugguu | 240 |
| caacuuaauc | cuuaaauuau | gaacuuaucg | uuuacuuguu | ugucuuauga | ucuaaaguaa | 300 |
| gcgagacauu | aaaacauaag | acuaaacugu | agaagcuguu | uuaccaaucc | uuuauggaaa | 360 |
| cggguucgau | ucccgucauc | uccacca | | | | 387 |

<210> SEQ ID NO 113
<211> LENGTH: 388
<212> TYPE: RNA
<213> ORGANISM: Mycoplasma genitalium

<400> SEQUENCE: 113

| | | | | | | |
|---|---|---|---|---|---|---|
| ggggauguuu | uggguuugac | auaaugcuga | uagacaaaca | guagcauugg | gguaugcccc | 60 |
| uuacagcgcu | agguucaaua | accgacaaag | aaaauaacga | aguguuggua | gauccaaauu | 120 |
| ugaucauuaa | ccaacaagca | aguguuaacu | uugcuuuugc | auaaguagau | acuaaagcua | 180 |
| cagcugguga | auagucauag | uuugcuagcu | gucauaguuu | augacucgag | guuaaaucgu | 240 |
| ucaauuuaac | cuuuaaaaau | agaacuuguu | guuccauga | uuguuuugug | aucaauugga | 300 |
| aacaagacaa | aaauccacaa | aacuaaaaug | uagaagcugu | uguugugguc | cuuuauggaa | 360 |
| acggguucga | uucccgucau | cuccacca | | | | 388 |

<210> SEQ ID NO 114
<211> LENGTH: 412
<212> TYPE: RNA
<213> ORGANISM: Ureaplasma urealyticum

<400> SEQUENCE: 114

| | | | | | | |
|---|---|---|---|---|---|---|
| ggggauguca | cgguuucgac | gugacacauu | aauuuuuaau | ugcagugggg | uuagccccuu | 60 |
| aucgcuuucg | aggcauuuua | aaugcagaaa | auaaaaaauc | uucugaagua | gaauuaaacc | 120 |
| cagcguuuau | ggcuucagcu | acuaaugcaa | acuacgcuuu | ugcguacuaa | uuaguuauua | 180 |
| guagaaacgu | ucauuaacau | aauuacuauu | gguugguuuu | ugggcuuauu | uuacaauagu | 240 |
| uuuaaauuua | aaauucuuau | uguuguuuaa | auuuaaauag | auuuaacaaa | uaguuaguua | 300 |
| auuuuaaauu | uguuuuauua | guuauuaacu | acacuauuuu | uaauaaaacu | aaacuguaga | 360 |
| uauuauuaau | uauguguuugc | ggaaaggggu | ucgauucccc | ucaucuccac | ca | 412 |

<210> SEQ ID NO 115
<211> LENGTH: 365
<212> TYPE: RNA
<213> ORGANISM: Mycoplasma salivarium

<400> SEQUENCE: 115

| | | | | | | |
|---|---|---|---|---|---|---|
| caggcauucg | auucauuaug | uugcagugguu | uugcaaacca | uaaggcacua | ggcuuuuuua | 60 |
| aacgcaaaag | accaaaaaac | agaagaucaa | gcaguugauc | uagcauuuau | gaauaauuca | 120 |
| caaaugcaau | caaaucuagu | uuucgcuuag | uaaaauuagu | caauuuauua | uggugcucaa | 180 |

```
cauaauaaau gguaguauga gcuuaauauc auaugauuuu aguuaauaug auaggauuug    240
uaacuaaacu auguuauaga aauuuguaaa uuauauauau gacauaggaa auuuaauuua    300
cuaaacugua gaugcauaau guugaagaug uguggaccgg gguucaacuc ccgccagcuc    360
cacca                                                                365
```

<210> SEQ ID NO 116
<211> LENGTH: 363
<212> TYPE: RNA
<213> ORGANISM: Clostridium innocuum

<400> SEQUENCE: 116

```
cggggauaug ucgguacag acugcagucg aguggunacg uaauaaccaa uuaaauuuaa     60
acggaaaaac uaaauuagcu aaccucuuug guggaaacca gagaauggcu uucgcugcuu   120
aauaaccgau auagguucgc agccgccucu gcaugcuucu ccuugacca uggaugug      180 cgcguaagac gcaagggaua aggaaucugg uuugccugag aucagauuca cgaaaauucu   240
ucaggcacau caucagcgg auguucauga ccugcugaug ucuuaaucuu cauggacuaa    300
acuguagagg ucguacgug gggcuguuuc uggacaggag uucgauuccc gccgccucca    360
cca                                                                 363
```

<210> SEQ ID NO 117
<211> LENGTH: 359
<212> TYPE: RNA
<213> ORGANISM: Mycoplasma fermentans

<400> SEQUENCE: 117

```
caugcauugg gugauacuaa aucaguagu uuggcagacu auaaugcauc uaggcuuuau     60
aaucgcagaa gauaaaaag cagaagaagu uaauauuucu ucacuuauga uugcacaaaa    120
aaugcaauca caaucaaacc uugcuuucgc uuaguuaaaa gugacaagug guuuaaagu    180 ugacauuuuc cuauauauuu uaaaaucggc uuuuaaggag aacaggaguc ugaaaggguu   240
ccaaaaaucu auauuguuug cauuucggua guauagauua auuagaaaug auaaacugua   300
aaaaguauug guauugacuu ggugugugga cucgggguca acucccgcca gcuccacca    359
```

<210> SEQ ID NO 118
<211> LENGTH: 320
<212> TYPE: RNA
<213> ORGANISM: Acidobacterium capsulatum

<400> SEQUENCE: 118

```
cggggunagac ugcggcaaag aggcaugccg gggggugggc acccguaauc gcucgcaaaa    60
caauacuugc caacaacaau cuggcacucg cagcuuaauu aaauaaguug ccguccucug    120
aggcuucgcc uguggggccga ggcaggacgu cauacagcag gcuggunccu ucggcuggu    180 cugggccgcg gggaugagau ccacggacua gcauucugcg uaucuugucg cuucuaagcg    240
cagagugcga aaccuaaagg aaugcgacug agcauggagu cucuuuucug acaccaauuu    300
cggacgcggg uucgauuccc                                                320
```

<210> SEQ ID NO 119
<211> LENGTH: 319
<212> TYPE: RNA
<213> ORGANISM: Fusobacterium mortiferum

<400> SEQUENCE: 119

```
cggggUUaUg agguuauagg uagcaugcca ggaugaccgc ugugagaggu caacacaucg     60
uuuagaugga aacagaaauu acgcuuuagc ugcuuaauua gucagcucac cucugguuuc    120
ucucuucugu aggagaaucc aaccgaggug uuaccaauau acagauuacc uuuagugauu    180
ucucuaagcu caaagggaca uuuuagagaa uagcuucagu uagcccuguc ugcgggagug    240
auuguugcga auaaaauag uagacuaagc auuguagaag ccuauggcgc ugguaguuuc     300
ggacacgggu ucaacuccc                                                319

<210> SEQ ID NO 120
<211> LENGTH: 329
<212> TYPE: RNA
<213> ORGANISM: Fibrobacter succinogenes

<400> SEQUENCE: 120
cagggUUacc gaaguguuag uugcaagucg aggucucaga cgagggcuac ucguuaaaaa    60
gucugaaaaa aaauaagugc ugacgaaaac uacgcacucg cugccuaauu aacggcaacg   120
ccgggccuca uuccgcuccc aucggggugu acguccggac gcaauauggg auagggaagu   180
gucaugccug ggggcaucuc ccgagauuuu cuaggcuggu caaacccgc gccgaccuuc    240 uugggcgugg auaagacgag aucuuaaauu cgaagggaac acuuguagga acguacaugg   300
acgugauuuu ggacaggggu ucaacuccc                                    329

<210> SEQ ID NO 121
<211> LENGTH: 300
<212> TYPE: RNA
<213> ORGANISM: Artificial
<220> FEATURE:
<223> OTHER INFORMATION: isolated from rumenal fluid

<400> SEQUENCE: 121
acgcccuugu cucagacgag ggcacucguu aaaaagucug aaaagaauaa cugcagaacc    60
uguagcuaug gcugcuuaau uuaagggcaa cccuuggauc cgccuccauc ccgaagggu   120 ggcauccgag ucgcaaaucg ggauaggaug gaucuuggca acgaggagua cauccgaaau   180
uugucgcugc uggcugaagc aucgccguuc cucuuugggc guggcaaggc aagauuaaau   240
ucagaggaua agcguguagu agcgagugag uaggugucuu uggacgcggg uucaagucccc   300

<210> SEQ ID NO 122
<211> LENGTH: 330
<212> TYPE: RNA
<213> ORGANISM: Pirellula staleyi

<400> SEQUENCE: 122
ccggauagcc ugaagcgaau acggcgugcc guggugauc agauggccac guaaaaagcu    60
gaucacaaac uuaacugccg agagcaaucu cgcacuugcu gccuaacuaa acggguagcuu  120 ccgacugagg gcuuuagccg gagaggccca aaaguuggc accaaauccg gaccgccucg    180
ugccaugauc gaaacgcacg aggucaaaaa aguuucgauc uagugcaggg uguagccagc   240
agcuaggcga caaacugugc aaaaaucaaa uuuucugcua cgcacguaga ugguguucgug  300 aaaaugucuc gggacggggg uucaacuccc                                   330

<210> SEQ ID NO 123
<211> LENGTH: 329
<212> TYPE: RNA
<213> ORGANISM: Planctomyces maris

<400> SEQUENCE: 123
```

```
cugguucacc guauguuaag guggcggugc cgugguugau caguuggcca cguaaaaagc    60
ugaucacaau cuaauugcaa acaagcaauu ucaauggcu gcuuauaaa agcaaccccg    120 gcuuaggaau cucugucuga ggaguccgac agcuggucac aaaaucagac ugguaucaga   180
ucaauguccg cuccgucuga uacgagauuc gugguggacu gguuccaac aggcucuguu   240 uaucgugccc gaagaaacga gacucaaacg auaaaauaug caccguagag gcuuuagcug   300
agggUucaca ggacgcgggu ucaacuccc                                    329

<210> SEQ ID NO 124
<211> LENGTH: 318
<212> TYPE: RNA
<213> ORGANISM: Artificial
<220> FEATURE:
<223> OTHER INFORMATION: isolated from sludge

<400> SEQUENCE: 124
cagggaacca ggagguguga gaugcaugcc ggagacgcug uccgcuccgu uaucaagcag    60
cacaacaaaa uaauugcaaa caacaauuac uccuuagcag cguaagcagc uaacguucaa   120
ccucuccgga ccgccgggag gggauuuggg cgucgaaaca gcgcggacgc uccggauagg   180
acgcccauaa uauccggcua agaccauggg ucuggcucuc gcggggucuga uugucuucca   240 ccgcgcgggc cgcgaucaaa gacaacuaag cauguagguu cuugcauggc cuguucuuug   300
gacgcggguu cgauuccc                                                318

<210> SEQ ID NO 125
<211> LENGTH: 407
<212> TYPE: RNA
<213> ORGANISM: Porphyromonas gingivalis

<400> SEQUENCE: 125
ggggcugacc ggcuuugaca gcgugaugaa gcgguaugua agcauguagu gcguggugg    60 cuugcacuau aaucucagac aucaaaaguu uaauuggcga aaauaacuac gcucucgcug   120
cguaaucgaa gaauaguaga uuagacgcuu caucgccgcc aaaguggcag cgacgagaca   180
ucgcccgagc agcuuuuucc cgaaguagcu cgauggugcg gugcugacaa aucgggaacc   240
gcuacaggau gcuuccugcc uguggucaga ucgaacggaa gauaaggauc gugcauuggg   300
ucguuucagc cuccgcucgc ucacgaaaau ccaacugaa acuaaacaug uagaaagcau   360
auugauucca uguuuggacg agggUucauu cccuccagc uccacca                 407

<210> SEQ ID NO 126
<211> LENGTH: 379
<212> TYPE: RNA
<213> ORGANISM: Bacteroides thetaiotaomicron

<400> SEQUENCE: 126
cagcgggcag aaaugguagg uaagcaugca guggucggu aauuccacu uaaaucucag    60 uuaucaaaac uuuaucuggc gaaacuaauu acgcucuugc ugcuuaaucg aaucacagua   120
gauuagcuua auccaggcac uaggugccca ggagagacau cacucggaag cuguugcucc   180
gaagcauucc gguucagugg ugcaguaaca ucggggauag ucagaagcgg ccucgcguuu   240
uugaugaaac uuuagaggau aaggcaggaa uugauggcuu ugguucugcu ccugcacgaa   300
aauuuaggca aagauaagca uuagaaaagc uuaugauuuc cucguuugga cgagggUuca   360
acucccgcca gcuccacca                                               379
```

```
<210> SEQ ID NO 127
<211> LENGTH: 404
<212> TYPE: RNA
<213> ORGANISM: Chlorobium tepidum

<400> SEQUENCE: 127
ggggaugaca ggcuaucgac aggauaggug ugagaugucg uugcacuccg aguuucagca      60
uggacggacu cguuaaacaa gucuaugac caauagaugc agacgauuau ucguaugcaa     120
uggcugccug auuagcacaa guuaauucag aagccaucgu ccugcgguga augcgcuuac    180
ucugaagccg ccggauggca uaccccgcgc uugagccuac ggguucgcgc aaguaagcuc    240
cguacauuca ugcccgaggg ggugugcggg uaaccaaucg ggauaagggg acgaacgcug    300
cuggcggugu aaucggacca cgaaaaacca accaccagag augagugugg uaacugcauc    360
gagcaguguc cuggacgcgg guucaagucc cgccaucucc acca                     404

<210> SEQ ID NO 128
<211> LENGTH: 372
<212> TYPE: RNA
<213> ORGANISM: Chlorobium limicola

<400> SEQUENCE: 128
caggauacgu gugagauguc guugcacucc gaguuucagc auggacggac ucguuaaaca      60
agucuaugua ccauuagaug cagacgauua uucguaugca auggcugccu gauuagcaca    120 aguuaaacuca gacgccaucg uccugcggug aaugcgcuua cucugaagcc gccggauggc    180
auaacccgcg cuugagccua cggguucgcg caaguaagcu ccguacauuc augcccgagg    240
ggcugugcgg guaauuucuc gggauaaggg gacgaacgcu gcuggcggug uaaucggccc    300
acgaaaaccc aaucaccaga gaugagugug ugacugcau cgagcagugu uuggacgcg    360 gguucaacuc cc                                                        372

<210> SEQ ID NO 129
<211> LENGTH: 420
<212> TYPE: RNA
<213> ORGANISM: Chlamydia trachomatis

<400> SEQUENCE: 129 gggggguguaa agguuucgac uuagaaauga agcguuaauu gcaugcggag ggcguuggcu     60
ggccuccuaa aaagccgaca aaacaauaaa ugccgaaccu aaggcugaau gcgaaauuau    120
cagcuucgcu gaucucgaag aucuaagagu agcugcuuaa uuagcaaagu uguuaccuaa    180
auacggguga cccggguguuc gcgagcucca ccagagguuu ucgaaacacc gucauguauc    240
ugguuagaac uuaggguccuu uaauucucga ggaaaugagu uugaaauuua augagagucg    300
uuagucucua uaggguuuc uagcugagga gacauaacgu auaguaccua ggaacuaagc    360
auguagaggu uagcggggag uuuacuaagg acgagaguuc gacucucucc accuccacca    420

<210> SEQ ID NO 130
<211> LENGTH: 421
<212> TYPE: RNA
<213> ORGANISM: Chlamydia mousep*

<400> SEQUENCE: 130 gggggguguaa agguuucgac uuagaaauga agcguuaauu gcaugcggag ggcguuggcu     60
ggccuccuaa aaagccgaca aaacaauaaa ugccgaaccu aaggcugaau gcgaaauuau    120
cagcuucgcu gaucuuaaug aucuaagagu ugcugcuuaa uuagcaaagu uguuaccuaa    180
```

```
guacugguaa cccgguguuc gcgagcucca ccagagguuu ucgaaacgcc gucauuuauc    240
ugguuagaau uagggccuuu uaacucucaa gggaacuaau uugaauuuua augagagucg    300
uuggucucua uagagguuuc uagcugagga gauauaacgu aaaauauucu agaaacuaag    360 caugauagagg uuagcgggga guuuacuaag gacgagaguu cgaaucucuc caccuccacc    420
a                                                                    421

<210> SEQ ID NO 131
<211> LENGTH: 426
<212> TYPE: RNA
<213> ORGANISM: Chlamydia pneumoniae

<400> SEQUENCE: 131 gggguguau agguuucgac uugaaaauga aguguuaauu gcaugcggag ggcguuggcu      60
ggccuccuaa aaagccaaca aaacaauaaa ugccgaaccu aaggcugaau gcgaaauuau    120
uagcuuguuu gacucaguag aggaaagacu agcugcuuaa uuagcaaaag uuguuagcua    180
gauaaucucu agguaacccg guaucugcga gcuccaccag aggcuugcaa aauaccguca    240
uuuaucuggu uggaacuuac uuucucuaau ucucaaggaa guucguucga gauuuugag     300 agucauuggc ugcuauagag gcuucuagcu aagggaagucc aaugaaaaca auucuagaag   360
auaagcaugu agagguuagc agggaguuug ucaaggacga gaauucgagu cucuccaccu    420
ccacca                                                              426

<210> SEQ ID NO 132
<211> LENGTH: 328
<212> TYPE: RNA
<213> ORGANISM: Micrococcus luteus

<400> SEQUENCE: 132 cgguguguugu cgcgucggga gaagcgggcc gaggaugcag agucaucucg ucaaacgcuc    60
ucugcaaacc aauaagugcc gaauccaagc gcacugacuu cgcucucgcu gccugaucag   120
ugaucgaguc cgucacccccg aggucgcugu cgccucggau cguggcguca gcuagauagc   180
cacugggcgu caccccucgcc gggggucgug acgccgacau caauccggcu ggguccgggu   240
uggccgcccg ucugcgggac ggccaggacc gagcaacacc cacagcagac ugcgcccgga   300
gaagaccugg caacacccuca ucggacgc                                     328

<210> SEQ ID NO 133
<211> LENGTH: 368
<212> TYPE: RNA
<213> ORGANISM: Mycobacterium leprae

<400> SEQUENCE: 133
ggggcugaaa gguuucgacu ucgcgcaucg aaucaaggga agcgugccgg ugcaggcaag    60
agaccaccgu aagcgucguu gcagcaauau aagcgccgau ucauaugagc gcgacuaugc   120
ucucgcugcc uaagcgaugg cuagucuguc agaccgggaa cgcccucguc ccggagccug   180
gcaucagcua gagggaucua ccgauggguu cggucgcggg acucgucggg acaccaaccg   240
cgacugggau cgucauccug gcuaguucgc gugaucagga gauccgagua gaggcauagc   300
gaacuacgca cggagaagcc uugagggaaa ugccguagga cccggguucg auucccggca   360
gcuccacc                                                            368

<210> SEQ ID NO 134
```

```
<211> LENGTH: 360
<212> TYPE: RNA
<213> ORGANISM: Mycobacterium tuberculosis

<400> SEQUENCE: 134
ggggcugaac gguuucgacu ucgcgcaucg aaucaaggga agcgugccgg ugcaggcaag    60
agaccaccgu aagcgucguu gcgaccaaau aagcgccgau ucaucagc gcgacuacgc     120
ucucgcugcc uaagcgacgg cuagucuguc agaccggaa cgcccucggc ccggacccug    180
gcaucagcua ccaccgauga guccggucgc gggacuccuc gggacaacca cagcgacugg   240
gaucgucauc ucggcuaguu cgcgugaccg ggagauccga gcagaggcau agcgaacugc   300
gcacggagaa gccuugaggg aaugccguag gacccggguu cgauucccgg cagcuccacc   360

<210> SEQ ID NO 135
<211> LENGTH: 373
<212> TYPE: RNA
<213> ORGANISM: Mycobacterium avium

<400> SEQUENCE: 135
ggggcugaaa gguuucgacu ucgcgcaucg aaucaaggga agcgugccgg ugcaggcaac    60
ugaccaccgu aagcgucguu gcagauagau aagcgccgau ucaucagc gcgacuacgc     120
ucucgcugcc uaagcgacag cuagucgagg gaucgucagc ccgggaacgc ccucgacccg   180
gagccuggcg ucagcuagag ggauccaccg augaguucgg ucgcgggacu caucgggaca   240
ccaacagcga cugggaucgu cauccuggcu uguucgcgug accaggagau ccgaguagag   300
gcauagcgaa cugcgcacgg agaagccuug agggaaugcc guaggacccg gguucgauuc   360
ccggcagcuc cac                                                     373

<210> SEQ ID NO 136
<211> LENGTH: 331
<212> TYPE: RNA
<213> ORGANISM: Corynebacterium xerosis

<400> SEQUENCE: 136
cuucguacau ugagccaggg gaagcgugcc ggugaaggcu ggagaccacc gcaagcgucg    60
cagcaaccaa uuaagcgccg agaacucuca gcgcgacuac gcccucgcug ccuaagcagc   120
gaccgcgugu cugucagacc ggguaggccu cugauccgga cccuggcauc guuuagugg   180
gcucgcucgc cgacuugguc gcaagggucg cggggacac ucacuugcga cugggcccgu    240
cauccgguca uguucgacug aaccggaggg ccgagcagag accacgcgcg aacugcgcac   300
ggagaagccc uggcgaggug acggaggacc c                                  331

<210> SEQ ID NO 137
<211> LENGTH: 354
<212> TYPE: RNA
<213> ORGANISM: Treponema pallidum

<400> SEQUENCE: 137
ggggaugacu agguuucgac uagggauguq gggguugcg cugcaggugg agugucgauc    60
uccugauucg gcgccuuuau aacugccaau ucgacaguu ucgacuacgc gcucgccgcg   120
uaaucgcggg ccuguguuug cgcugcucug agcgaacaua ucggcccgac gccaaacgga  180
gcuugcucuu acguugugca cggcggacgu agggggacuu uugucugugc uaagacucug   240
gcgcugcgg ugcaggccua gcagagugccg acaaacgcag uacgcaccgc uaaaccugua   300
ggcgcgcagc acucgcucuu uaggacgggg guucgauucc ccccaucucc acca          354
```

<210> SEQ ID NO 138
<211> LENGTH: 362
<212> TYPE: RNA
<213> ORGANISM: Borrelia burgdorferi

<400> SEQUENCE: 138

```
ggggauguuu uggauuugac ugaaaauguu aauauuguaa guugcaggca gagggaaucu      60
cuuaaaacuu cuaaaauaaa ugcaaaaaau aauaacuuua caagcucaaa ucuuguaaug     120
gcugcuuaag uuagcagagg guuuguuga auuggcuuu gagguucacu uauacucuuu       180
ucgacaucaa agcuugcuua aaaauguuuu caaguugauu uuuagggacu uuuauacuug    240
agagcaauuu gguggguugc uaguauuucc aaaccauauu gcuuaauaaa auacuagaua    300
agcuuguaga agcuuauagu auuauuuuua ggacgcgggu caauucccg ccaucuccac     360
ca                                                                   362
```

<210> SEQ ID NO 139
<211> LENGTH: 364
<212> TYPE: RNA
<213> ORGANISM: Borrelia garinii

<400> SEQUENCE: 139

```
ggggcugauu cuggauucga cugaaaaugc gaauauugua aguugcaggc agagggaauc      60
ucuuaaaacu cuaaaauaa augcaaaaaa uaauaacuuu acaagcucaa accuuguaau     120
ggcugcuuaa guuagcaggg aguuucguug aauuggcuu ugagguucac uuauacucuu     180
uucgauaucg aagcuugcuu aaaaauguuu ucaaguuaau uuuuagggac uuuuguacuu    240
gagagcaauu uggcgguuug cuaguauuuc caaaccauau ugcuuaagua aaugcuaga     300
uaagcuugua gaagcuuaua auauuguuuu uaggacgcgg guucaauucc cgccaucucc    360
acca                                                                 364
```

<210> SEQ ID NO 140
<211> LENGTH: 363
<212> TYPE: RNA
<213> ORGANISM: Borrelia afzelii

<400> SEQUENCE: 140

```
ggggcugauu cuggauucga cugaaaaugc uaauauugua aguugcaagc agagggaauc      60
ucuuaaaacu cuaaaauaua augcaaaaaa uaauaacuuu acaaguucaa accuuguaau     120
ggcugcuuaa guuagcagag aguuuguug aauuggcuu ugagauucac uuauacucuu      180
uuagacaucg aagcuugcuu aaaaauguuu ucaagugau uuuuagggac uuuuauacuu     240
gagagcaauu uggcgguuug cuaguauuuc caaaccauau ugcuuaguaa aauacuagau    300
aagcuuguag aagcuuauag uauuguuuuu aggacgcggg uucaauuccc gccaucucca    360
cca                                                                  363
```

<210> SEQ ID NO 141
<211> LENGTH: 363
<212> TYPE: RNA
<213> ORGANISM: Borrelia crocidurae

<400> SEQUENCE: 141

```
ggggcugauu cuggauucga cuaagaacuu uaguagcaua aauggcaagc agagugaauc      60
ucuuaaaacu cuuuaauaa augcaaaaaa uaauaacuuu acaaguucag aucuuguaau     120
```

```
ggcugcuuaa uuuagcagag aguuuuguug gauuuugcuu ugagguucaa cuuauacucu    180
uuaagacauc aaaguaugcc uaaaaauguu ucaaguugau uuuuagggac cuuuaaacuu    240
gagaguaauu ugguggu uug cuuguuuucc aagccuuauu gcuuuuucua aaaauuagcu   300
aagcuuguag auauuuauga uauuauuuuu uggacgcggg ucaauuccc gccaucucca     360 cca                                                                   363

<210> SEQ ID NO 142
<211> LENGTH: 365
<212> TYPE: RNA
<213> ORGANISM: Borrelia hermsii

<400> SEQUENCE: 142
ggggcugauu cuggauucga cuaaaaacuu uaguagcaua aauugcaagc agagggaauc    60
ucuuaaaacu ucuuuaauaa augcaagaaa uauaacuuuu acaaguucaa aucuuguaau    120
ggcugcuuaa auuagcagag aguucugcug gauuuugcuu ugagguucag cuuauacucu    180
uuuaagacau caaagcuugc uuaaaaauau ucaaguuga uuuuuaggga cuuuuaaauu    240
ugagaguaau uggcgguuu gcaguuuuu ccaaaccuua uuacuaaag aaaacacuag      300 cuaagcuugu agauauuuau gauauuauuu uuaggacgcg gguucaauuc ccgccaucuc    360
cacca                                                                365

<210> SEQ ID NO 143
<211> LENGTH: 330
<212> TYPE: RNA
<213> ORGANISM: Alcaligenes faecalis

<400> SEQUENCE: 143
cgggggucaa gaagcagcac agggcguguc gagcaccagu acgcucguaa auccacugga    60
aaacuauaaa cgccaacgac gagcguuucg cucuagccgc uuaaggcugg gccacugcac    120
uaauuugucu uugggu uagg uagggcaacc uacagcagug uuauuacaa agaaucgaau    180 cggucugcgc cacgaagucc gguucuaaaa cuuaguggau cgccaaggaa aggccuguca    240
auuggcauag uccaagguua aaacuuaaaa uuaauugacu acacauguag aacugucugu    300
ggacggcuug cggacggggg uucgauuccc                                     330

<210> SEQ ID NO 144
<211> LENGTH: 340
<212> TYPE: RNA
<213> ORGANISM: Alcaligenes eutrophus

<400> SEQUENCE: 144 cgugggu uac aaagcagugg agggcauacc gaggacccgu caccucguua aucaauggga    60
augcaauaac ugcuaacgac gaacguuacg cacuggccgc uuaauugcgg ccguccucgc    120
acuggcucgc ugacgggcua ggucgcaag accacgcgag gucauuuacg ucagauaagc    180
uccggaaggg ucacgaagcc ggggacgaaa accaguga c ucgccgucgu agagcguguu    240
cguccgcgau gcgccgguua aaucaaauga cagaacuaag uauguagaac ucucugugga    300
gggcuuacgg acgcggguuc gauucccgcc ggcuccacca                          340

<210> SEQ ID NO 145
<211> LENGTH: 326
<212> TYPE: RNA
<213> ORGANISM: Ralstonia pickettii

<400> SEQUENCE: 145
```

```
cggggguugc gaagcagcgg agggcauacc gaggacccgu caccucguua aucaauggga      60
augcaauaac ugcuaacgac gaacguuacg cacuggcagc cuaagggccg ccguccucgc     120
acuggcucgc ugacgggcua gggucgcaag accagcgagg ucauuuacgu cagauaagcu     180
uuaggugagu cacgggccua gagacgaaaa cuuagugaau cgccgucgua gagcguuuc      240 guccgcgaug cggcgguuaa aucaaaugac agaacuaagu auguagaacu cucuguggag     300
ggcuugcgga cgcggguucg auuccc                                         326

<210> SEQ ID NO 146
<211> LENGTH: 363
<212> TYPE: RNA
<213> ORGANISM: Neisseria gonorrhoeae

<400> SEQUENCE: 146
gggggcgacc uugguuucga cgggggguugc gaagcagaug cgggcauacc ggggucucag    60
auccccguaa aacacugaau ucaaauaguc gcaaacgacg aaacuuacgc uuuagccgcu    120
uaaggcuagc cguugcagca gucggucaau gggcugugug gugaaagcca ccgcaacguc    180
aucuuacauu gacugguuuc cagccggguu acuuggcagg aaauaagacu uaagguaacu    240
gguuuccaaa aggccuguug gucggcauga uggaaauaag auuuucaaau agacacaacu    300
aaguauguag aacgcuuugu agaggacuuu cggacggggg uucgauuccc cccgccucca    360
cca                                                                 363

<210> SEQ ID NO 147
<211> LENGTH: 363
<212> TYPE: RNA
<213> ORGANISM: Neisseria meningitidis

<400> SEQUENCE: 147
gggggcgacc uugguuucga cgggggguugc gaagcagaug cgggcauacc ggggucucag    60
auccccguaa aacacugaau ucaaauaguc gcaaacgacg aaacuuacgc uuuagccgcu    120
uaaggcuagc cguugcagca gucggucaau gggcugugug gcgaaagcca ccgcaacguc    180
aucuuacauu gacugguuuc cugccggguu auuuggcagg aaaugagauu uaagguaacu    240
gguuuccaaa aggccuguug gucggcauga uggaaauaag auuuucaaau agacacaacu    300
aaguauguag aacgcuuugu agaggacuuu cggacggggg uucgauuccc cccgccucca    360
cca                                                                 363

<210> SEQ ID NO 148
<211> LENGTH: 333
<212> TYPE: RNA
<213> ORGANISM: Chromobacterium violaceum

<400> SEQUENCE: 148
cggggguugc gaagcagaug agggcauacc gggauuucag ucaccccgua aaacgcugaa     60
uuuauauagu cgcaaacgac gaaacuuacg cucuggcagc cuaacggccg gccagacacu    120
acaacgguuc gcagaugggc cggggcaguc aaaacccugu agugcacucu acaucugcu     180 agugcuguuc cgghuuacuu gguucagugc gaaauaauag guaacucgcc aaagccagc     240 cuguccgucg gcguggcaga gguuaaaucc aaaugacacg acuaaguaug uagaacucac    300
uguagaggac uuucggacgc ggguucaacu ccc                                 333

<210> SEQ ID NO 149
```

```
<211> LENGTH: 330
<212> TYPE: RNA
<213> ORGANISM: Nitrosomonas cryotolerans

<400> SEQUENCE: 149 cgugggguugc aaagcagcgc agggcauacc gaggaccaga auaccucgua aauacaucug      60
gaaaaaaaua gucgcaaacg acgaaaacua cgcuuuagcc gcuuaauacg gcuagccucu     120
gcaccgaugg gccuuaacgu cgggucuggc aacagacagc agagcauua gcaaggaucg      180 cguucuguag ggucacuuua cagaacguua acaauaggu gacucgccug ccaucagccc      240
gccagcuggc gguugucagg uuaaauuaaa gagcauggcu aaguauguag aacugucugu    300
agaggacuug cggacgcggg uucaacuccc                                      330

<210> SEQ ID NO 150
<211> LENGTH: 331
<212> TYPE: RNA
<213> ORGANISM: Methylobacillus glycogenes

<400> SEQUENCE: 150 cgggggguugc aaagcagcgc agggcauacc gaggccuagu caccucguaa auaaacuaga     60
acaaguauag ucgcaaacga cgaaacuuac gcucuagccg cuuaaucccg gcuggacgcu    120
gcaccgaagg gccucucggu cgggugggggu aacccacagc agcgucauua agagaggauc   180
gugcgauauu ggguuacuua auaucguauu aaauccaagg uaacucgccu gcuguuugcu    240
ugcucguugg ugagcaucag guuaaaucaa acaacacagc uaaguaugua gaacugucug    300
uggagggcuu gcggacgggg guucgauucc c                                    331

<210> SEQ ID NO 151
<211> LENGTH: 375
<212> TYPE: RNA
<213> ORGANISM: Pseudomonas testosteroni

<400> SEQUENCE: 151
ggggccgauu cuggauucga cgugggguucg ggaccggugc ggugcaugug gagcuugagu      60
gacgcucgua aaucuccauu caaaaaacua acugcaaacg acgaacguuu cgcacucgcc     120
gcuuaauccg gugagccuug caacagcacg cuaguggggcu gggcaagggg guagcaauac    180 cuccccggcug caagggaauu ucauuagcu ggcuggauac cgggcuucuu gguauuuggc     240
gagauuuuag gaagcuggcu acccaagcag cgugugccug cggggguuugg guggcgagau   300 uuaaaacaga gcacuaaaca uguagaucug uccggcgaag gcuuacggac gcgggguucaa    360 uucccgccgg cucca                                                      375

<210> SEQ ID NO 152
<211> LENGTH: 353
<212> TYPE: RNA
<213> ORGANISM: Variovorax paradoxus

<400> SEQUENCE: 152 cgugggguucg gagucgcagc ggggcauguc gagcugaaug cgcucguaaa acagauucaa      60
acaaacuaac ugcaaacgac gaacguuucg cacucgcugc uuaauugcca gugagccuug     120
caacaguugg ccgauggggcu gggcaagggg gucuggagca auccgaccu cccggcugca     180 aggauaacua caugggcugg cuccgauccg gguaccuugg gucggggcga gaaaauaggg    240
uacuggcguc cgguuuagcg ugugacgcg cgacuccgga agcgagacuc aaaacagauc    300
acuaaacaug uagaacugcg cgaugaaggc uugcggacgg ggguucaacu ccc            353
```

-continued

<210> SEQ ID NO 153
<211> LENGTH: 345
<212> TYPE: RNA
<213> ORGANISM: Hydrogenophaga palleroni

<400> SEQUENCE: 153 cgugggguucg gacgcgcagc agggcauguc gagguucugu caccucguaa aucagcagaa 60
aaaaaccaac ugcaaacgac gaacguuucg cacucgccgc uuaaacaccg gugagccuug 120
caacagcagg ccgaugggcu gggcaagggg gucgcaagac cucccggcug caagguaauu 180
uacaucggcu gguucugcgu cgggcaccuu ggcgcaggau gagauucaag gaugcuggcu 240
ucccguuuag cgugccacug cgcgacucgg gcggcgagac ccaaaucaga cggcuacaca 300
uguagaacug cucgaaaaag gcuugcggac gggggguucaa cuccc 345

<210> SEQ ID NO 154
<211> LENGTH: 387
<212> TYPE: RNA
<213> ORGANISM: Bordetella pertussis

<400> SEQUENCE: 154
ggggccgauc cggauucgac gugggucaug aaacagcuca gggcaugccg agcaccagua 60
agcucguuaa uccacuggaa cacuacaaac gccaacgacg agcgucucgc ucucgccgcu 120
uaagcgguga gccgcugcac ugaucugucc uugggucagg cgggggaagg caacuuccca 180
gggggcaacc ccgaaccgca gcagcgacau ucacaaggaa ucggccaccg cuggggucac 240
acggcguugg uuuaaauuac gugaaucgcc cugguccggc ccgucgaucg gcuaagucca 300
ggguuaaauc caaauagauc gacuaagcau guagaacugg uugcggaggg cuugcggacg 360
gggguucaau uccccccggc uccacca 387

<210> SEQ ID NO 155
<211> LENGTH: 323
<212> TYPE: RNA
<213> ORGANISM: Legionella pneumophila

<400> SEQUENCE: 155 cgugggguugc aaaaccggaa gugcaugccg agaaggagau cucucguaaa uaagacucaa 60
uuaaauauaa augcaaacga ugaaaacuuu gcuggugggg aagcuaucgc ugccuaauaa 120
gcacuuuagu uaaaccauca cuguguacug gccaauaaac ccaguauccc guucgaccga 180
gcccgcuuau cgguaucgaa ucaacgguca uaagagauaa gcuagcgucc uaaucuaucc 240
cggguuaugg cgcgaaacuc agggaaucgc uguguaucau ccugcccguc ggaggagcca 300
caguuaaauu caaaagacaa ggc 323

<210> SEQ ID NO 156
<211> LENGTH: 315
<212> TYPE: RNA
<213> ORGANISM: Chromatium vinosum

<400> SEQUENCE: 156
cgugggucgc gaaaccuaag gugcaugccg aggugcgguu gaccucguaa aacccuccgc 60
aaacuuauag uugccaacga cgacaacuac gcucucgcug cuuaauccca gcgggccucu 120
gaccgucacu ugccuguggg cggcggauuc caggguaac cucacacagg aucgugguga 180
cgggaguccg gaccugaucc acuaaaaccu aacggaaucg ccgacugauc gcccugcccu 240

```
ucgggcggca gaaggcuaaa aacaauagag ugggcuaagc auguaggacc gagggcagag    300
ggcuugcgga cgcgg                                                     315

<210> SEQ ID NO 157
<211> LENGTH: 318
<212> TYPE: RNA
<213> ORGANISM: Dichelobacter nodosus

<400> SEQUENCE: 157
cucgaggugc augucgagaa ugagagaauc ucguuaaaua cuucaaaac uuauaguugc     60 aaacgacgac aacuacgcuu uagcggcuua auucccgcuu ucgcuuaccu agauuugucu    120
gugggunuac cguaagcgac auuaacacag aaucgcuggu uaacgcgucc gcuguuaauc    180
gguuaaauua agcggaaucg cuuguaaaau gccugagcgu uggcuguuua ugaguuaaac    240
cuaauuaacu gcucuaaaca uguaguacca aaaguuaagg auucgcggac ggggguucaa    300
auccccccgc cuccacca                                                  318

<210> SEQ ID NO 158
<211> LENGTH: 354
<212> TYPE: RNA
<213> ORGANISM: Pseudomonas aeruginosa

<400> SEQUENCE: 158
ggggccgauu aggauucgac gccgguaaca aaacuugagg ggcaugccga gcugguagca    60
gaacucguaa auucgcugcu gcaaacuuau aguugccaac gacgacaacu acgcucuagc    120
ugcuuaaugc ggcuagacag ucgcuagggg augccuguaa acccgaaacg acugucagau    180
agaacaggau cgccgccaag uucgcuguag acguaacggc uaaaacucau acagcucgcu    240
ccaagcaccc ugccacucgg gcggcgcgga guuaacucag uagagcuggc uaagcaugua    300
gaaccgauag cggagagcug gcggacgggg guucaaaucc ccccggcucc acca          354

<210> SEQ ID NO 159
<211> LENGTH: 350
<212> TYPE: RNA
<213> ORGANISM: Pseudomonas fluorescens

<400> SEQUENCE: 159
cgccgguugc gaaccuuuag gugcaugccg aguugguaac agaacucgua aauccacugu    60
ugcaacuuuc uuaguugcca augacgaaac cuacggggaa uacgcucucg cugccguaagc   120 agccuuagcc cuucccuccu gguaccuucg gguccagcaa ucaucagggg augucuguaa    180
acccaaagug auugucauau agaacagaau cgccgugcag uacguugugg acgaagcggc    240
uaaaacuuac acaacucgcc caaagcaccc ugcccgucgg gucgcugagg guuaacuuaa    300
uagacacggc uacgcaugua guaccgacag cagaguacug gcggacgggg                350

<210> SEQ ID NO 160
<211> LENGTH: 323
<212> TYPE: RNA
<213> ORGANISM: Marinobacter hydrocarbonoclasticus

<400> SEQUENCE: 160
cgccggugac gaaccuuugg gugcaugccg agauggcagc gaaucgcuua aauccaaagc    60
ugcaacguaa uagucgcaaa cgacgaaaac uacgcacugg cggcguaagc cguccaguc    120 guccuggcug aggcgccuau aacucaguag caacauccca ggacgucauc gcuuauaggc    180
ugcuccguuc accagagcuc acgguguuc ggcuaagauu aaagagcucg ccucuugcac    240
```

```
ccugaccuuc gggucgcuug agguuaaauc aauagaagga cacuaagcau guagaccuca    300
aggccuagug cuggcggacg cgg                                           323
```

```
<210> SEQ ID NO 161
<211> LENGTH: 355
<212> TYPE: RNA
<213> ORGANISM: Shewanella putrefaciens

<400> SEQUENCE: 161
gggggcgauu cuggauucga caggauucac gaaacccugg gagcaugccg aggggcgguu    60
ggccucguaa aaagccgcaa aguuauaguu gcaaacgacg auaacuacgc ucuagccgcu   120
uaaugccgcu agccaucuac cacacgcuuu gcacaugggc aguggauuug auggucaucu   180
cacaucgugc uagcgaggga acccugucug ggggugaacc gcgaaacagu accggacuca   240
ccguguggga uccugucuuu cggaguucaa acgguuaaac aauagaaaga cuaagcaugu   300
agcgccuugg auguagguuu ucuggacgcg gguucaaguc ccgccgccuc cacca        355
```

```
<210> SEQ ID NO 162
<211> LENGTH: 314
<212> TYPE: RNA
<213> ORGANISM: Pseudoalteromonas haloplanktis

<400> SEQUENCE: 162
cggaauucaa gaagcccgag gugcaugucg aggugcgguu ugccucguaa aaagccgca    60 auuuaaagua aucgcaaacg acgauaacua cucucuagca gcuuaggcug gcuagcgcuc   120
cuuccaugua uucuugugga cuggauuuug gagugucacc cuaacaccug aucgcgacgg   180
aaacccuggc cgggguugaa gcguuaaaac uaagcgccu cgccuuuauc uaccguguuu    240
guccgggauu uaaagguuaa uuaaaugaca auacuaaaca guaguaccg acggucgagg    300 cuuuucggac gggg                                                    314
```

```
<210> SEQ ID NO 163
<211> LENGTH: 316
<212> TYPE: RNA
<213> ORGANISM: Aeromonas salmonicida

<400> SEQUENCE: 163
caagauucac gaaacccaag gugcaugccg aggugcggua ggccucguua acaaaccgca    60 aaaaauagu cgcaaacgac gaaaacuacg cacuagcagc uuaauaaccu gcauagagcc    120
cuucuacccu agcuugccug uguccagggg aaucggaagg ucauccuuca caggaucgug   180 uggaagccu gcucggggcg gaagcauuaa aaccaaucga gcuagucaau ucgggcgug    240 ucucuccgca gcgggguuggc gaauguaaag agugacuaag cauguaguac cgaggaugua   300
guaauuuugg acgggg                                                  316
```

```
<210> SEQ ID NO 164
<211> LENGTH: 363
<212> TYPE: RNA
<213> ORGANISM: Salmonella typhimurium

<400> SEQUENCE: 164 gggcugauu cuggauucga cgggauuugc gaaacccaag gugcaugccg aggggcgguu    60
ggccucguaa aaagccgcaa aaaauagc gcaaacgacg aaaccuacgc uuuagcagcu    120
uaauaaccug cuuagagccc ucucucccua gccuccgcuc uuaggacggg gaucaagaga   180
```

```
ggucaaacccc aaaagagauc gcgcggaugc ccugccuggg guugaagcgu uaaaacgaau      240 cagggcuaguc ugguagguggc guguccgucc gcaggugcca ggcgaugua aagacugacu      300 aagcauguag uaccgaggau guaggaauuu cggacgcggg uucaacuccc gccagcucca      360
cca                                                                    363

<210> SEQ ID NO 165
<211> LENGTH: 363
<212> TYPE: RNA
<213> ORGANISM: Escherichia coli

<400> SEQUENCE: 165
ggggcugauu cuggauucga cgggauuugc gaaacccaag gugcaugccg aggggcgguu       60
ggccucguaa aaagccgcaa aaauaguccg caaacgacga aaacuacgcu uuagcagcuu      120
aauaaccugc uuagagcccu cucucccuag ccuccgcucu uaggacgggg aucaagagag      180
gucaaaccca aaagagaucg cguggaagcc cugccugggg uugaagcguu aaaacuuaau      240
caggcuaguu uguuagugggc guguccgucc gcagcuggca agcgaaugua aagacugacu      300
aagcauguag uaccgaggau guaggaauuu cggacgcggg uucaacuccc gccagcucca      360
cca                                                                    363

<210> SEQ ID NO 166
<211> LENGTH: 364
<212> TYPE: RNA
<213> ORGANISM: Yersinia pestis

<400> SEQUENCE: 166
ggggcugauu cuggauucga cgggauucgc gaaacccaag gugcaugccg aggugcggug       60
gccucguaaa aaccgcaaaa aaauaguu gcaaacgacg aaaacuacgc acuagcagcu        120
uaauaaccug cuuagagccc ucucucccua gccuccgcuc uuaggacggg gaucaagaga      180
ggucaaaccu aaaagagcuc guguggaaac cuugccuggg guggaagcau uaaaacuaau      240
caggauaguu ugucaguagc guguccaucc gcagcuggcc ggcgaaugua augauuggac      300
uaagcaugua gugccgacgg guaguaauu ucggacgggg guucaaaucc ccccagcucc      360
acca                                                                   364

<210> SEQ ID NO 167
<211> LENGTH: 367
<212> TYPE: RNA
<213> ORGANISM: Vibrio cholerae

<400> SEQUENCE: 167
ggggcugauu caggauucga cgggaauuuu gcagucugag gugcaugccg aggugcggua       60
ggccucguua acaaaccgca aaaaauagu cgcaaacgac gaaaacuacg cacuagcagc      120
uuaauacccu gcuagagccc cuuccucccu agcuuccgcu uguaagacgg ggaaaucagg      180
aaggucaaac caaaucaagc uggcguggau uccccaccu gagggaugaa gcgcgagauc      240
uaauucaggu uagccauucg uuagcguguc gguucgcagg cgguggugaa auuaaagauc      300
gacuaagcau guaguaccaa agaugaaugg uuuucggacg ggguucaac uccccccagc      360 uccacca                                                                367

<210> SEQ ID NO 168
<211> LENGTH: 366
<212> TYPE: RNA
<213> ORGANISM: Haemophilus influenzae
```

```
<400> SEQUENCE: 168
ggggcugauu cuggauucga cgggauuagc gaagcccaag gugcacgucg aggugcggua      60
ggccucguaa auaaaccgca aaaaauacu cgcaaacgac gaacaauacg cuuuagcagc      120
uuaauaaccu gcauuuagcc uucgcgcucc agcuuccgcu cguaagacgg ggauaacgcg      180
gagucaaacc aaaacgagau cguguggaag ccaccguuug aggaucgaag cacuaaauug      240
aaucaaacua gcuuaaguuu agcgugucug ccgcaugcu uaagugaaau uaagacgag        300 acuaaacgug uaguacugaa gguagaguaa uuucggacgg gguucaacu ccccccagcu      360 ccacca                                                                 366

<210> SEQ ID NO 169
<211> LENGTH: 366
<212> TYPE: RNA
<213> ORGANISM: Haemophilus actinomycetemcomitans

<400> SEQUENCE: 169
ggggcugauu cuggauucga cgggauuagc gaagcccgaa gugcacgucg aggugcggua      60
ggccucguaa auaaaccgca aaaaauagu cgcaaacgac gaacaauacg cuuuagcagc      120
uuaauaaccu gccuuuagcc uucgcuccc agcuuccgcu cguaagacgg ggauaaagcg      180
gagucaaacc aaaacgagau cguguggaag ccaccguuug aggaucgaag cauuaaauua      240
aaucaaagua gcuuaauugu cgcgugucog ucagcaggau uaagugaauu uaagaccgg      300 acuaaacgug uagugcuaac ggcagaggaa uuucggacgg gguucaacu ccccccagcu      360 ccacca                                                                 366

<210> SEQ ID NO 170
<211> LENGTH: 354
<212> TYPE: RNA
<213> ORGANISM: Desulfovibrio desulfuricans

<400> SEQUENCE: 170
cggggacgug gaagccguag cggcaggucg aggcgccgcu ggccucguaa aaagcggcac      60
aaaaguaauu gccaacaacg auuacgacua cgcuuacgcu gccuauaac agcgaggcaa      120 ugaccguuua acgucgcgc cgaucagggc caugccugau aacccugauu cacuuaucag      180
gcuggcgaaa accggcucuc gccggggguuu uucgcgagga guuuaccggc gggauuccug      240
cguugugccu ggucagggc caacagcgcg gugaaauaca uacuugaccu aaaccguag      300 augcuucgug uggaauguuc ucggacgggg guucaaaucc ccccggcucc acca           354

<210> SEQ ID NO 171
<211> LENGTH: 366
<212> TYPE: RNA
<213> ORGANISM: Myxococcus xanthus

<400> SEQUENCE: 171
gggggcggaa aggauucgac gggggcauug aaguucgaga cgcgugccga gcuugucagg      60
uagcucguaa auucaacccg gcaaagacac aaaagccaac gacaacguug agcucgcgcu      120
ggcugccuaa aaacagccca uagugcgcgg ucccccgcc cucggccugu ggguugggga      180
cagaccguca uaaugcaggc uggcugccga gggugccugg acccgaggug gcgagaucuu      240
cccaggaccg gcucuaguca ucccguccgu gggagcccuca gggacguagc aaaucgcgga      300
cuacgcacgu agggucgaag agcggacggc uuucggacgg gguucgauu cccgccgccu      360
```

```
ccacca                                                                   366

<210> SEQ ID NO 172
<211> LENGTH: 346
<212> TYPE: RNA
<213> ORGANISM: Bdellovibrio bacteriovirus

<400> SEQUENCE: 172
gggggcggaa aggauucgac gggggugcug aagcauaagg agcauaccgg ggcggaugag    60
gaccucguua aaaacgucca cuuuguaauu ggcaacgauu acgcacuugc agcuuaauua   120
agcagcacga ucaaccuugu ggugguuccg cacuuggauu gaucgucauu uagggaccuc   180
ggcguguugg guuucucca gcagacaugc uuaaauuuac uggggagag gucuuaggga    240 uuuugucugu ggaagcccga ggaccaaucu aaaacacuga cuaaguaugu agcgccuuau   300
cguggaucau uugcggacgg ggguucgauu cccgccgccu ccacca                 346

<210> SEQ ID NO 173
<211> LENGTH: 386
<212> TYPE: RNA
<213> ORGANISM: Helicobacter pylori

<400> SEQUENCE: 173
ggggcugacu uggauuucga cagauuucuu gucgcacaga uagcaugcca agcgcugcuu    60
guaaaacagc aacaaaaaua acuguaaaca acacagauua cgcuccagcu uacgcuaaag   120
cugcgugagu uaaucuccuu uuggagcugg acugauuaga auucuagcg uuuuaaucgc    180 uccauaaccu uaagcuagac gcuuuuaaaa ggugguucgc cuuuuaaacu aagaaacaag   240
aacucuugaa acuaucucaa gguuuugaaa aguuggacca gagcuaguuu uaaggcuaaa   300
aaaccaacca auuuucuaag cauuguagaa guuuguguuu agggcaagau uuuuggacug   360
ggguucgauu ccccacagcu ccacca                                       386

<210> SEQ ID NO 174
<211> LENGTH: 359
<212> TYPE: RNA
<213> ORGANISM: Campylobacter jejuni

<400> SEQUENCE: 174
gggagcgacu uggcuucgac aggaguaagu cugcuuagau ggcaugucgc uuugggcaaa    60
gcguaaaaag cccaaauaaa auuaaacgca aacaacguua aauucgcucc ugcuuacgcu   120
aaagcugcgu aaguucaguu gagccugaaa uuuaagucau acuaucuagc uuaauuuucg   180
gucauuuuug auaguguagc cuugcguuug acaagcguug aggugaaaua aagcuuagc    240 cuugcuuuug aguuuggaa gaugagcgaa guagggugaa guagucaucu uugcuaagca   300
uguagagguc uuuguggggau uauuuugga caggggguucg auuccccucg cuuccacca   359

<210> SEQ ID NO 175
<211> LENGTH: 355
<212> TYPE: RNA
<213> ORGANISM: Sulfurospirillum deleyianum

<400> SEQUENCE: 175
caggaguagu uuuagcuuau ggcugcaugu cgggagugag ggucuuccgu uacacaaccu    60
ucaaacaaua acugcuaaca acaguaacua ucguccugcu uacgcgcuag cugcguaagu   120
uuaacaaaua auggacugcu cuccccuuug augcuaucuu aggaggucuu ggagaguauc   180
auagauuuga uagcuauauu acaugaacgc cuuuacaugu aaugaaguua aaggcucguu   240
```

```
uucguaguuu ucugauuguu guacgaagca aaauuaaaca cuaucaacaa uaucuaagca      300
uguagacguc auaggugcu auuuuuggac ugggguucaa cucccgccag cucca            355
```

EUBACTERIAL TMRNA SEQUENCES AND USES THEREOF

CROSS-REFERENCE TO RELATED APPLICATIONS

The present application is division of U.S. patent application Ser. No. 11/329,230 filed on 11 Jan. 2006, which in turn in a division of U.S. patent application Ser. No. 09/958,206 filed on 20 Feb. 2002, now U.S. Pat. No. 7,115,366, which in turn is a national stage filing under 35 U.S.C. §371 of International patent application No. PCT/U.S. 00/08988 filed on 6 Apr. 2000, which in turn is related to and claims priority under 35 U.S.C. §119(e) to U.S. provisional patent application Ser. No. 60/128,058 filed on 7 Apr. 1999. Each of these applications is incorporated herein by reference.

This application was made with Government support under Grant No. GM 48152, funded by the National Institutes of Health, Bethesda, Md. The Government has certain rights in this invention.

BACKGROUND OF THE INVENTION

The present invention is directed to eubacterial tmDNA sequences and the corresponding tmRNA sequences. The present invention is further directed to alignments of eubacterial tmDNA sequences and use of the sequences and sequence alignments for the development of antibacterial drugs. The present invention is also directed to the use of the sequences for the development of diagnostic assays.

The publications and other materials used herein to illuminate the background of the invention or provide additional details respecting the practice are incorporated by reference, and for convenience are respectively grouped in the appended List of References.

Eubacterial tmRNAs (10Sa RNAs) are unique since they function, at least in E. coli, both as tRNA and as mRNA (for a review, see Muto et al., 1998). These ≈360±10% nucleotide RNAs are charged with alanine at their 3'-ends (Komine et al., 1994; Ushida et al., 1994) and also have a short reading frame coding for 9 to 27 amino acids depending on the bacterial species. E. coli tmRNA mediates recycling of ribosomes stalled at the end of terminatorless mRNAs, via a trans-translation process (Tu et al., 1995; Keiler et al., 1996; Himeno et al., 1997). In E. coli, this amino acid tag is co-translationally added to polypeptides synthesized from mRNAs lacking a termination codon, and the added 11 amino acid C-terminal tag makes the protein a target for specific proteolysis (Keiler et al., 1996).

Structural analyses based on phylogenetic (Felden, et al., 1996; Williams and Bartel, 1996) and probing (Felden et al., 1997; Hickerson et al., 1998) data have led to a compact secondary structure model encompassing 6 helices and 4 pseudoknots. tmRNAs have some structural similarities with canonical tRNAs, especially with tRNA acceptor branches. E. coli tmRNA contains two modified nucleosides, 5-methyluridine and pseudouridine, located in the tRNA-like domain of the molecule, in a seven-nucleotide loop mimicking the conserved sequence of T loops in canonical tRNAs (Felden et al., 1998).

Fifty-three tmRNA sequences are now known from both experimental data and Blast searches on sequenced genomes (summarized in Williams, 1999; Wower and Zwieb, 1999). These sequences cover only 10 phyla, less than one third of the known bacterial taxa. It is desired to determine additional tmRNA sequences and to use the tmRNA sequences for drug development.

SUMMARY OF THE INVENTION

The present invention relates to eubacterial tmDNA sequences and the corresponding tmRNA sequences. The present invention further relates to alignments of eubacterial tmDNA sequences and use of the sequences and sequence alignments for the development of antibacterial drugs.

In one aspect of the present invention, an extensive phylogenetic analysis was performed. Fifty-eight new tmDNA sequences including members from nine additional phyla were determined. Remarkably, tmDNA sequences could be amplified from all species tested apart from those in the alpha-Proteobacteria. This aspect of the invention allowed a more systematical study of the structure and overall distribution of tmRNA within eubacteria In a second aspect of the invention, alignments are made with the newly isolated tmDNA sequences and previously disclosed tmRNA sequences.

In a third aspect of the invention, the alignments of the tmRNA sequences allow the identification of targets for development of antibacterial drugs.

In a fourth aspect of the invention, the novel tmDNA or tmRNA sequences of the present invention are used to develop diagnostic assays, such as amplification-based assays, for the bacterial species disclosed herein.

BRIEF DESCRIPTION OF THE FIGURES

FIGS. 3A, 3B and 3C show the sequence alignment, structural domains and structural features for the tmRNA of several species of Firmicutes. The tmRNA sequences are set forth in SEQ ID NOs:67-87.

FIGS. 4A and 4B show the sequence alignment, structural domains and structural features for the tmRNA of several species of Thermophiles. The tmRNA sequences are set forth in SEQ ID NOs:88-99.

FIGS. 7A-1, 7A-2, 7B, 7C and 7D show the sequence alignment, structural domains and structural features for the tmRNA of several species of *Mesophiles* (7A-1, 7A-2, 7C, 7D) and environmental sludge (7B). The tmRNA sequences of the *Mesophiles* are set forth in SEQ ID NOs:118-123 and 125-128, and the tmRNA sequence of the environmental sludge is set forth in SEQ ID NO:124.

FIGS. 9A and 9B show the sequence alignment, structural domains and structural features for the tmRNA of several species of *Pourpres* beta. The tmRNA sequences are set forth in SEQ ID NOs:143-154.

FIGS. 10A, 10B and 10C show the sequence alignment, structural domains and structural features for the tmRNA of several species of *Pourpres* gamma. The tmRNA sequences are set forth in SEQ ID NOs:155-169.

DETAILED DESCRIPTION OF THE INVENTION

Figure 1A:
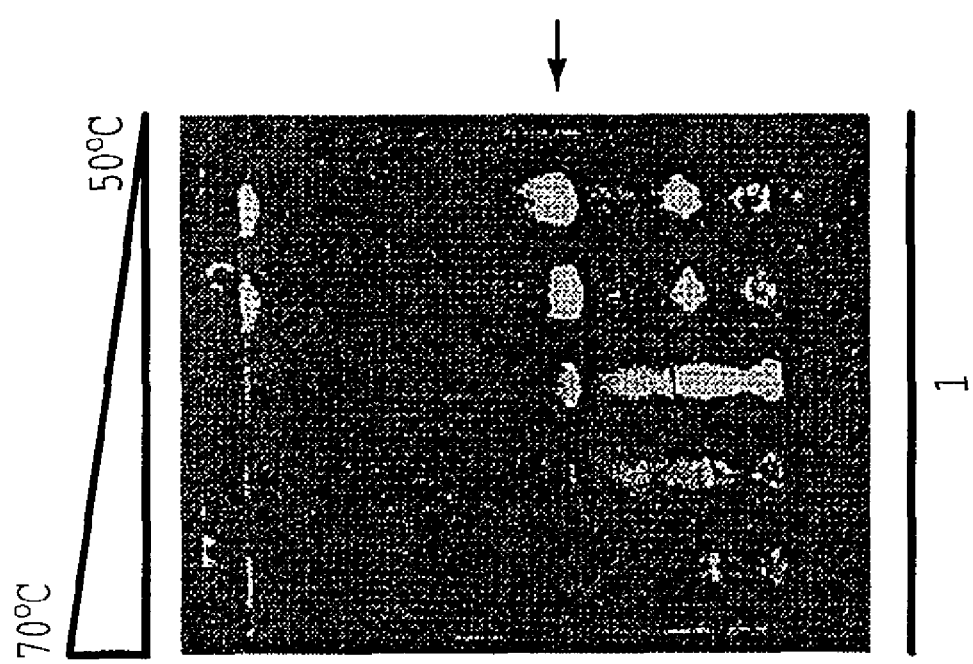
FIGS. 1A-1B show the effect of the annealing temperature (FIG. 1A) and magnesium concentration (FIG. 1B) on amplifying eubacterial tmRNA genes from genomic DNAs using PCR. A: Varying the annealing temperature from 50° to 70° C. during the PCR amplification of Thermus aquaticus(1). B; Varying the magnesium concentration to amplify tmDNA genes from Thermus aquaticus (1), negative effect of increasing the magnesium concentration), Acholeplasma laidlawii (2), positive effect of increasing the magnesium concentration, the upper band is the tmDNA gene) and from Mycoplasma salivarium (3), no discernible effect of magnesium ions in that concentration range). The arrows point toward the 4 novel tmDNA genes that have been sequenced.

The present invention is directed to eubacterial tmDNA sequences and the corresponding tmRNA sequences. The present invention is further directed to alignments of eubacterial tmDNA sequences and use of the sequences and sequence alignments for the development of antibacterial drugs.

The novel eubacterial tmDNA sequences determined in accordance with the present invention are set forth in Tables 1-58, below. The alignment of tmRNA sequences is shown in FIGS. 3A-11B, which also show the structural domains and structural features of the tmRNA. The present invention also includes the tmRNA sequences set forth in these figures to the extent they differ from the sequences set forth in Tables 1-58.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria. Thus, the present invention is further directed to the development of drugs for the therapeutic treatment of bacteria, generically or specifically. Suitable drugs are developed on the basis of the tmRNA sequences as described herein.

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. Since these pseudoknots are not found in all canonical transfer RNAs, they can also be targeted with specific drugs. Disruption of either PK1 or PK2 or PK3 with a specific drug would lead to inactive tmRNA molecules in vivo.

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding (such as shown for *Escherichia coli*; Matveeva et al., 1997), and thus, is also available for interaction with other drugs. Moreover, the coding sequence is a critical functional domain of the molecule in its quality-control mechanism in cells.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 base-pairs instead of 5 in the other species;

(3) for two sequences of chlorobium as well as *Bacteroides thetaiotaomicron* and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future antibacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

It has recently been discovered that even the alpha-proteobacteria possess tmRNA genes. These genes are permuted and are made in two parts, connected via a processed linker. These tmRNA gene sequences from alpha-proteobacteria were not found in the course of the present invention because usual PCR methods could not amplify them.

Recent reports have shown that whereas the gene encoding tmRNA is non-essential in *E. coli* (does not kill the bacteria when disrupted), it is indeed essential in *Neisseria gonorrheae* (Huang et al., 2000). Also, tmRNA is directly involved in *Salmonella typhymurium* pathogenticity (Julio et al., 2000).

In summary, tmRNA genes are present in all eubacterial genomes, with no exceptions, but are not present in any genomes from archebacteries or eukaryotes, with the exception of some chloroplasts. The very specific location of tmRNA genes within one of the three main kingdoms of life make them ideal targets for the design of novel antibiotics that will, in principle, interfere very weakly with human biochemistry, compared to usual antibiotics. For a recent review about designing novel antibiotics, see Breithaupt (1999).

The present invention is also directed to diagnostic assays and kits for the detection of bacterial infection, particularly infections caused by bacterial agents disclosed herein. In one embodiment, the coding sequence of each bacterial species is used to design specific primers for use in amplification-based diagnostic assays for infectious diseases. Specific primers are designed in accordance with well known techniques, and such design is readily done by a skilled artisan. Amplification-based diagnostic assays are performed in accordance with conventional techniques well known to skilled artisans. Examples of amplification-based assays include, but are not limited to, polymerase chain reaction (PCR) amplification, strand displacement amplification (SDA), ligase chain reaction (LCR) amplification, nucleic acid sequence based amplification (3SR or NASBA) and amplification methods based on the use of Q-beta replicase.

Drugs which target the sequences described herein are active agents can be formulated in pharmaceutical compositions, which are prepared according to conventional pharmaceutical compounding techniques (*Remington's*, 1990). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences* (18).

Alternatively, targeting therapies may be used to deliver the active agent more specifically to certain types of cell, by the use of targeting systems such as antibodies or cell-specific ligands. Targeting may be desirable for a variety of reasons, e.g. if the agent is unacceptably toxic, or would otherwise require too high a dosage, or otherwise be unable to enter the target cells.

Antisense active agents can also be delivered by techniques described in U.S. Pat. Nos. 5,811,088; 5,861,290 and 5,767,102.

EXAMPLES

The present invention is further detailed in the following Examples, which are offered by way of illustration and are not intended to limit the invention in any manner. Standard techniques well known in the art or the techniques specifically described below are utilized.

Example 1

Materials and Methods

1. Extraction of Genomic DNA

Bacterial genomic DNAs were prepared from ≈10 mg freeze-dried cells provided from ATCC (American Type Culture Collection, Virginia, USA). Cell pellets were resuspended in 750 μL of lysis buffer (50 mM Tris (pH 8.0), 50 mM EDTA and 20% sucrose). 150 μL of a 10 mg/mL solution of lysozyme was mixed and let stand at room temperature for 15 min. 150 μL of 1% SDS was added and let stand at room temperature for 15 minutes. Four to five phenol/chloroform extractions were performed, until the sample was clear and there was no interphase. Two to five μL of a 10 mg/mL solution of RNase DNase-free was added and incubated at room temperature for 30 minutes. After a phenol/chloroform extraction of the enzyme, the genomic DNA was precipitated with $\frac{1}{10}$ volume of 3M NaOAc (pH 5.5) and 1 volume isopropanol, and stored at −20° C. for 2 hours. After centrifugation, the genomic DNAs were washed with 70% ethanol, vacuum-dried and diluted in sterile water to a final concentration of 10 ng/μL.

2. Primer Sets for PCR Reactions

The following primer sets were used during the PCR:

```
primer set A (based on E. coli tmRNA termini):
5'-GGG GCT GAT TCT GGA TTC GAC-3'     (SEQ ID NO: 1)
and

5'-TGG AGC TGG CGG GAG TTG AAC-3';    (SEQ ID NO: 2)

primer set B (based on T. neapolitana tmRNA
termini):
5'-GGG GGC GGA AAG GAT TCG ACG-3'     (SEQ ID NO: 3)
```

-continued and

5'-TGG AGG CGG CGG GAA TCG AAC-3'; (SEQ ID NO: 4)

primer set C (based on *M. pneumoniae* tmRNA termini):
5'-GGG GAT GTC ATG GTT TTG ACA-3' (SEQ ID NO: 5)
and 5'-TGG AGA TGG CGG GAA TCG AAC-3'; (SEQ ID NO: 6)
and primer set D (based on *C. tepidum* tmRNA termini):
5'-GGG GAT GAC AGG CTA TCG ACA-3' (SEQ ID NO: 7)
and

5'-TGG AGA TGG CGG GAC TTG AAC-3'. (SEQ ID NO: 8)

3. PCR Reaction

Sequences of tmRNA genes were obtained by polymerase chain reaction (PCR) in 25 µL using 40 ng of genomic DNA per reaction. The following general scheme was utilized for all of the sequences:

(a) 94° C. to 96° C. for 4 min. (first denaturation of genomic DNAs, done only once); then (b) 35 to 40 PCR cycles with 2.5 to 5 Units of Taq DNA polymerase in a 25 µL reaction volume, according to the following scheme (40 ng of genomic DNAs/PCR reaction):

1. denature at 94° to—96° C. for 25 to 30 sec;
2. anneal at 44° to 55° C. for 20 to 30 sec; and
3. extension at 72° C. for 10 sec.

The magnesium conc. was optimized for each phyla from 3.5 to 13.5 mM.

4. Elution of Amplified DNAs

The various PCR-amplified tmDNA bands were gel purified (5% PAGE), stained (ethidium bromide staining), cut using a sterile razor blade, and shaken over-night (passive elution, using a vibrator) in a 350 µl solution containing 10 mM Tris-HCl buffer (pH 8.1). The following day, the PCR amplified tmDNAs were ethanol precipitated, washed in 70% ETOH, vacuum dried and the DNA pellets were dissolved in 18 µl of RNase-DNase free sterile water.

5. DNA Sequencing

Six µL of amplified DNAs were added to 3.2 picomoles of the primer that was used in the PCR. To verify the novel tmDNA sequences, each of the two primers were used independently to sequence each of the two PCR-amplified DNA strands. Some tmDNAs were already engineered at their 5'-ends with a T7 promoter, to be able to transcribe directly the tmDNAs into tmRNAs by in vitro transcription.

Dye terminator sequencing was achieved at the DNA sequencing facility of the Human Genetics Institute. In addition to novel tmRNA sequences that are not available publicly, several tmDNA sequences that were already known have been verified and several sequencing mistakes have been found and corrected (especially for *Alcaligenes eutrophus* tmRNA).

Example 2

Amplification Reactions for Eubacterial tmDNA

Eubacterial tmDNA was amplified by PCR in accordance with Example 1, using the following conditions.

*Acidobacterium:*
Primer Set B; Annealing temp. during PCR: 53° C. for 20 sec; $Mg^{2+}$ conc.: 4.5 mM.

*Coprothermobacter:*
Primer Set B; Annealing temp. during PCR: 55° C. for 30 sec; $Mg^{2+}$ conc.: 5.5 mM.

*Cytophagales:*
Primer Set A; Annealing temp. during PCR: 46° C. for 30 sec; $Mg^{2+}$ conc.: 4.5 mM.

*Dictyoglomus:*
Primer set B; Annealing temp. during PCR: 55° C. for 30 sec; $Mg^{2+}$ conc.: 4.5 mM.

Environmental Samples:
Sludge DNA
Primer set C; Annealing temp. during PCR: 51° C. for $20^{sec}$; $Mg^{2+}$ conc.: 13.5 mM.
Rumenal fluid DNA
Primer set D; Annealing temp. during PCR: 50° C. for 30 sec; $Mg^{2+}$ conc.: 9.5 mM.

*Fibrobacter:*
Primer set A; Annealing temp. during PCR: 51° C.; $Mg^{2+}$ conc.: 3.5 mM.

*Firmicutes:*
Fusobacteria:
Primer set A; Annealing temp. during PCR: 52° C.; $Mg^{2+}$ conc.: 5.5 mM.
High G-C:
Primer set A; Annealing temp. during PCR: 50-55° C.; $Mg^{2+}$ conc.: 4.5 mM.
Low G-C:
Primer sets A or B; Annealing temp. during PCR: 52° C.; $Mg^{2+}$ conc.: 5.5 to 7.5 mM.
Mycoplasmes:
Primer set A; Annealing temp. during PCR: 52° C.; $Mg^{2+}$ conc.: 3.5 to 5.5 mM.

Green Non-Sulfur:
Primer sets A or B; Annealing temp. during PCR: 46 to 52° C.; $Mg^{2+}$ conc.: 4.5 mM.

Green Sulfur:
Primer set A; Annealing temp. during PCR: 46° C.; $Mg^{2+}$ conc.: 4.5 mM.

*Planctomycetales:*
Primer set A; Annealing temp. during PCR: 48 to 52° C.; $Mg^{2+}$ conc.: 7.5 mM.

Proteobacteria:
beta:
Primer sets A and/or B; Annealing temp. during PCR: 50° C. for 25 sec; $Mg^{2+}$ conc.: 3.5 mM.
delta:
Primer set B; Annealing temp. during PCR: 55° C.; $Mg^{2+}$ conc.: 3.5 to 4.5 mM.
epsilon:
Primer set A; Annealing temp. during PCR: 46° C. for 30 sec; $Mg^{2+}$ conc.: 3.5 mM. gamma:
Primer set A; Annealing temp. during PCR: 44 C for 30 sec; $Mg^{2+}$ conc.: 5.5 mM.

*Spirochetes:*
Primer set A; Annealing temp. during PCR: 52° C.; $Mg^{2+}$ conc.: 4.5 mM.

*Thermodesulfobacterium:*
Primer set B; Annealing temp. during PCR: 55° C.; $Mg^{2+}$ conc.: 5.5 mM.

*Thermotogales:*
Primer set B; Annealing temp. during PCR: 46° C.; Mg²⁺ conc.: 7.5 mM.

*Deinococcales:*
Primer set B; Annealing temp. during PCR: 52° C.; Mg²⁺ conc.: 3.5 mM.

*Verrucomicrobia:*
Primer set A; Annealing temp. during PCR: 53° C. for 25 sec; Mg²⁺ conc.: 3.5 mM.

Example 3

Amplification of Eubacterial tmDNA

Figure 1B:
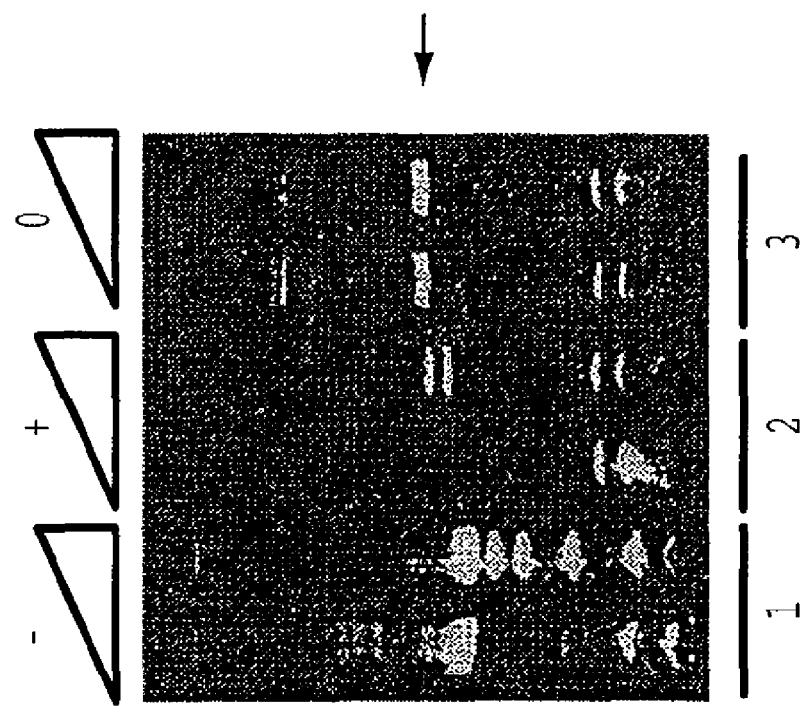

Specific PCR amplification of tmRNA genes was achieved for both thermophilic and mesophilic eubacterial tmRNA genes. For the novel tmDNA genes found in thermophiles, both the magnesium concentration and the annealing temperature (FIG. 1A) were optimized. As shown in FIG. 1A, a specific amplification of *Thermus aquaticus* tmDNA was observed with an annealing temperature around 50° C., whereas at higher temperatures there is a gradual decrease in the amount of amplified tmDNA. For mesophiles, the magnesium concentration during PCR was critical (FIG. 1B), but the annealing temperature could vary from 44° C. to 60° C. without significant effects on the amplification. FIG. 1B shows various effects of increasing the magnesium concentration on the PCR amplification of three novel eubacterial tmDNA genes. Increasing magnesium concentration from 3.5 mM to 5.5 mM has either a negative (FIG. 1B, panel 1), a positive (FIG. 1B, panel 2) or no effect on specifically amplifying eubacterial tmDNA genes.

Figure 2:
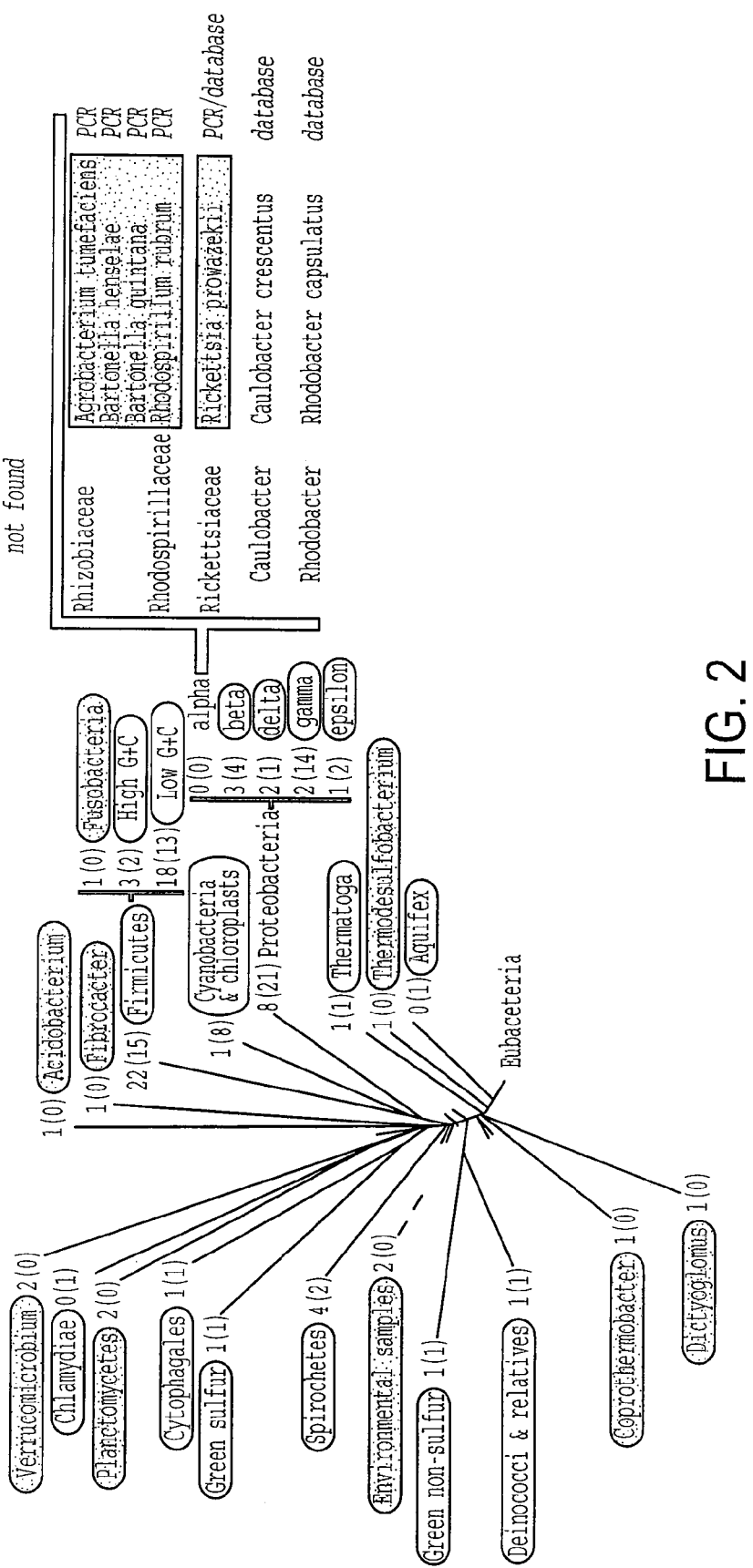
FIG. 2 shows the distribution of tmDNA sequences within eubacterial genomes. The circled phyla or subgroups contain tmDNA sequences and those shaded are new members of this category. The numbers shown close to each phylum are the 51 tmDNA sequences that have are disclosed herein and the numbers in parenthesis are the 53 tmDNA sequences that were previously known (summarized in Williams, 1999; Wower and Zwieb, 1999). The environmental samples are indicated with a dashed line as their connection to the tree is unknown. The 5 alpha-Proteobacteria in which tmDNA sequences were not detected by PCR analysis are labeled "PCR" and the 3 analyzed by Blast search of the complete, or nearly complete, sequenced genomes are labeled "database".
Figure 3A:
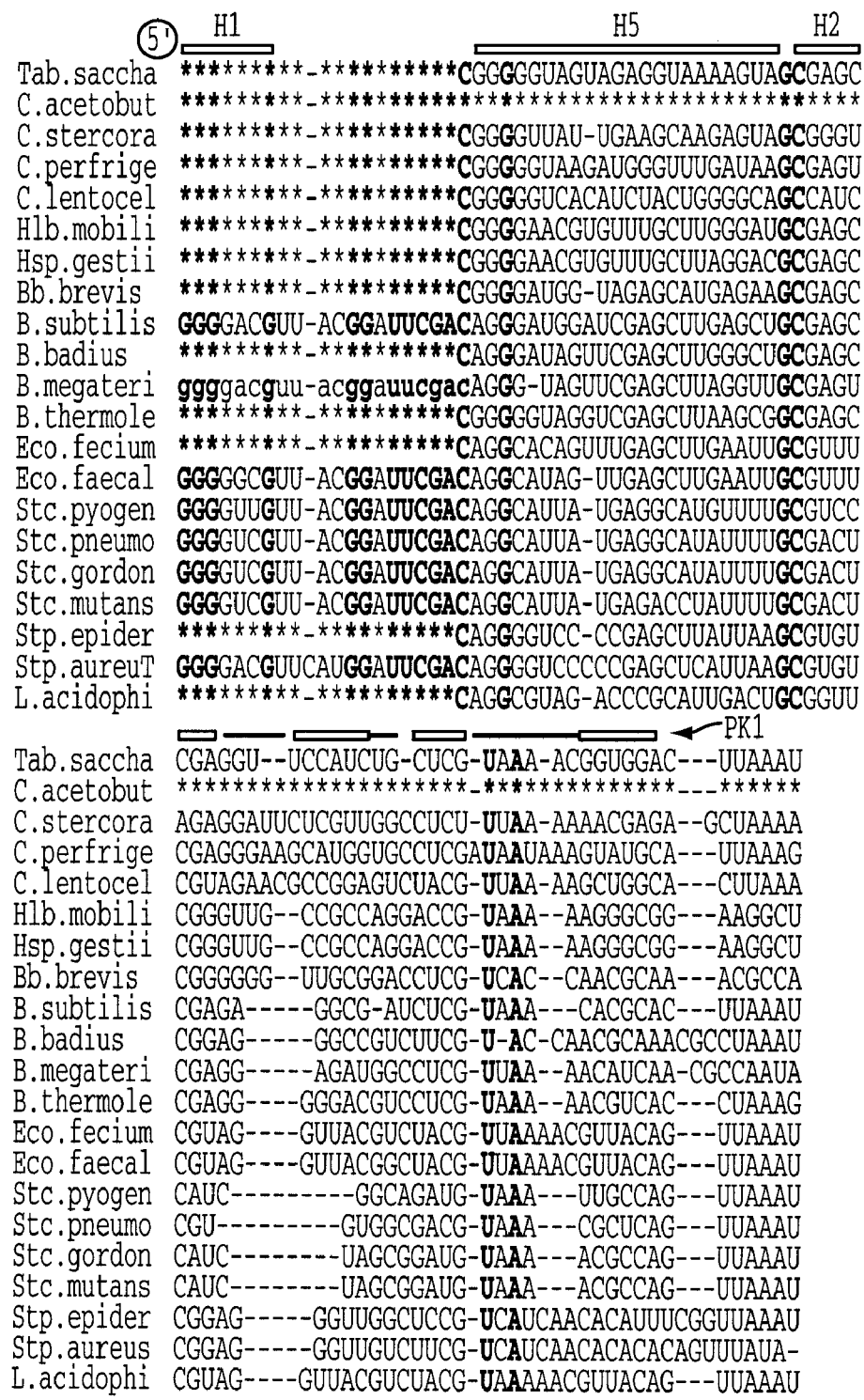
Figure 4A:
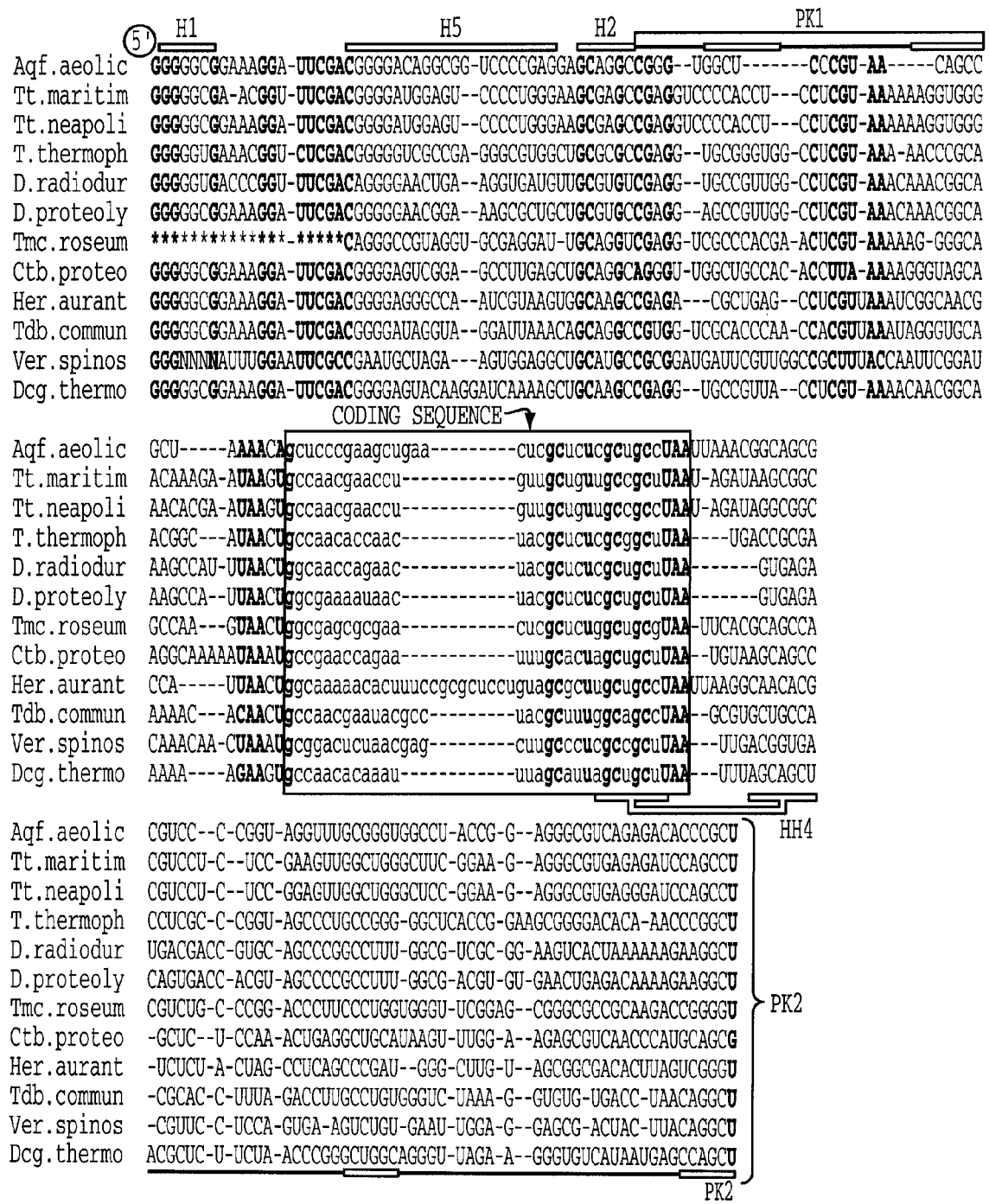
Figure 5A:
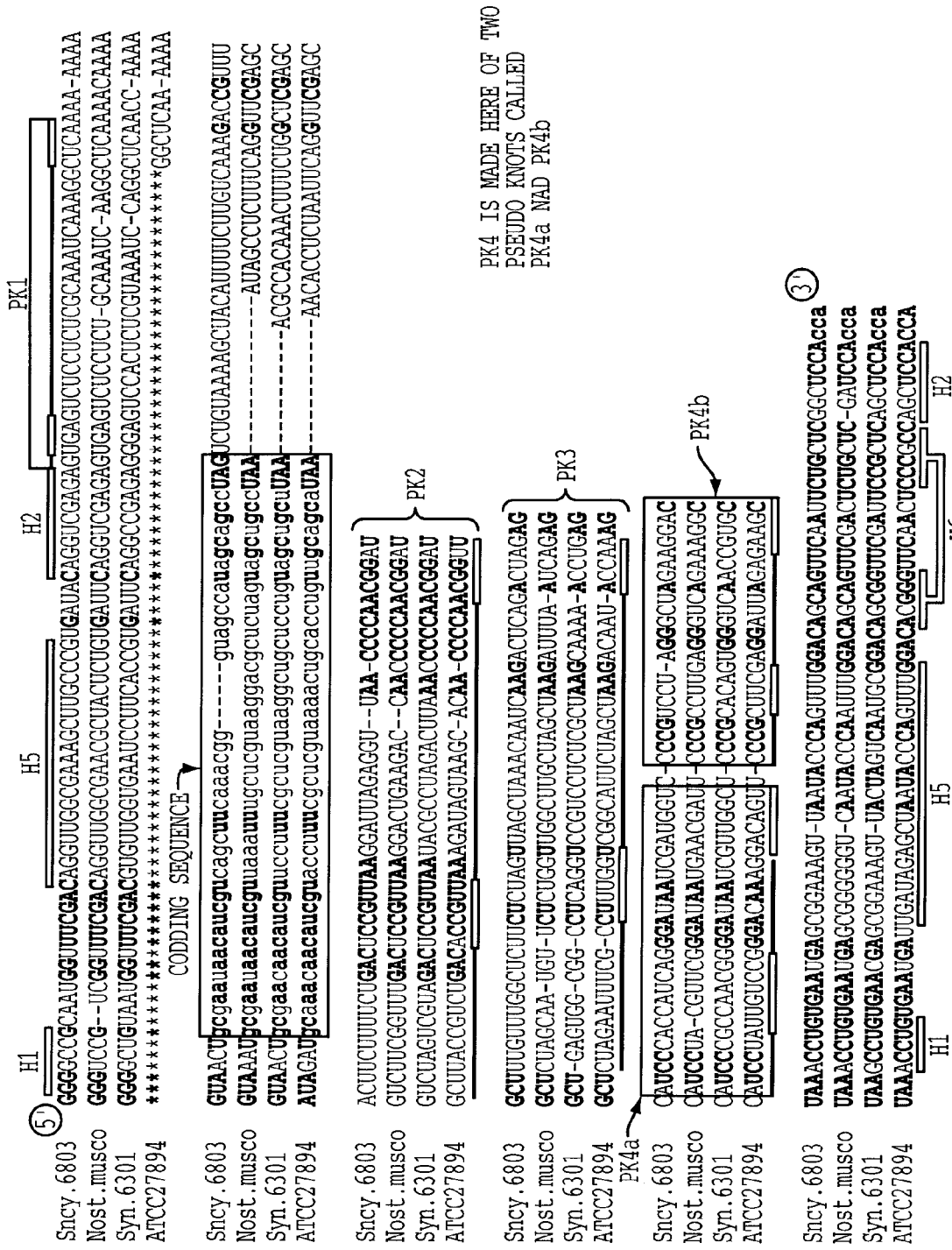
FIGS. 5A and 5B show the sequence alignment, structural domains and structural features for the tmRNA of several species of Cyanobacteries (5A) and chloroplasts (5B). The tmRNA sequences of the Cyanobacteries are set forth in SEQ ID NOs:100-103, and the tmRNA sequences of the chloroplasts are set forth in SEQ ID NOs:104-108.
Figure 5B:
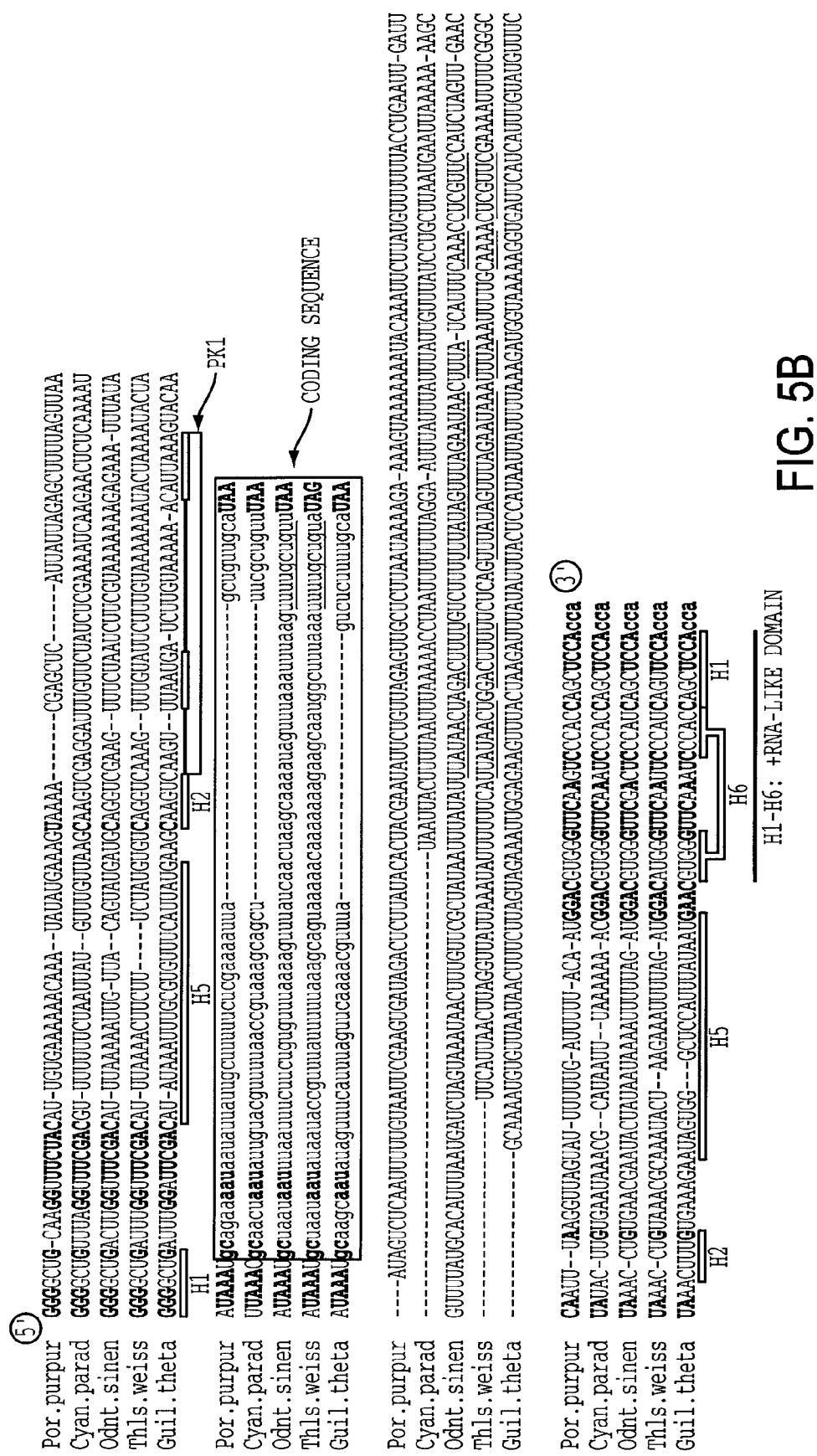
Figure 6A:
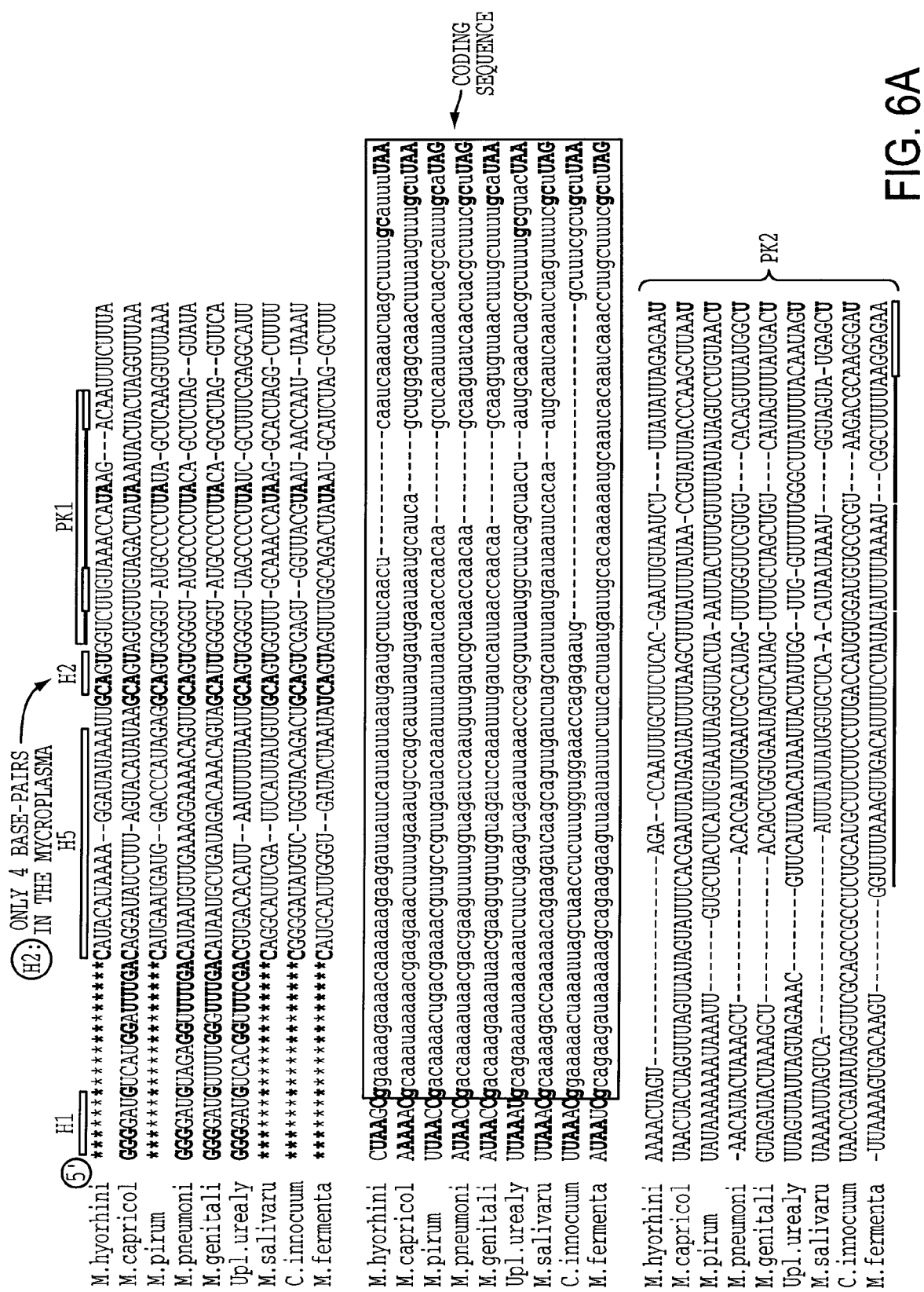
FIGS. 6A and 6B show the sequence alignment, structural domains and structural features for the tmRNA of several species of *Mycoplasmes*. The tmRNA sequences are set forth in SEQ ID NOs:109-117.
Figure 6B:
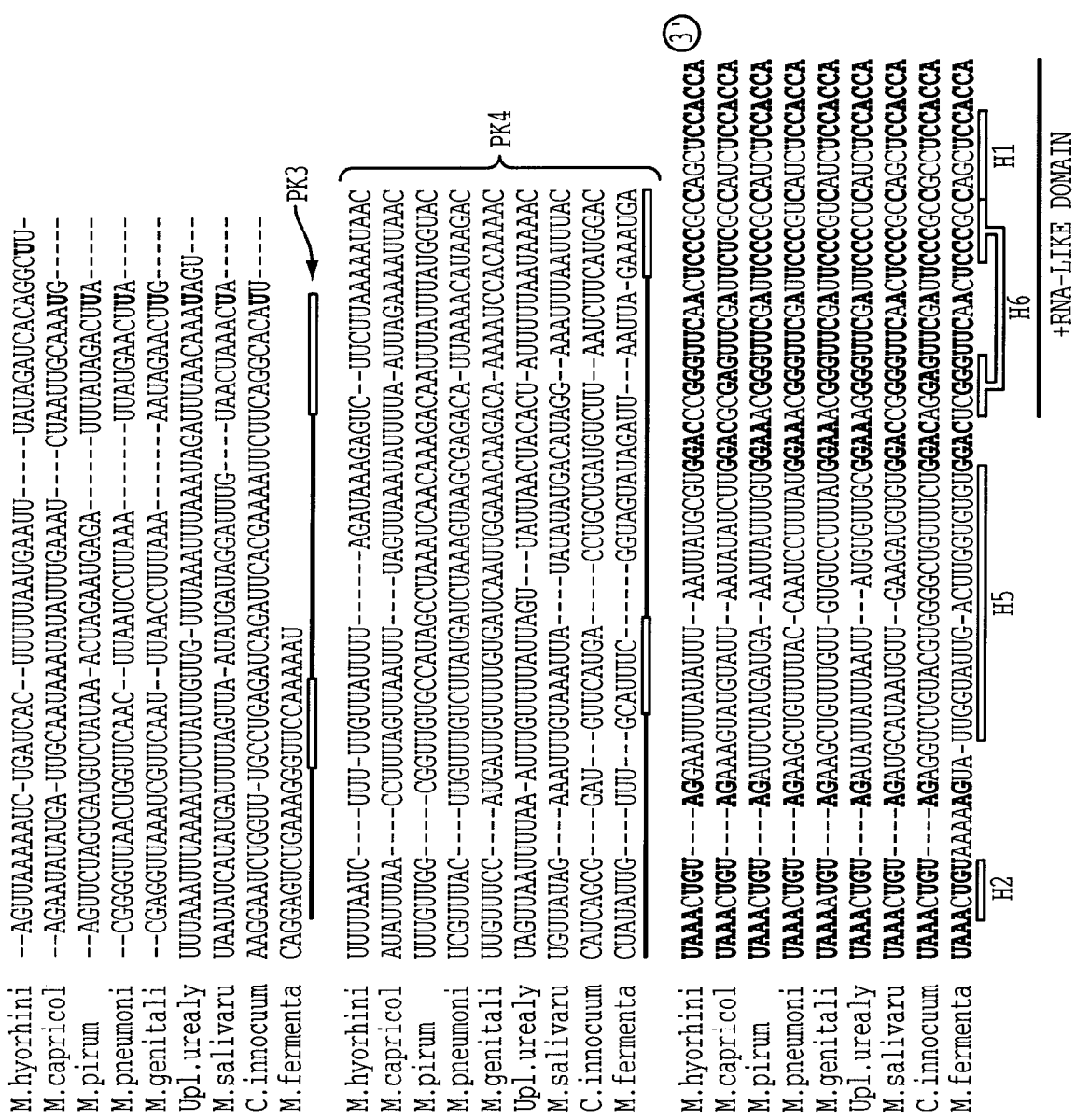
Figures 1, 7A:
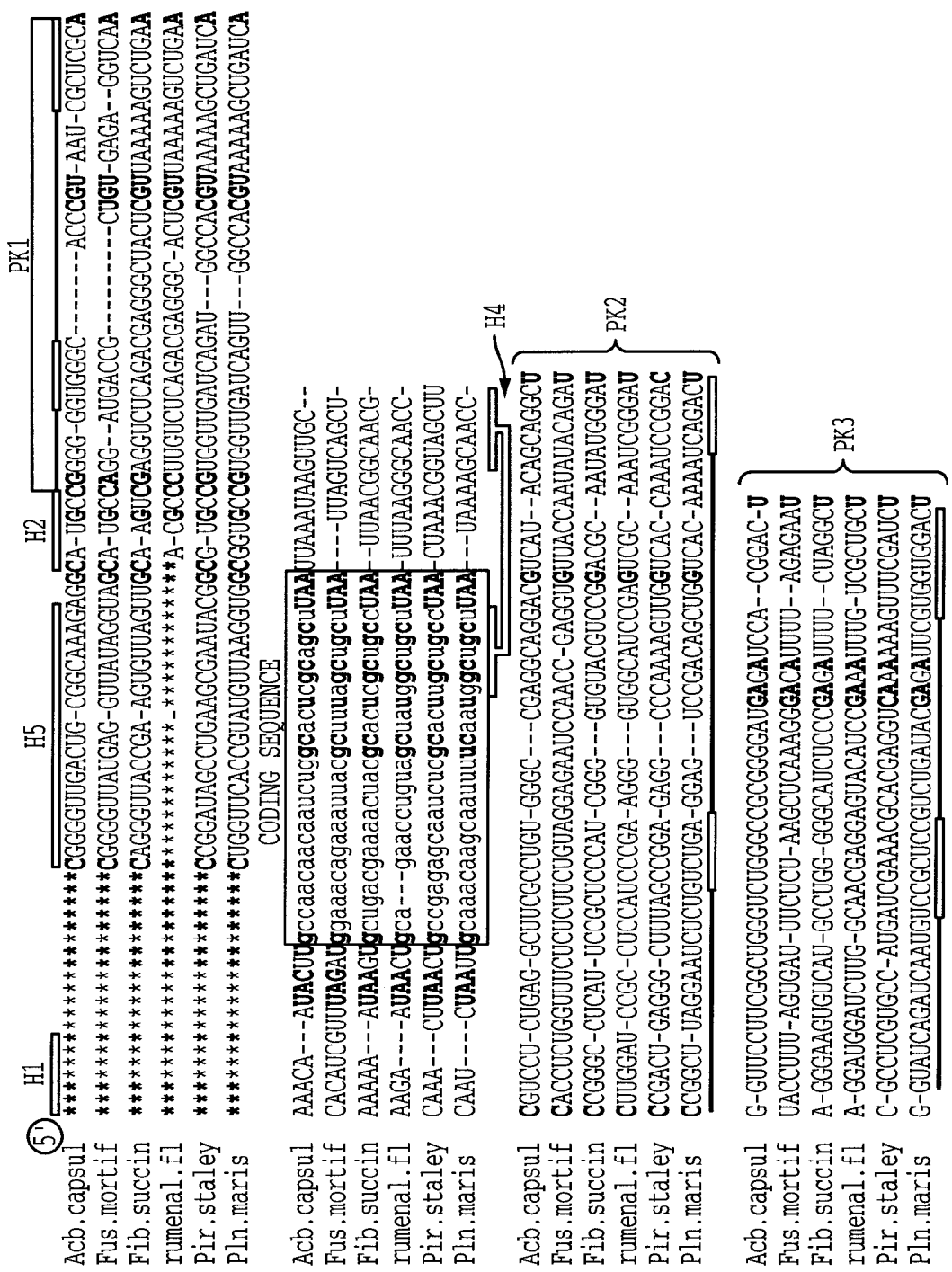
Figure 7C:
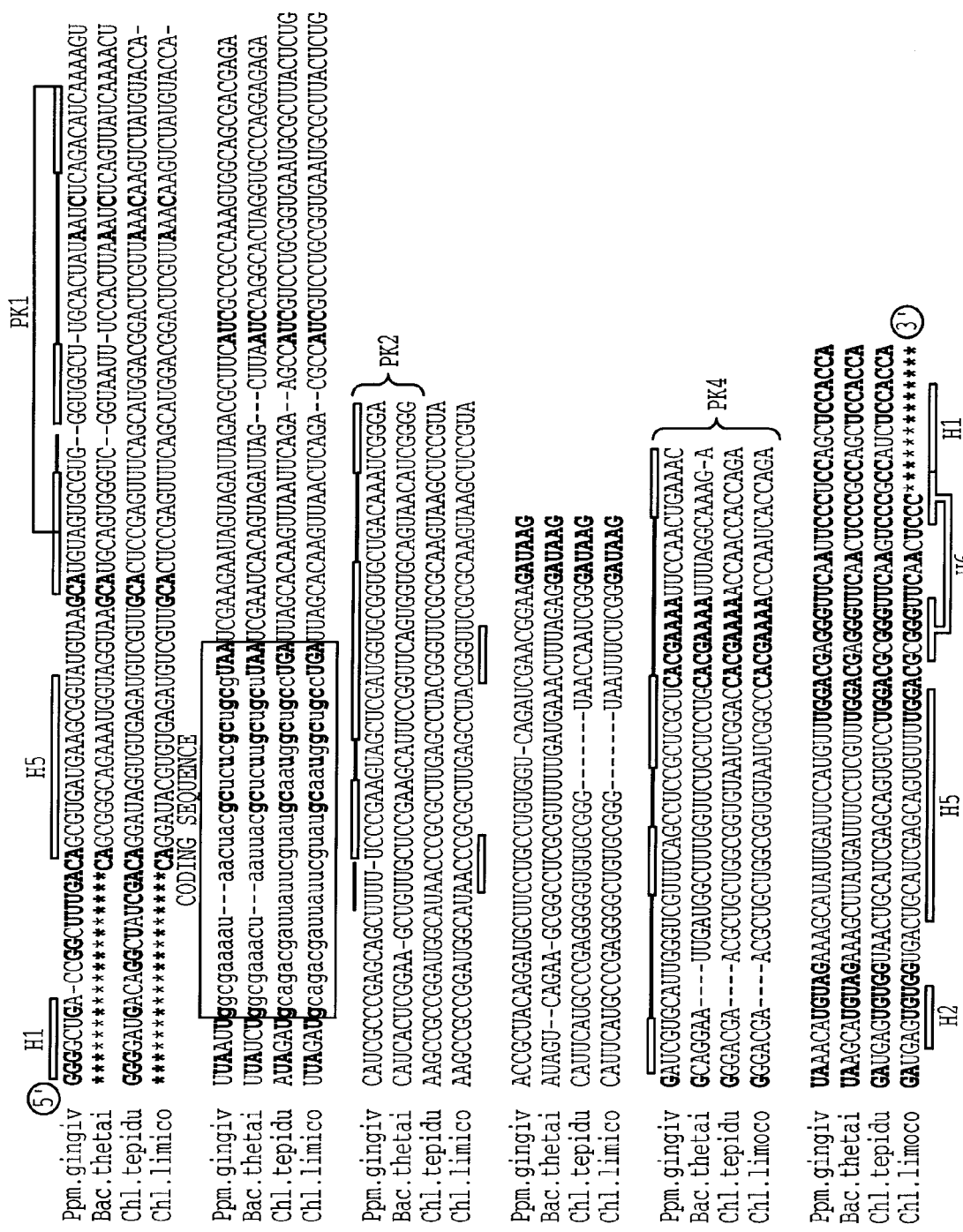
Figure 7D:
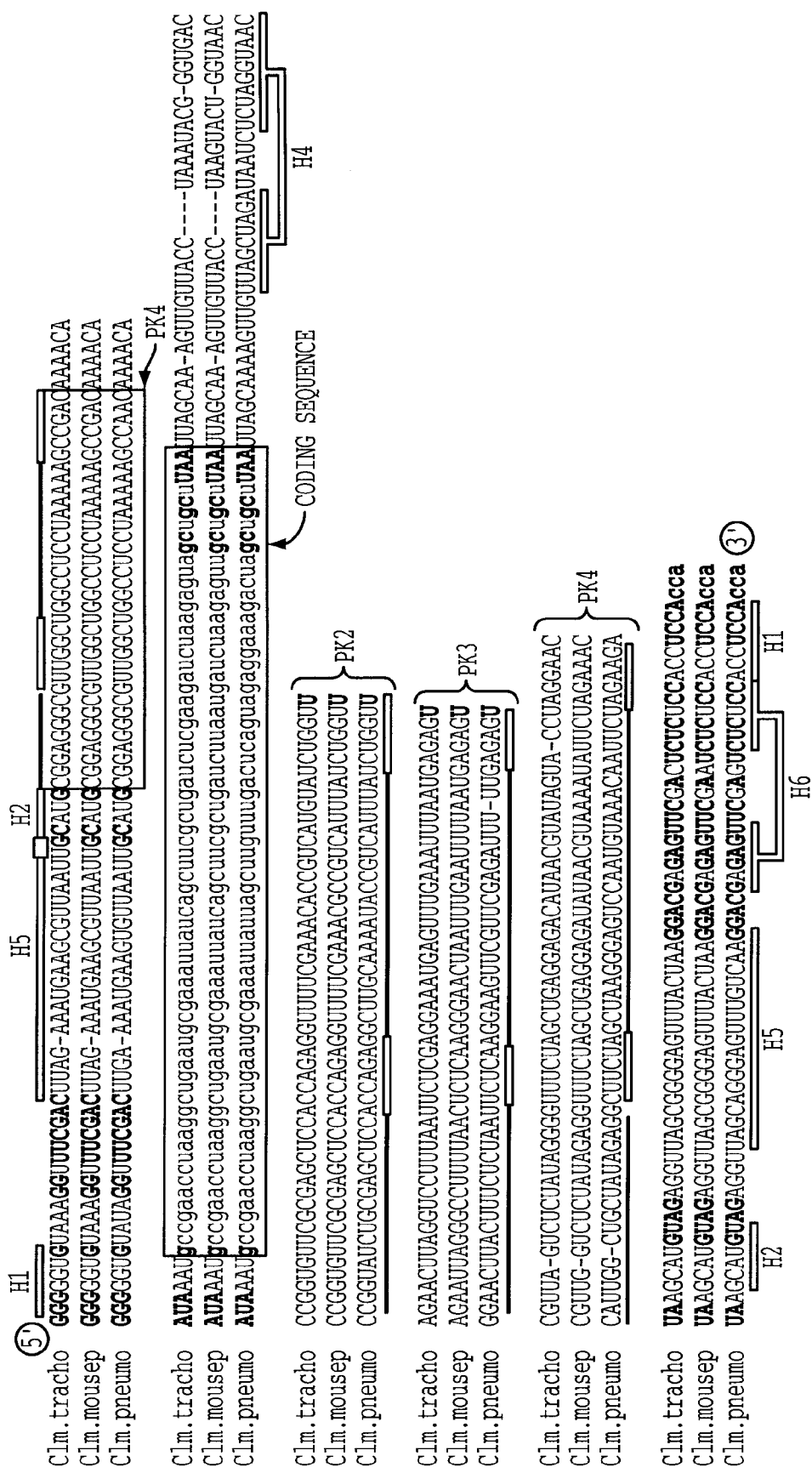
Figure 8A:
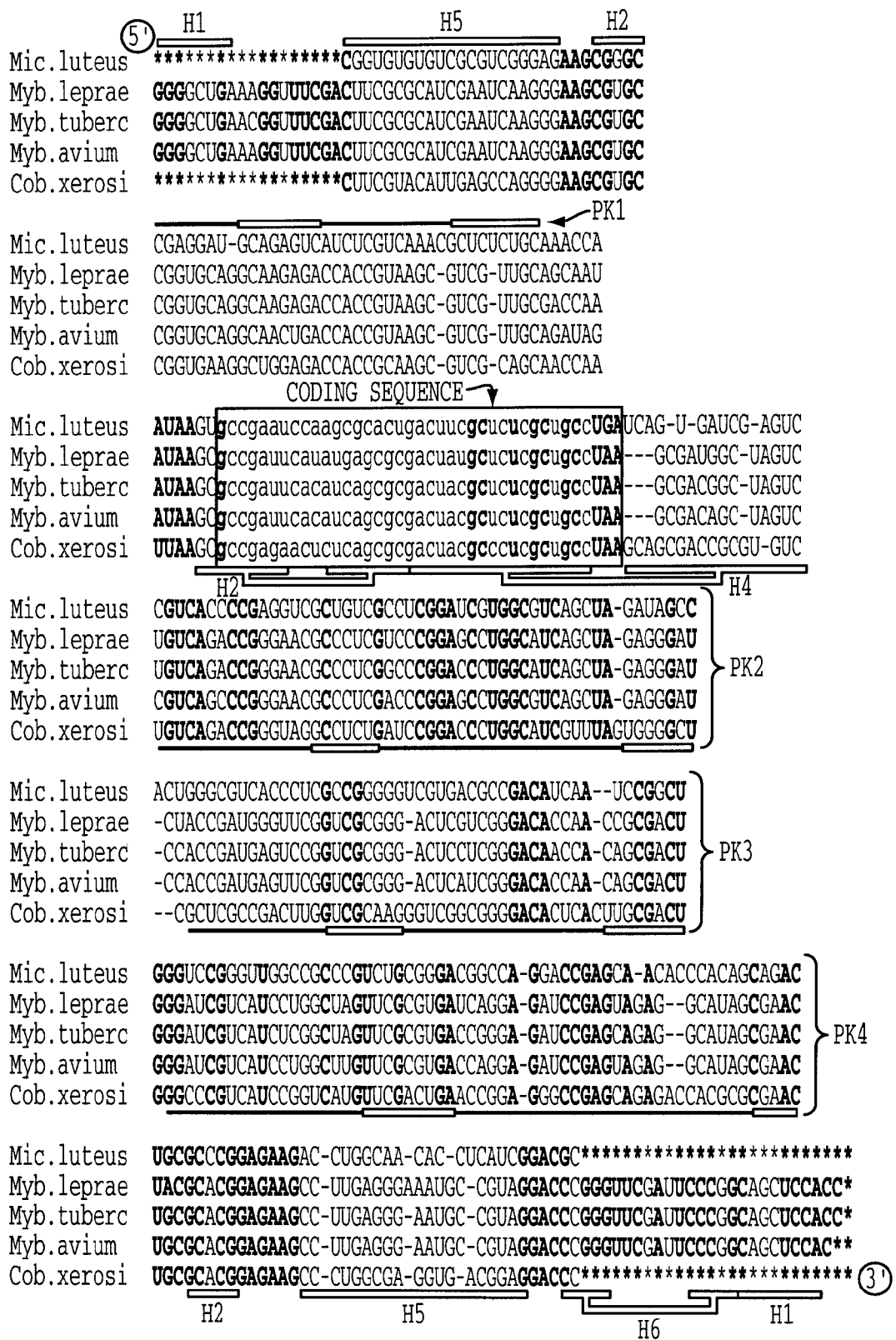
FIGS. 8A and 8B show the sequence alignment, structural domains and structural features for the tmRNA of several species of *Actinobacteries* (8A) and *Spirochaetes* (8B). The tmRNA sequences of the *Actinobacteries* are set forth in SEQ ID NOs:132-136, and the tmRNA sequences of the *Spirochaetes* are set forth in SEQ ID NOs:137-142.
Figure 8B:
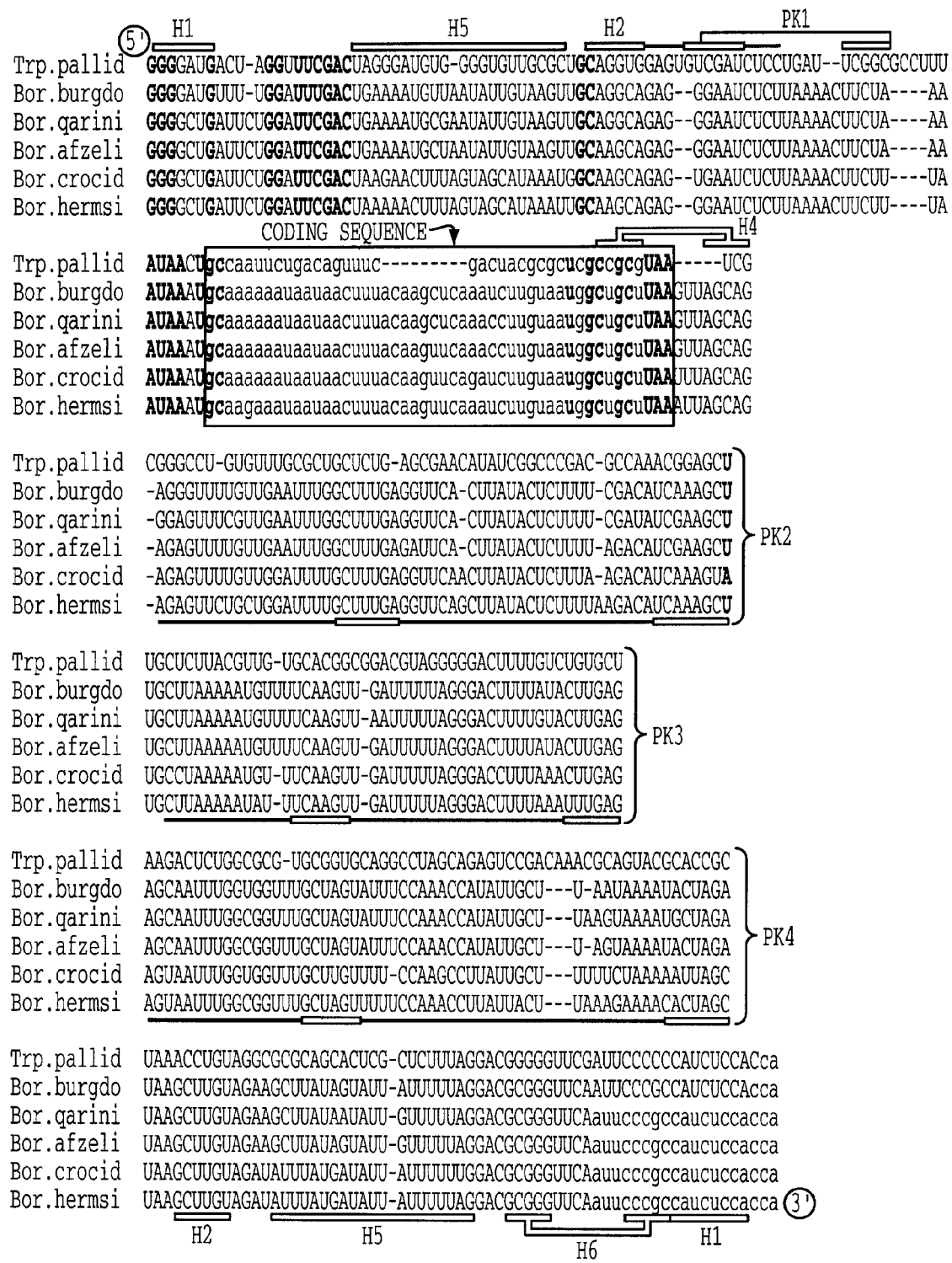
Figure 9A:
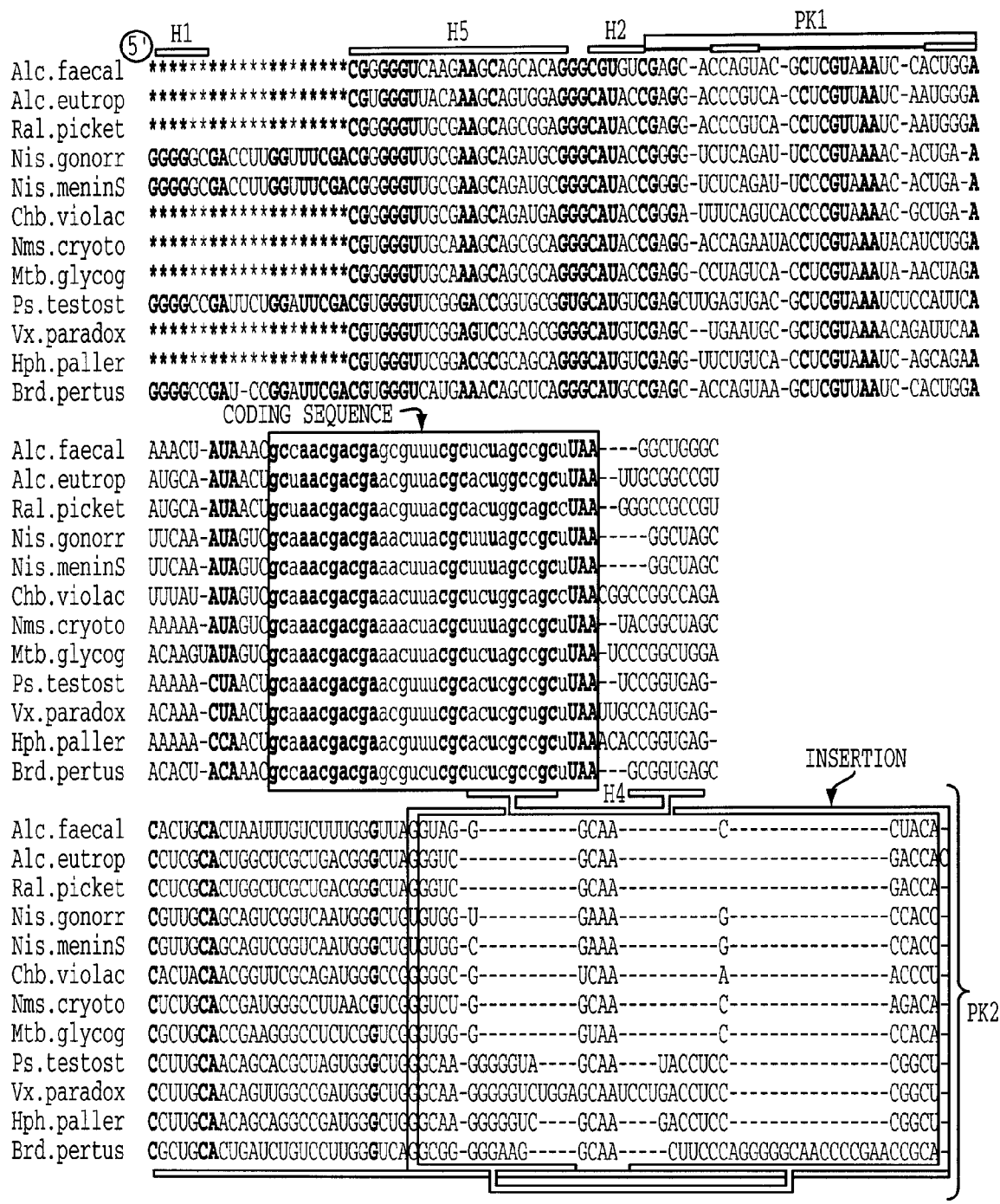
Figure 11A:
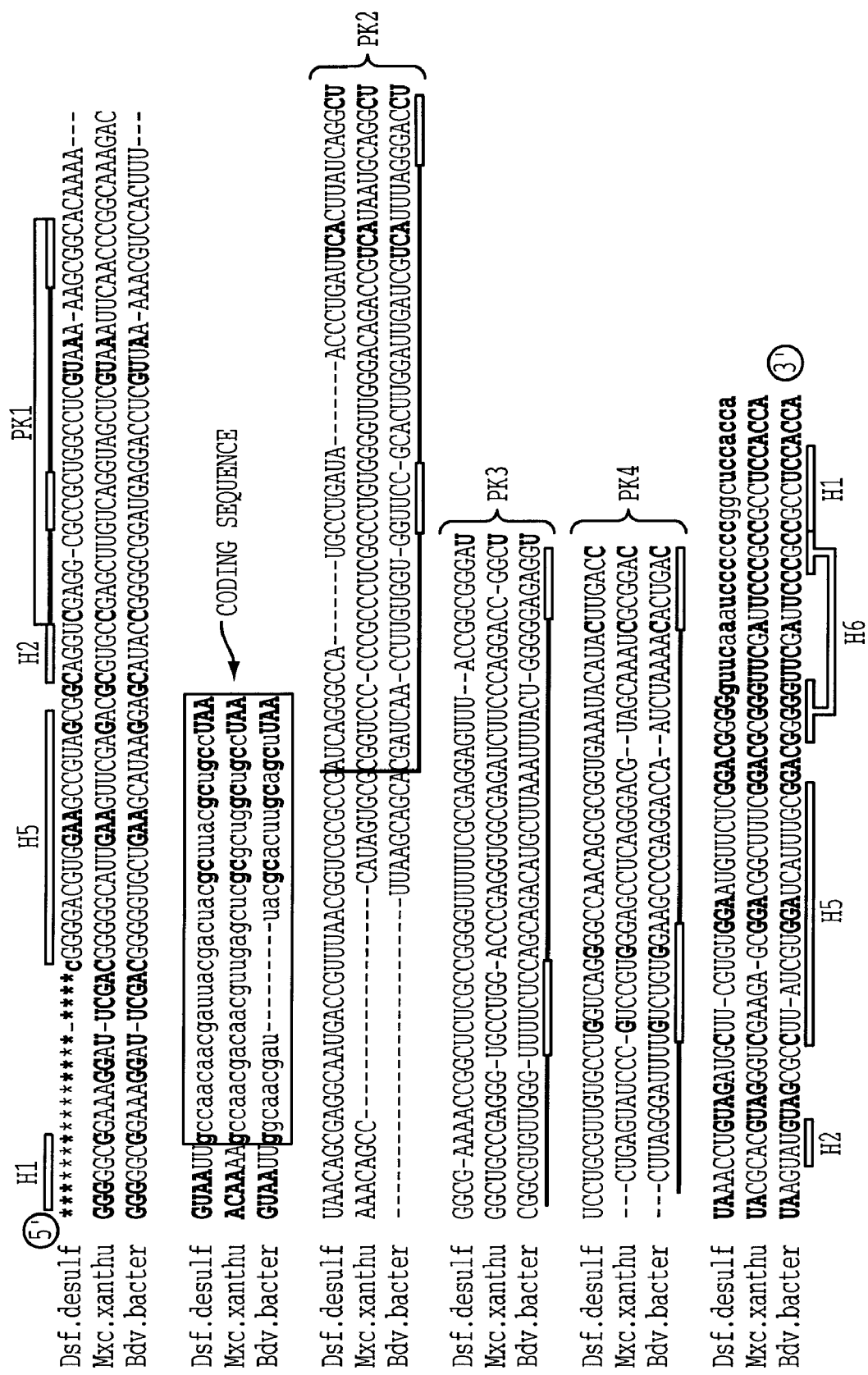
FIGS. 11A and 11B show the sequence alignment, structural domains and structural features for the tmRNA of several species of *Pourpres* delta (11A) and *Pourpres* epsilon (11B). The tmRNA sequences of the *Pourpres* delta are set forth in SEQ ID NOs:170-172, and the tmRNA sequences of the *Pourpres* epsilon are set forth in SEQ ID NOs:173-175.
Figure 11B:
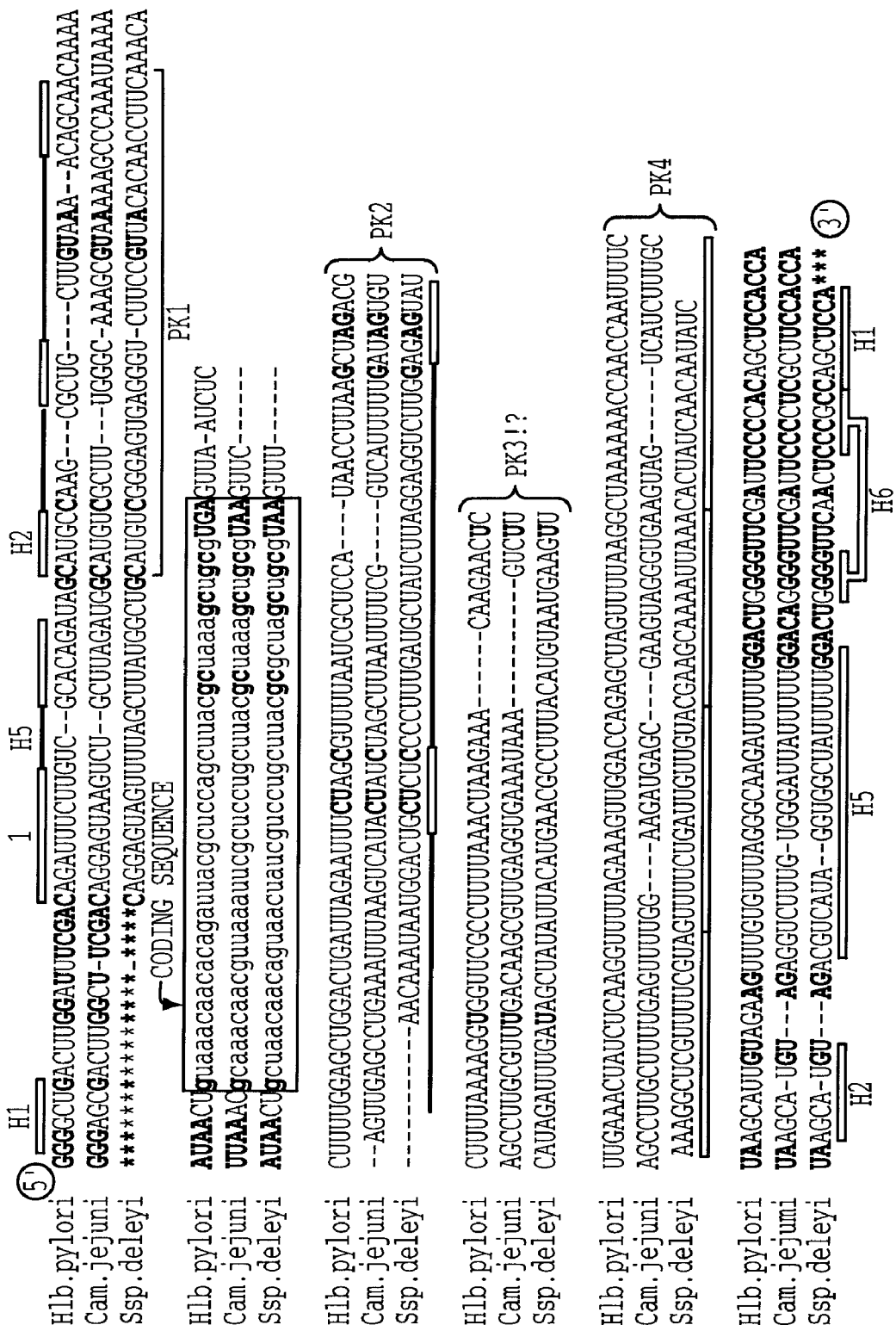

According to these procedures, tmRNA genes from many eubacteria including known human pathogens were amplified. The PCR was facilitated by sequence conservation at both 5' and 3' ends and was performed as described (Williams and Bartel, 1996), with modifications. This study was initiated to collect further sequences from eubacterial tmDNA genes, as well as to test experimentally whether tmDNA genes could be found in all bacterial phyla or subgroups. 51 new tmDNA sequences were determined (FIG. 2), including sequences from members of 8 additional phyla and 1 subgroup (shaded boxes in FIG. 2). The 58 new tmDNA sequences are set forth in Tables 1-58. This brings coverage to a total of 104 sequences in 19 bacterial phyla. Interestingly, tmDNA sequences could be amplified from all species tested apart from those in the alpha-Proteobacteria. Five genomic DNAs from alpha-Proteobacteria (*Agrobacterium tumefaciens, Bartonella henselae, Bartonella quintana, Rhodospirillum rubrum* and *Rickettsia prowazekii*) were extensively checked using various oligonucleotides, annealing temperatures and magnesium concentrations. No specific amplified tmDNA sequences were detected in this subgroup. Moreover, no putative tmDNA sequences could be identified (results herein and Williams, 1999) by Blast searches on the 1 fully sequenced (*Rickettsia prowazekii*) and 2 nearly completed (*Caulobacter crescentus* and *Rhodobacter capsulatus*) alpha-proteobacterial genomes (FIG. 2).

It cannot be ruled out that tmDNA sequences may have largely diverged in the alpha-proteobacterial sub-group compared to other bacterial phyla, and that both PCR methods and Blast searches are missing the relevant sequences. While tmRNA is dispensable in *E. coli* (Ando et al., 1996), it is striking that it has been found in all bacteria tested other than the alpha-Proteobacteria. The alpha-Proteobacteria have undergone reductive evolution. This has been more intensive in one of the two sub-classes than in the other (Gray and Spencer, 1996), but tmRNA sequences have not been found even in the sub-class with the larger genome. Based on sequence comparison, the alpha-Proteobacteria and mitochondria are evolutionary relatives (Yang et al., 1985; Andersson et al., 1998). The drastic downsizing in what has become mitochondrial genomes means that it is not reasonable to draw inferences on the relationship between alpha-Proteobacteria and mitochondria based on their mutual apparent absence of tmRNA. It is nevertheless, of interest, that at least some chloroplasts and cyanelle genomes have tmDNA sequences, and the cyanobacteria, with which they are evolutionary related, also have tmRNA.

TABLE 1 tmDNA Sequence for *Acidobacterium capsulatum*
(*Acidobacterium*)

(SEQ ID NO: 9)
GGGGGCGGAAAGGATTCGACGGGGTTGACTGCGGCAAAGAGGCATGCCGG

GGGGTGGGCACCCGTAATCGCTCGCAAAACAATACTTGCCAACAACAATC

TGGCACTCGCAGCTTAATTAAATAAGTTGCCGTCCTCTGAGGCTTCGCCT

GTGGGCCGAGGCAGGACGTCATACAGCAGGCTGGTTCCTTCGGCTGGGTC

TGGGCCGCGGGGATGAGATCCACGGACTAGCATTCTGCGTATCTTGTCGC

TTCTAAGCGCAGAGTGCGAAACCTAAAGGAATGCGACTGAGCATGGAGTC

TCTTTTCTGACACCAATTTCGGACGCGGGTTCGATTCCCGCCGCCTCCAC

CA

TABLE 2 tmDNA Sequence for *Coprothermobacter proteolyticus*
(60 degrees)

(SEQ ID NO: 10)
GGGGGCGGAAAGGATTCGACGGGGAGTCGGAGCCTTGAGCTGCAGGCAGG

GTTGGCTGCCACACCTTAAAAAGGGTAGCAAGGCAAAAATAAATGCCGAA

CCAGAATTTGCACTAGCTGCTTAATGTAAGCAGCCGCTCTCCAAACTGAG

GCTGCATAAGTTTGGAAGAGCGTCAACCCATGCAGCGGCTCTTAAGCAGT

GGCACCAGCTGTTTAAGGGTGAAAAGAGTGGTGCTGGGCAGTGCGGTTGG

GCTTCCTGGGCTGCACTGTCGAGACTTCACAGGAGGGCTAAGCCTGTAGA

CGCGAAAGGTGGCGGCTCGTCGGACGCGGGTTCGATTCCCGCCGCCTCCA

CCA

TABLE 3 tmDNA Sequence for *Bacteroides thetaiotaomicron*
(*bacteroides/flavobacterium*)

(SEQ ID NO: 11)
GGGGCTGATTCTGGATTCGACAGCGGGCAGAAATGGTAGGTAAGCATGCA

GTGGGTCGGTAATTTCCACTTAAATCTCAGTTATCAAAACTTTATCTGGC

GAAACTAATTACGCTCTTGCTGCTTAATCGAATCACAGTAGATTAGCTTA

ATCCAGGCACTAGGTGCCAGGACGAGACATCACTCGGAAGCTGTTGCTCC

GAAGCATTCCGGTTCAGTGGTGCAGTAACATCGGGGATAGTCAGAAGCGG

TABLE 3-continued tmDNA Sequence for *Bacteroides thetaiotaomicron* (bacteroides/flavobacterium)

CCTCGCGTTTTTGATGAAACTTTAGAGGATAAGGCAGGAATTGATGGCTT

TGGTTCTGCTCCTGCACGAAAATTTAGGCAAAGATAAGCATGTAGAAAGC

TTATGATTTCCTCGTTTGGACGAGGGTTCAACTCCCGCCAGCTCCACCA

TABLE 4 tmDNA Sequence for *Dictyoglomus thermophilum* (70 degrees)

(SEQ ID NO: 12)
GGGGCTGATTCTGGATTCGACAGGGAGTACAAGGATCAAAAGCTGCAAGC

CGAGGTGCCGTTACCTCGTAAAACAACGGCAAAAAAGAAGTGCCAACACA

AATTTAGCATTAGCTGCTTAATTTAGCAGCTACGCTCTTCTAACCCGGGC

TGGCAGGGTTAGAAGGGTGTCATAATGAGCCAGCTGCCCCTTCCGACTCC

CCTAAGGAAGGGAAAGATGTAGGGGATAGGTGCTTACAGAATCCTGCGGG

AGGGAGTCTGTAAGTGCCGAAAAGTTAAAACTCCCGCTAAGCTTGTAGAG

GCTTTTGATTCTTGCTCTCTGGACGCGGGTTCAACTCCCGCCAGCTCCAC

CA

TABLE 5 tmDNA Sequence for Environmental Sample from Rumenal Fluid (SEQ ID NO: 13)
ACGCCCTTGTCTCAGACGAGGGCACTCGTTAAAAAGTCTGAAAAGAATAA

CTGCAGAACCTGTAGCTATGGCTGCTTAATTTAAGGGCAACCCTTGGATC

CGCCTCCATCCCGAAGGGGTGGCATCCGAGTCGCAAATCGGGATAGGATG

GATCTTGGCAACGAGGAGTACATCCGAAATTTGTCGCTGCTGGCTGAAGC

ATCGCCGTTCCTCTTTGGGCGTGGCAAGGCAAGATTAAATTCAGAGGATA

AGCGTGTAGTAGCGAGTGAGTAGGTGTTTTTGGACGCGGGTTCAAGTCCC

GCCATCTCCACCA

TABLE 6 tmDNA Sequence for Environmental Sample from Sludge (SEQ ID NO: 14)
GGGGATGTCATGGTTTTGACAGGGAACCAGGAGGTGTGAGATGCATGCCG

GAGACGCTGTCCGCTCCGTTATCAAGCAGCAAACAAAACTAATTGCAAAC

AACAATTACTCCTTAGCAGCGTAAGCAGCTAACGTTCAACCTCTCCGGAC

CGCCGGGAGGGGATTTGGGCGTCGAAACAGCGCGGACGCTCCGGATAGGA

CGCCCATAATATCCGGCTAAGACCATGGGTCTGGCTCTCGCGGGTCTGAT

TGTCTTCCACCGCGCGGGCCGCGATCAAAGACAACTAAGCATGTAGGTTC

TTGCATGGCCTGTTCTTTGGACGCGGGTTCGATTCCCGCCATCTCCACCA

TABLE 7 tmDNA Sequence for *Fibrobacter succinogenes* (Fibrobacter)

(SEQ ID NO: 15)
GGGGCTGATTCTGGATTCGACAGGGGTTACCGAAGTGTTAGTTGCAAGTCG

AGGTCTCAGACGAGGGCTACTCGTTAAAAAGTCTGAAAAAAAATAAGTGC

TGACGAAAACTACGCACTCGCTGCCTAATTAACGGCAACGCCGGGCCTCA

TTCCGCTCCCATCGGGGTGTACGTCCGGACGCAATATGGGATAGGGAAGT

GTCATGCCTGGGGGCATCTCCCGAGATTTTCTAGGCTGGTCAAACTCCGC

GCCGACCTTCTTGGGCGTGGATAAGACGAGATCTTAAATTCGAAGGGAAC

ACTTGTAGGAACGTACATGGACGTGATTTTGGACAGGGGTTCAACTCCCG

CCAGCTCCA

TABLE 8 tmDNA Sequence for *Fusobacterium mortiferum*

(SEQ ID NO: 16)
GGGGCTGATTCTGGATTCGACGGGGTTATGAGGTTATAGGTAGCATGCCA

GGATGACCGCTGTGAGAGGTCAACACATCGTTTAGATGGAAACAGAAATT

ACGCTTTAGCTGCTTAATTAGTCAGCTCACCTCTGGTTTCTCTCTTCTGT

AGGAGAATCCAACCGAGGTGTTACCAATATACAGATTACCTTTAGTGATT

TCTCTAAGCTCAAAGGGACATTTTAGAGAATAGCTTCAGTTAGCCCTGTC

TGCGGGAGTGATTGTTGCGAAATAAAATAGTAGACTAAGCATTGTAGAAG

CCTATGGCGCTGGTAGTTTCGGACACGGGTTCAACTCCCGCCAGCTCCAA

TABLE 9 tmDNA Sequence for *Corynebacterium xerosis* (gram +, high G-C content)

(SEQ ID NO: 17)
GGGGCTGATTCTGGATTCGACTTCGTACATTGAGCCAGGGGAAGCGTGCC

GGTGAAGGCTGGAGACCACCGCAAGCGTCGCAGCAACCAATTAAGCGCCG

AGAACTCTCAGCGCGACTACGCCCTCGCTGCCTAAGCAGCGACCGCGTGT

CTGTCAGACCGGGTAGGCCTCTGATCCGGACCCTGGCATCGTTTAGTGGG

GCTCGCTCGCCGACTTGGTCGCAAGGGTCGGCGGGGACACTCACTTGCGA

CTGGGCCCGTCATCCGGTCATGTTCGACTGAACCGGAGGGCCGAGCAGAG

ACCACGCGCGAACTGCGCACGGAGAAGCCCTGGCGAGGTGACGGAGGACC

CGGGTTCAACTCCCGCCAGCTCCACCA

TABLE 10 tmDNA Sequence for *Micrococcus luteus* (parfait)

(SEQ ID NO: 18)
GGGGCTATTCTGGATTCGACGGTGTGTGTCGCGTCGGGAGAAGCGGGCCG

AGGATGCAGAGTCATCTCGTCAAACGCTCTCTGCAAACCAATAAGTGCCG

AATCCAAGCGCACTGACTTCGCTCTCGCTGCCTGATCAGTGATCGAGTCC

TABLE 10-continued tmDNA Sequence for *Micrococcus luteus* (parfait)

GTCACCCCGAGGTCGCTGTCGCCTCGGATCGTGGCGTCAGCTAGATAGCC
ACTGGGCGTCACCCTCGCCGGGGGTCGTGACGCCGACATCAATCCGGCTG
GGTCCGGGTTGGCCGCCCGTCTGCGGGACGGCCAGGACCGAGCAACACCC
ACAGCAGACTGCGCCCGGAGAAGACCTGGCAACACCTCATCGGACGCGGG
TTCAACTCCCGCANTCCCACCA

TABLE 11 tmDNA Sequence for *Mycobacterium smegmatis*

(SEQ ID NO: 19)
TCATCTCGGCTTGTTCGCGTGACCGGGAGATCCGAGTAGAGACATAGCGA
ACTGCGCACGGAGAGGGGCTGATTCCTGGATTCGACTTCGAGCATCGAAT
CCAGGGAAGCGTGCCGGTGCAGGCAAGAGACCACCGTAAGCGTCGTTGCA
ACCAATTAAGCGCCGATTCCAATCAGCGCGACTACGCCCTCGCTGCCTAA
GCGACGGCTGGTCTGTCAGACCGGGAGTGCCCTCGGCCCGGATCCTGGCA
TCAGCTAGAGGGACCCACCCACGGGTTCGGTCGCGGGACCTGTGGGACA
TCAAACAGCGACTGGGATCGAGCCTCGAGGACATGCCGTAGGACCCGGT
TCAACTCCCGCCAGCTCCACCA

TABLE 12 tmDNA Sequence for *Bacillus badius*

(SEQ ID NO: 20)
GGGGGTGATTCTGGATTCGACAGGGATAGTTCGAGCTTGGGCTGCGAGCC
GGAGGGCCGTCTTCGTACCAACGCAAACGCCTAAATATAACTGGCAAAAA
AGATTTAGCTTTAGCTGCCTAATATAGGTTCAGCTGCTCCTCCCGCTATC
GTCCATGTAGTCGGGTAAGGGGTCCAAACTTAGTGGACTACGCCGGAGTT
CTCCGCCTGGGGACAAAGGAAGAGATCAATCAGGCTAGCTGCCCGGACGC
CCGTCGATAGGCAAAAGGAACAGTGAACCCCAAATATATCGACTACGCTC
GTAGACGTTCAAGTGGCGTTATCTTTGGACGTGGGTTCAACTCCCGCCAG
CTCCA

TABLE 13 tmDNA Sequence for *Bacillus brevis*

(SEQ ID NO: 21)
GGGGGCGGAAAGGATTCGACGGGGATGGTAGAGCATGAGAAGCGAGCCGG
GGGGTTGCGGACCTCGTCACCAACGCAAACGCCATTAACTGGCAACAAAC
AACTTTCTCTCGCTGCTTAATAACCAGTGAGGCTCTCCCACTGCATCGGC
CCGTGTGCCGTGGATAGGGCTCAACTTTAACGGGCTACGCCGGAGGCTTC
CGCCTGGAGCCAAAGGAAGAAGACCAATCAGGCTAGGTGCCAGGTCAGCG
CGTCACTCCGCGAATCTGTCACCGAAACTCTAAACGAGTGACTGCGCTCG
GAGATGCTCATGTATCGCTGTTTTCGGACGGGGGTTCGATTCCCGCCGCC
TCACCCA

TABLE 14 tmDNA Sequence for *Bacillus thermoleovorans*
(50-60 degres)

(SEQ ID NO: 22)
GGGGGCGGAAAGGATTCGACGGGGGTAGGTCGAGCTTAAGCGGCGAGCCG
AGGGGGACGTCCTCGTAAAAACGTCACCTAAAGATAACTGGCAAACAAAA
CTACGCTTTAGCTGCCTAATTGCTGCAGCTAGCTCCTCCCGCCATCGCCC
GCGTGGCGTTCGAGGGGCTCATATGGAGCGGGCTACGCCCAAATCCGCCG
CCTGAGGATGAGGGAAGAGACGAATCAGGCTAGCCGCCGGGAGGCCTGTC
GGTAGGCGGAACGGACGGCGAAGCGAAATATACCGACTACGCTCGTAGAT
GCTTAAGTGGCGATGCCTCTGGACGTGGGTTCGATTCCCGCCGCCTCCCC
ACCA

TABLE 15 tmDNA Sequence for *Clostridium innocuum*

(SEQ ID NO: 23)
GGGGGCGGAAAGGATTCGACGGGGATATGTCTGGTACAGACTGCAGTCGA
GTGGTTACGTAATAACCAATTAAATTTAAACGGAAAAACTAAATTAGCTA
ACCTCTTTGGTGGAAACCAGAGAATGGCTTTCGCTGCTTAATAACCGATA
TAGGTTCGCAGCCGCCTCTGCATGCTTCTTCCTTGACCATGTGGATGTGC
GCGTAAGACGCAAGGGATAAGGAATCTGGTTTGCCTGAGATCAGATTCAC
GAAAATTCTTCAGGCACATTCATCAGCGGATGTTCATGACCTGCTGATGT
CTTAATCTTCATGGACTAAACTGTAGAGGTCTGTACGTGGGGCTGTTTCT
GGACAGGAGTTCGATTCCCGCCGCCTCACCACCA

TABLE 16 tmDNA Sequence for *Clostridium lentocellum*

(SEQ ID NO: 24)
GGGGGCGGAAAGGATTCGACGGGGGTCACATCTACTGGGGCAGCCATCCG
TAGAACGCCGGAGTCTACGTTAAAAGCTGGCACTTAAAGTAAACGCTGAA
GATAATTTAGCAATCGCTGCCTAATTAAGGCGCAGTCCTCCTAGGTCTTC
CGCAGCCTAGATCAGGGCTTCGACTCGCGGATCCTTCACCTGGCAAAGCT
TTGAGCCAACGTGAACACTATGAAGCTACTAAAATCTAGAGCCTGTCTTT
GGGCGCTAGATGGAGGGAATGTCAAAACAAAGAATATGATGGTAGAGACC
ACGCTATATGGGCTTTCGGACAGGGGTTCGATTCCCGCCGCCTTCACCA

TABLE 17 tmDNA Sequence for *Clostridium perfringens*

(SEQ ID NO: 25)
GGGGCTGATTCTGGATTCGACGGGGGTAAGATGGGTTTGATAAGCGAGTC
GAGGGAAGCATGGTGCCTCGATAATAAAGTATGCATTAAAGATAAACGCA
GAAGATAATTTTGCATTAGCAGCTTAATTTAGCGCTGCTCATCCTTCCTC
AATTGCCCACGGTTGAGAGTAAGGGTGTCATTTAAAAGTGGGGAACCGAG

TABLE 17-continued

| tmDNA Sequence for *Clostridium perfringens* |
|---|
| CCTAGCAAAGCTTTGAGCTAGGAACGGAATTTATGAAGCTTACCAAAGAG |
| GAAGTTTGTCTGTGGACGTTCTCTGAGGGAATTTTAAAACACAAGACTAC |
| ACTCGTAGAAAGTCTTACTGGTCTGCTTTCGGACACGGGTTCAACTCCCG |
| CCACTCCA |

TABLE 18

| tmDNA Sequence for *Clostridium stercorarium* |
|---|
| (SEQ ID NO: 26) |
| GGGGGCGGAAAGGATTCGACGGGGTTATTGAAGCAAGAGTAGCGGGTAGA |
| GGATTCTCGTTGGCCTCTTTAAAAAACGAGAGCTAAAAATAAACGCAAAC |
| AACGATAACTACGCTTTAGCTGCTGCGTAAGTAACACGCAGCCCGTCGGC |
| CCCGGGGTTCCTGCGCCTCGGGATACCGGCGTCATCAAGGCAGGGAACCA |
| GCCGGATCAGGCTTCAGGTCCGGTGGGATTTAATGAAGCTACCGACTTAT |
| AAAGCCTGTCTCTGGGCGTTATAAGAAGGGAATGTCAAAACAGAGACTGC |
| ACCCGGAGAAGCTCTTGTGGATATGGTTCCGGACACGAGTTCGATTCCCG |
| CCGCCTCCACCA |

TABLE 19

| tmDNA Sequence for *Enterococcus faecium* (sp.) |
|---|
| (SEQ ID NO: 27) |
| GGGGCTGATTATGGATTCGACAGGATNGTTGAGCTTGAATTGCGTTTCGT |
| AGGTTACGGCTACGTTAAAACGTTACAGTTAAATATAACTGCTAAAAACG |
| AAAACAATTCTTTCGCTTTAGCTGCCTAAAAACCAGCTAGCGAAGATCCT |
| CCCGGCATCGCCCATGTGCTCGGGTCAGGGTCCTAATCGAAGTGGGATAC |
| GCTAAATTTTTCCGTCTGTAAAATTTAGAGGAGCTTACCAGACTAGCAAT |
| ACAAGAATGCCTGTCACTCGGCACGCTGTAAAGCGAACCTTTAAATGAGT |
| GTCTATGAACGTAGAGATTTAAGTGGGAATATGTTTTGGACGCGGGTTCA |
| ACTCCCGCCAGCTCCACCA |

TABLE 20

| tmDNA Sequence for *Heliobacillus mobilis* (photosyn/gram +) |
|---|
| (SEQ ID NO: 28) |
| GGGGCTGATTCTGGATTCGACGGGGAACGTGTTTGCTTGGGATGCGAGCC |
| GGGTTGCCGCCAGGACCGTAAAAAGGGCGGAAGGCTTTAATTGCCGAAGA |
| TAACTACGCTTTAGCTGCTTAATTGCAGTCTAACCTCTTCTCCTCTGTGC |
| TCTCGGTGAGGATGTAAGGGGTCATTTAAGAGAGCTGGCTTCGACCAATT |
| CTCGGAGGTCCAAGCGAGATTTATCGAGATAGCCTGACCAACGCTCTGTC |
| TGCCGTGCGGAAGGAAGGCGAAATCTAAAACGACAGACTACGCTCGTAGT |
| GTCCTTTGTGGGCATTTCTTCGGACGCGGGTTCAACTCCCGCCAGCTCCA |
| CCA |

TABLE 21

| tmDNA Sequence for *Heliospirillum gestii* |
|---|
| (SEQ ID NO: 29) |
| GGGGCTGATTCTGGATTCGACGGGGAACGTGTTTGCTTAGGACGCGAGCC |
| GGGTTGCCGCCAGGACCGTAAAAAGGGCGGAAGGCTTTAATTGCCGAAGA |
| TAACTACGCTTTAGCTGCTTAATTGCAGTCTAACCTCTTCTCCTCTGTGC |
| TCTCGGTGAGGATGTAAGGGGTCATTTAAGAGAGCTGGCTCGAACCAATT |
| CTCGGAGGTTCGGGTAAGACTTATCGAGATAGCCTGACCAACGCTCTGTC |
| TGCCGTGCGGAAGGATGGCGAAATCTAAAACGACAGAATACGCTCGTAGT |
| GTCCTTTGTGGGCATTTCTTCGGACGCGGGTTCAACTCCCGCCAGCTCCA |
| CCA |

TABLE 22

| tmDNA Sequence for *Lactobacillus acidophilus* |
|---|
| (SEQ ID NO: 30) |
| GGGGCTGATTCTGGATTCGACAGGCGTAGACCCGCATTGACTGCGGTTCG |
| TAGGTTACGTCTACGTAAAAACGTTACAGTTAAATATAACTGCAAATAAC |
| AAAAATTCTTACGCATTAGCTGCTTAATTTAGCGCATGCGTTGCTCTTTG |
| TCGGTTTACTCGTGGCTGACACTGAGTATCAACTTAGCGAGTTACGTTTA |
| ACTACCTCACCTGAATAGTTGAAAAGAGTCTTAGCAGGTTAGCTAGTCCA |
| TACTAGCCCTGTTATATGGCGTTTTGGACTAGTGAAGTTCAAGTAATATA |
| ACTATGATCGTAGAGGTCAGTGACGAGATGCGTTTGGACAGCGGGTTCAA |
| CTCCCGCCAGCTCCACCA |

TABLE 23

| tmDNA Sequence for *Staphylococcus epidermidis* |
|---|
| (SEQ ID NO: 31) |
| GGGGCTGATTCTGCATTCGACAGGGGTCCCCGAGCTTATTAAGCGTGTGG |
| AGGGTTGGCTCCGTCATCAACACATTTCGGTTAAATATAACTGACAAATC |
| AAACAATAATTTCGCAGTAGCTGCGTAATAGCCACTGCATCGCCTAACAG |
| CATCTCCTACGTGCTGTTAACGCGATTCAACCCTAGTAGGATATGCTAAA |
| CACTGCCGCTTGAAGTCTGTTTAGATGAAATATAATCAAGCTAGTATCAT |
| GTTGGTTGTTTATTGCTTAGCATGATGCGAAAATTATCAATAAACTACAC |
| ACGTAGAAAGATTTGTATCAGGACCTCTGGACGCGGGTTCAACTCCCGCC |
| AGCTCCACCA |

TABLE 24

| tmDNA Sequence for *Streptococcus faecium* |
|---|
| (SEQ ID NO: 32) |
| GGGGCTGATTCTGGATTCGACAGGCACAGTTTGAGCTTGAATTGCGTTTC |
| GTAGGTTACGTCTACGTTAAAACGTTACAGTTAAATATAACTGCTAAAAA |
| CGAAAACAACTCTTACGCTTTAGCTGCCTAAAAACAGTTAGCGTAGATCC |

TABLE 24-continued tmDNA Sequence for *Streptococcus faecium*

TCTCGGCATCGCCCATGTGCTCGAGTAAGGGTCTCAAATTTAGTGGGATA

CGTGACAACTTTCCGTCTGTAAGTTGTTAAAGAGATCATCAGACTAGCGA

TACAGAATGCCTGTCACTCGGCAAGCTGTAAAGCGAAACCACAAATGAGT

TGACTATGAACGTAGATTTTTAAGTGGCGATGTGTTTGGACGCGGGTTCA

ACTCCCGCCGTTCCACCA

TABLE 25 tmDNA Sequence for *Thermoanaerobacterium saccharolyticum* (Bacillus/clostridium)

(SEQ ID NO: 33)
GGGGTAGTAGAGGTAAAAGTAGCGAGCCGAGGTTCCATCTGCTCGTAAAA

CGGTGGACTTAAATATAAACGCAAACGATAATTTAGCTTACGCTGCTTAA

TTACAAGCAGCCGTTCAACCTTTGATTCCCACATCAAAGGATTGGGCGTC

GATTTAGTGGGGAACTGATTTATCAAAGCTTTGAGATAAATCGGATTTTA

TGAAGCTACCAAAGCAGTTATCCTGTCACTGGGGAACTGCAGAGGGAAT

GTCAAAACAGTGACTGCGCTCGGAGAAGCTTTTACTGTGACACCTTCGGA

CCGGGGTTCAACTCCCGCCAGCTCCACCA

TABLE 26 tmDNA Sequence for *Mycoplasma fermentans*

(SEQ ID NO: 34)
GGGGCTGATTCTGGATTCGACATGCATTGGGTGATACTAATATCAGTAGT

TTGGCAGACTATAATGCATCTAGGCTTTATAATCGCAGAAGATAAAAAG

CAGAAGAAGTTAATATTTCTTCACTTATGATTGCACAAAAAATGCAATCA

CAATCAAACCTTGCTTTCGCTTAGTTAAAAGTGACAAGTGGTTTTAAAGT

TGACATTTTCCTATATATTTTAAAATCGGCTTTTAAGGAGAACAGGAGTC

TGAAAGGGTTCCAAAAATCTATATTGTTTGCATTTCGGTAGTATAGATTA

ATTAGAAATGATAAACTGTAAAAAGTATTGGTATTGACTTGGTGTGTGGA

CTCGGGTTCAACTCCCGCCAGCTCCACCA

TABLE 27 tmDNA Sequence for *Mycoplasma hyorhinis*

(SEQ ID NO: 35)
GGGGCTGATTCTGGATTCGACATACATAAAAGGATATAAATTGCAGTGGT

CTTGTAAACCATAAGACAATTTCTTTACTAAGCGGAAAAGAAAACAAAAA

AGAAGATTATTCATTATTAATGAATGCTTCAACTCAATCAAATCTAGCTT

TTGCATTTTAAAAAACTAGTAGACCAATTTGCTTCTCACGAATTGTAATC

TTTATATTAGAGAATAGTTAAAAATCTGATCACTTTTTAATGAATTTATA

GATCACAGGCTTTTTTAATCTTTTTGTTATTTTAGATAAAGAGTCTTCTT

TABLE 27-continued tmDNA Sequence for *Mycoplasma hyorhinis*

AAAAATAACTAAACTGTAGGAATTTATATTTAATTATGCGTGGACCCGGG

TTCAACTCCCGCCAGCTCCACCA

TABLE 28 tmDNA Sequence for *Mycoplasma pirum*

(SEQ ID NO: 36)
GGGGAGTCATGGTTTTGACATGAATGATGGACCCATAGAGGCAGTGGGGT

ATGCCCCTTATAGCTCAAGGTTTAAATTAACCGACAAAACTGACGAAAAC

GTTGCCGTTGATACAAATTTATTAATCAACCAACAAGCTCAATTTAACTA

CGCATTTGCATAGTATAAAAAAATAAATTGTGCTACTCATTGTAATTAGG

TTACTAAATTACTTTGTTTTATATAGTCCTGTAACTAGTTCTAGTGATGT

CTATAAACTAGAATGAGATTTATAGACTTATTTGTTGGCGGTTGTGCCAT

AGCCTAAATCAACAAAGACAATTTATTTATGGTACTAAACTGTAGATTCT

ATGATGAAATTATTTGTGGAAACGGGTTCGATTCCCGCCATCTCCACCA

TABLE 29 tmDNA Sequence for *Mycoplasma salivarium*

(SEQ ID NO: 37)
GGGGCTGATTCTGGATTCGACAGGCATTCGATTCATTATGTTGCAGTGGT

TTGCAAACCATAAGGCACTAGGCTTTTTTAAACGCAAAAGACCAAAAAAC

AGAAGATCAAGCAGTTGATCTAGCATTTATGAATAATTCACAAATGCAAT

CAAATCTAGTTTTCGCTTAGTAAAATTAGTCAATTTATTATGGTGCTCAA

CATAATAAATGGTAGTATGAGCTTAATATCATATGATTTTAGTTAATATG

ATAGGATTTGTAACTAAACTATGTTATAGAAATTTGTAAATTATATATAT

GACATAGGAAATTTAATTTACTAAACTGTAGATGCATAATGTTGAAGATG

TGTGGACCGGGGTTCAACTCCCGCCAGCTCCACCA

TABLE 30 tmDNA Sequence for *Herpetosiphon aurantiacus*

(SEQ ID NO: 38)
GGGGGCGGAAAGGATTCGACGGGGAGGGCCAATCGTAAGTGGCAAGCCGA

GACGCTGAGCCTCGTTAAATCGGCAACGCCATTAACTGGCAAAAACACTT

TCCGCGCTCCTGTAGCGCTTGCTGCCTAATTAAGGCAACACGTCTCTACT

AGCCTCAGCCCGATGGGCTTGTAGCGGCGACACTTAGTCGGGTCGCTCCC

CTAGTTATGTCTGTGGGCTAGGGGCTAAGATTAACAGGCTGGTCGTGGCC

CGCTTTGTCTATCGGGTGGTGCACCGATAAGATTTAATCAATAGACTACG

CTTGTAGATGCTTGCGGTTTAACTTTTTGGACGCGGGTCGATTCCCGCC

GCCTCACCACCA

TABLE 31 tmDNA Sequence for *Thermomicrobium roseum*
(352 nts, temp. 70 degrees, green non sulfur)

(SEQ ID NO: 39)
GGGGCTGATTCTGGATTCGACAGGGCCGTAGGTGCGAGGATTGCAGGTCG

AGGTCGCCCACGAACTCGTAAAAAGGGGCAGCCAAGTAACTGGCGAGCGC

GAACTCGCTCTGGCTGCGTAATTCACGCAGCCACGTCTGCCCGGACCCTT

CCCTGGTGGGTTCGGAGCGGGCGCCGCAAGACCGGGGTGCCCCTGGCCCA

AGCGCCGGTGCGGGCCAGGTCAAGCGTGATCCGGCTCGGCTGACCGGGAT

CCTGTCGGTGGGAGCCTGGCAGCGACAGTAGAACACCGACTAAGCCTGTA

GCATATCCTCGGCTGAACGCTCTGGACGCGGGTTCAACTCCCGCCAGCTC

CACCA

TABLE 32 tmDNA Sequence for *Chlorobium limicola*

(SEQ ID NO: 40)
GGGGCTGATTCTGGATTCGACAGGATACGTGTGAGATGTCGTTGCACTCC

GAGTTTCAGCATGGACGGACTCGTTAAACAAGTCTATGTACCATTAGATG

CAGACGATTATTCGTATGCAATGGCTGCCTGATTAGCACAAGTTAACTCA

GACGCCATCGTCCTGCGGTGAATGCGCTTACTCTGAAGCCGCCGGATGGC

ATAACCCGCGCTTGAGCCTACGGGTTCGCGCAAGTAAGCTCCGTACATTC

ATGCCCGAGGGGCTGTGCGGGTAATTTCTCGGGATAAGGGGACGAACGCT

GCTGGCGGTGTAATCGGCCCACGAAAACCCAATCACCAGAGATGAGTGTG

GTGACTGCATCGAGCAGTGTTTTGGACGCGGGTTCAACTCCCGCCAGCTC

CACCA

TABLE 33 tmDNA Sequence for *Pirellula staleyi*
(planctomyces)

(SEQ ID NO: 41)
GGGGCTGATTCTGGATTCGACCGGATAGCCTGAAGCGAATACGGCGTGCC

GTGGTTGATCAGATGGCCACGTAAAAAGCTGATCACAAACTTAACTGCCG

AGAGCAATCTCGCACTTGCTGCCTAACTAAACGGTAGCTTCCGACTGAGG

GCTTTAGCCGGAGAGGCCCAAAAGTTGGTCACCAAATCCGGACCGCTCG

TGCCATGATCGAAACGCACGAGGTCAAAAAAGTTTCGATCTAGTGCAGGG

TGTAGCCAGCAGCTAGGCGACAAACTGTGCAAAAATCAAATTTTCTGCTA

CGCACGTAGATGTGTTCGTGAAAATGTCTCGGGACGGGGGTTCAACTCCC

GCCACTCCACCA

TABLE 34 tmDNA Sequence for *Planctomyces limnophilus*

(SEQ ID NO: 42)
GGGGCTGATTCTGGATTCGACAACCTCTCAAGGAGCGTGGCCACTATG

GGACTCGATTATGTTGAATTCGTCATGGATCTTGAAGAGACCTTCGACAT

TABLE 34-continued tmDNA Sequence for *Planctomyces limnophilus*

CAAACTGGATGACAAACATTTTTCAGCAGTCAAAACACCACGCGATTTGG

CAATCATTATTCGGGATCAATTAGCTGCTGAAGGCAGAATCTGGGATGAA

TCGAATGCTTTTCGCAAAATCTCGAATTTGAATTGGACGATGTTGCCCGA

GTTCCGGATGTGGACTCAAATCAAAAGCTCTCTACCAGTTTCTTTTCACC

GACTGCGTCCCAGCACCCGTCTCGTTCAACTCCCGCCANTCCACCA

TABLE 35 tmDNA Sequence for *Planctomyces maris*

(SEQ ID NO: 43)
GGGGCTGATTCTGGATTCGACTGGTTCACCGTATGTTAAGGTGGCGGTGC

CGTGGTTGATCAGTTGGCCACGTAAAAAGCTGATCACAATCTAATTGCAA

ACAAGCAATTTTCAATGGCTGCTTAATAAAAGCAACCCCGGCTTAGGAAT

CTCTGTCTGAGGAGTCCGACAGCTGGTCACAAAATCAGACTGGTATCAGA

TCAATGTCCGCTCCGTCTGATACGAGATTCGTGGTGGACTGGTTTCCAAC

AGGCTCTGTTTATCGTGCCCGAAGAAACGAGACTCAAACGATAAAATATG

CACCGTAGAGGCTTTAGCTGAGGGTTCACAGGACGCGGGTTCAACTCCCG

CCAGCTCCACCA

TABLE 36 tmDNA Sequence for *Alcaligenes eutrophus*

(SEQ ID NO: 44)
GGGGTTGATTCTGGATTCGACGTGGGTTACAAAGCAGTGGAGGGCATACC

GAGGACCCGTCACCTCGTTAATCAATGGGAATGCAATAACTGCTAACGAC

GAACGTTACGCACTGGCCGCTTAATTGCGGCCGTCCTCGCACTGGCTCGC

TGACGGGCTAGGGTCGCAAGACCACGCGAGGTCATTTACGTCAGATAAGC

TCCGGAAGGGTCACGAAGCCGGGGACGAAAACCTAGTGACTCGCCGTCGT

AGAGCGTGTTCGTCCGCGATGCGCCGGTTAAATCAAATGACAGAACTAAG

TATGTAGAACTCTCTGTGGAGGGCTTACGGACGCGGGTTCAACTCCCGCC

AGCTCCACCA

TABLE 37 tmDNA Sequence for *Alcaligenes faecalis* (beta
proteobacteria)

(SEQ ID NO: 45)
GGGGGCGGAAAGGATTCGACGGGGGTCAAGAAGCAGCACAGGGCGTGTCG

AGCACCAGTACGCTCGTAAATCCACTGGAAAACTATAAACGCCAACGACG

AGCGTTTCGCTCTAGCCGCTTAAGGCTGGGCCACTGCACTAATTTGTCTT

TGGGTTAGGTAGGGCAACCTACAGCAGTGTTATTTACAAAGAATCGAATC

GGTCTGCGCCACGAAGTCCGGTTCTAAAACTTAGTGGATCGCCAAGGAAA

GGCCTGTCAATTGGCATAGTCCAAGGTTAAAACTTAAAATTAATTGACTA

TABLE 37-continued tmDNA Sequence for *Alcaligenes faecalis* (beta proteobacteria)

CACATGTAGAACTGTCTGTGGACGGCTTGCGGACGGGGGTTCGATTCCCG

CCGCCTCCACCA

TABLE 38 tmDNA Sequence for *Chromobacterium violaceum* (beta-purple)

(SEQ ID NO: 46)
GGGGCTGATTCTGGATTCGACGGGGGTTGCGAAGCAGATGAGGGCATACC

GGGATTTCAGTCACCCCGTAAAACGCTGAATTTATATAGTCGCAAACGAC

GAAACTTACGCTCTGGCAGCCTAACGGCCGGCCAGACACTACAACGGTTC

GCAGATGGGCCGGGGCGTCAAAACCCTGTAGTGTCACTCTACATCTGCT

AGTGCTGTTCCGGGTTACTTGGTTCAGTGCGAAATAATAGGTAACTCGCC

AAAGTCCAGCCTGTCCGTCGGCGTGGCAGAGGTTAAATCCAAATGACACG

ACTAAGTATGTAGAACTCACTGTAGAGGACTTTCGGACGCGGGTTCAACT

CCCGCCAGCTCCACCA

TABLE 39 tmDNA Sequence for *Hydrogenophaga palleroni* (beta-purple)

(SEQ ID NO: 47)
GGGGCTGATTCTGGATTCGACGTGGGTTCGGACGCGCAGCAGGGCATGTC

GAGGTTCTGTCACCTCGTAAATCAGCAGAAAAAACCAACTGCAAACGAC

GAACGTTTCGCACTCGCCGCTTAAACACCGGTGAGCCTTGCAACAGCAGG

CCGATGGGCTGGGCAAGGGGTCGCAAGACCTCCCGGCTGCAAGGTAATT

TACATCGGCTGGTTCTGCGTCGGGCACCTTGGCGCAGGATGAGATTCAAG

GATGCTGGCTTCCCGTTTAGCGTGCCACTGCGCGACTCGGGCGGCGAGAC

CCAAATCAGACGGCTACACATGTAGAACTGCTCGAAAAAGGCTTGCGGAC

GGGGGTTCAACTCCCGCCAGCTCCACCA

TABLE 40 tmDNA Sequence for *Methylobacillus glycogenes* (beta-purple)

(SEQ ID NO: 48)
GGGGGCGGAAAGGATTCGACGGGGGTTGCAAAGCAGCGCAGGGCATACCG

AGGCCTAGTCACCTCGTAAATAAACTAGAACAAGTATAGTCGCAAACGAC

GAAACTTACGCTCTAGCCGCTTAATCCCGGCTGGACGCTGCACCGAAGGG

CCTCTCGGTCGGGTGGGGTAACCCACAGCAGCGTCATTAAGAGAGGATCG

TGCGATATTGGGTTACTTAATATCGTATTAAATCCAAGGTAACTCGCCTG

CTGTTTGCTTGCTCGTTGGTGAGCATCAGGTTAAATCAAACAACACAGCT

AAGTATGTAGAACTGTCTGTGGAGGGCTTGCGGACGGGGGTTCGATTCCC

GCCGCCTCACCACCA

TABLE 41 tmDNA Sequence for *Nitrosomonas cryotolerans* (beta-purple)

(SEQ ID NO: 49)
GGGGCTGATTCTGGATTCGACGTGGGTTGCAAAGCAGCGCAGGGCATACC

GAGGACCAGAATACCTCGTAAATACATCTGGAAAAAAATAGTCGCAAACG

ACGAAAACTACGCTTTAGCCGCTTAATACGGCTAGCCTCTGCACCGATGG

GCCTTAACGTCGGGTCTGGCAACAGACAGCAGAGTCATTAGCAAGGATCG

CGTTCTGTAGGGTCACTTTACAGAACGTTAAACAATAGGTGACTCGCCTG

CCATCAGCCCGCCAGCTGGCGGTTGTCAGGTTAAATTAAAGAGCATGGCT

AAGTATGTAGAACTGTCTGTAGAGGACTTGCGGACGCGGGTTCAACTCCC

GCCAGTCCACCA

TABLE 42 tmDNA Sequence for *Pseudomonas testosteroni*

(SEQ ID NO: 50)
GGGGCTGATTCTGGATTCGACGTGGGTTCGGGACCGGTGCGGTGCATGTC

GAGCTTGAGTGACGCTCGTAAATCTCCATTCAAAAAACTAACTGCAAACG

ACGAACGTTTCGCACTCGCCGCTTAATCCGGTGAGCCTTGCAACAGCACG

CTAGTGGGCTGGGCAAGGGGGTAGCAATACCTCCCGGCTGCAAGGGAATT

TTCATTAGCTGGCTGGATACCGGGCTTCTTGGTATTTGGCGAGATTTTAG

GAAGCTGGCTACCCAAGCAGCGTGTGCCTGCGGGGTTTGGGTGGCGAGAT

TTAAAACAGAGCACTAAACATGTAGATCTGTCCGGCGAAGGCTTACGGAC

GCGGGTTCAACTCCCGCCAGCTCCACCA

TABLE 43 tmDNA Sequence for *Ralstonia pickettii* (Burkholderia)

(SEQ ID NO: 51)
GGGGGCGGAAAGGATTCGACGGGGGTTGCGAAGCAGCGGAGGGCATACCG

AGGACCCGTCACCTCGTTAATCAATGGGAATGCAATAACTGCTAACGACG

AACGTTACGCACTGGCAGCCTAAGGGCCGCCGTCCTCGCACTGGCTCGCT

GACGGGCTAGGGTCGCAAGACCAGCGAGGTCATTTACGTCAGATAAGCTT

TAGGTGAGTCACGGGCCTAGAGACGAAAACTTAGTGAATCGCCGTCGTAG

AGCGTGTTCGTCCGCGATGCGGCGGTTAAATCAAATGACAGAACTAAGTA

TGTAGAACTCTCTGTGGAGGGCTTGCGGACGCGGGTTCGATTCCCGCCGC

CTCACCACCA

TABLE 44 tmDNA Sequence for *Variovax paradoxus* (*pseudomonas* sp.)

(SEQ ID NO: 52)
GGGGCTGATTCTGGATTCGACGTGGGTTCGGAGTCGCAGCGGGGCATGTC
GAGCTGAATGCGCTCGTAAAACAGATTCAAACAAACTAACTGCAAACGAC
GAACGTTTCGCACTCGCTGCTTAATTGCCAGTGAGCCTTGCAACAGTTGG
CCGATGGGCTGGGCAAGGGGGTCTGGAGCAATCCTGACCTCCCGGCTGCA
AGGATAACTACATGGGCTGGCTCCGATCCGGGTACCTTGGGTCGGGGCGA
GAAAATAGGGTACTGGCGTCCGGTTTAGCGTGTGACTGCGCGACTCCGGA
AGCGAGACTCAAAACAGATCACTAAACATGTAGAACTGCGCGATGAAGGC
TTGCGGACGGGGGTTCAACTCCCGCCAGCTCCACCA

TABLE 45 tmDNA Sequence for *Bdellovibrio bacteriovorus* (delta proteobacterie)

(SEQ ID NO:53)
GGGGGCGGAAAGGATTCGACGGGGTGCTGAAGCATAAGGAGCATACCGG
GGCGGATGAGGACCTCGTTAAAAACGTCCACTTTGTAATTGGCAACGATT
ACGCACTTGCAGCTTAATTAAGCAGCACGATCAACCTTGTGGTGGTTCCG
CACTTGGATTGATCGTCATTTAGGGACCTCGGCGTGTTGGGTTTTCTCCA
GCAGACATGCTTAAATTTACTGGGGGAGAGGTCTTAGGGATTTTGTCTGT
GGAAGCCCGAGGACCAATCTAAAACACTGACTAAGTATGTAGCGCCTTAT
CGTGGATCATTTGCGGACGGGGGTTCGATTCCCGCCGCCTCCACCA

TABLE 46 tmDNA Sequence for *Myxococcus xanthus* (delta proteobacterie)

(SEQ ID NO:54)
GGGGGCGGAAAGGATTCGACGGGGGCATTGAAGTTCGAGACGCGTGCCGA
GCTTGTCAGGTAGCTCGTAAATTCAACCCGGCAAAGACACAAAAGCCAAC
GACAACGTTGAGCTCGCGCTGGCTGCCTAAAAACAGCCCATAGTGCGCGG
TCCCCCCGCCCTCGGCCTGTGGGGTTGGGACAGACCGTCATAATGCAGGC
TGGCTGCCGAGGGTGCCTGGACCCGAGGTGGCGAGATCTTCCCAGGACCG
GCTCTGAGTATCCCGTCCGTGGGAGCCTCAGGGACGTAGCAAATCGCGGA
CTACGCACGTAGGGTCGAAGAGCGGACGGCTTTCGGACGCGGGTTCGATT
CCCGCCGCCTCCACCA

TABLE 47 tmDNA Sequence for *Sulfurospirillum Deleylanum*

(SEQ ID NO:55)
GGGGCTGATTCTGGATTCGACAGGAGTAGTTTTAGCTTATGGCTGCATGT
CGGGAGTGAGGGTCTTCCGTTACACAACCTTCAAACAATAACTGCTAACA
ACAGTAACTATCGTCCTGCTTACGCGCTAGCTGCGTAAGTTTAACAAATA

TABLE 47-continued tmDNA Sequence for *Sulfurospirillum Deleylanum*

ATGGACTGCTCTCCCCTTTGATGCTATCTTAGGAGGTCTTGGAGAGTATC
ATAGATTTGATAGCTATATTACATGAACGCCTTTACATGTAATGAAGTTA
AAGGCTCGTTTTGCGTAGTTTTCTGATTGTTGTACGAAGCAAAATTAAAC
ACTATCAACAATATCTAAGCATGTAGACGTCATAGGTGGCTATTTTTGGA
CTGCGGGTTCAACTCCCGCCAGCTCCACCA

TABLE 48 tmDNA Sequence for *Chromatium vinosum*

(SEQ ID NO:56)
GGGGCTGATTCTGGATTCGACGTGGGTCGCGAAACCTAAGGTGCATGCCG
AGGTGCGGTTGACCTCGTAAAACCCTCCGCAAACTTATAGTTGCCAACGA
CGACAACTACGCTCTCGCTGCTTAATCCCAGCGGGCCTCTGACCGTCACT
TGCCTGTGGGCGGCGGATTCCAGGGGTAACCTCACACAGGATCGTGGTGA
CGGGAGTCCGGACCTGATCCACTAAAACCTAACGGAATCGCCGACTGATC
GCCCTGCCCTTCGGGCGGCAGAAGGCTAAAAACAATAGAGTGGGCTAAGC
ATGTAGGACCGAGGGCAGAGGGCTTGCGGACGCGGGTTCAACTCCCGCCA
GCTCCACCA

TABLE 49 tmDNA Sequence for *Pseudomonas fluorescens* (gamma proteobacteria)

(SEQ ID NO:57)
GGGGCTGATTCTGGATTCGACGCCGGTTGCGAACCTTTAGGTGCATGCCG
AGTTGGTAACAGAACTCGTAAATCCACTGTTGCAACTTTCTATAGTTGCC
AATGACGAAACCTACGGGGAATACGCTCTCGCTGCGTAAGCAGCCTTAGC
CCTTCCCTCCTGGTACCTTCGGGTCCAGCAATCATCAGGGGATGTCTGTA
AACCCAAAGTGATTGTCATATAGAACAGAATCGCCGTGCAGTACGTTGTG
GACGAAGCGGCTAAAACTTACACAACTCGCCCAAAGCACCCTGCCCGTCG
GGTCGCTGAGGGTTAACTTAATAGACACGGCTACGCATGTAGTACCGACA
GCAGAGTACTGGCGGACGCGGGTTCAACTCCCGCCAGCTCCACCA

TABLE 50 tmDNA Sequence for *Borrelia afzeli*

(SEQ ID NO:58)
GGGGCTGATTCTGGATTCGACTGAAAATGCTAATATTGTAAGTTGCAAGC
AGAGGGAATCTCTTAAAACTTCTAAAATAAATGCAAAAAATAATAACTTT
ACAAGTTCAAACCTTGTAATGGCTGCTTAAGTTAGCAGAGAGTTTTGTTG
AATTTGGCTTTGAGATTCACTTATACTCTTTTAGACATCGAAGCTTGCTT
AAAAATGTTTTCAAGTTGATTTTTAGGGACTTTTATACTTGAGAGCAATT
TGGCGGTTTGCTAGTATTTCCAAACCATATTGCTTAGTAAAATACTAGAT

TABLE 50-continued tmDNA Sequence for *Borrelia afzeli*

AAGCTTGTAGAAGCTTATAGTATTGTTTTTAGGACGCGGGTTCAACTCCC

GCCAGTCCACCA

TABLE 51 tmDNA Sequence for *Borrelia crociduarae*

(SEQ ID NO:59)
GGGGCTGATTCTGGATTCGACTAAGAACTTTAGTAGCATAAATGGCAAGC

AGAGTGAATCTCTTAAAACTTCTTTAATAAATGCAAAAAATAATAACTTT

ACAAGTTCAGATCTTGTAATGGCTGCTTAATTTAGCAGAGAGTTTTGTTG

GATTTTGCTTTGAGGTTCAACTTATACTCTTTAAGACATCAAAGTATGCC

TAAAAATGTTTCAAGTTGATTTTTAGGGACCTTTAAACTTGAGAGTAATT

TGGTGGTTTGCTTGTTTTCCAAGCCTTATTGCTTTTTCTAAAAATTAGCT

AAGCTTGTAGATATTTATGATATTATTTTTAGGACGCGGGTTCAACTCCC

GCCAGTTCCACCA

TABLE 52 tmDNA Sequence for *Borrelia hermsii*

(SEQ ID NO:60)
GGGGCTGATTCTGGATTCGACTAAAAACTTTAGTAGCATAAATTGCAAGC

AGAGGGAATCTCTTAAAACTTCTTTAATAAATGCAAGAAATAATAACTTT

ACAAGTTCAAATCTTGTAATGGCTGCTTAAATTAGCAGAGAGTTCTGCTG

GATTTTGCTTTGAGGTTCAGCTTATACTCTTTTAAGACATCAAAGCTTGC

TTAAAAATATTTCAAGTTGATTTTTAGGGACTTTTAAATTTGAGAGTAAT

TTGGCGGTTTGCTAGTTTTTCCAAACCTTATTACTTAAAGAAAACACTAG

CTAAGCTTGTAGATATTTATGATATTATTTTTAGGACGCGGGTTCAACTC

CCGCCAGCTCCACCA

TABLE 53 tmDNA Sequence for *Borrelia garinii*

(SEQ ID NO:61)
GGGGCTGATTCTGGATTCGACTGAAAATGCGAATATTGTAAGTTGCAGGC

AGAGGGAATCTCTTAAAACTTCTAAAATAAATGCAAAAAATAATAACTTT

ACAAGCTCAAACCTTGTAATGGCTGCTTAAGTTAGCAGGGAGTTTCGTTG

AATTTGGCTTTGAGGTTCACTTATACTCTTTTCGATATCGAAGCTTGCTT

AAAAATGTTTTCAAGTTAATTTTTAGGGACTTTTGTACTTGAGAGCAATT

TGGCGGTTTGCTAGTATTTCCAAACCATATTGCTTAAGTAAAATGCTAGA

TAAGCTTGTAGAAGCTTATAATATTGTTTTTAGGACGCGGGTTCAACTCC

CGCCAGTCCACCA

TABLE 54 tmDNA Sequence for *Thermodesulfobacterium commune*
(70 degrees)

(SEQ ID NO:62)
GGGGGCGGAAAGGATTCGACGGGGATAGGTAGGATTAAACAGCAGGCCGT

GGTCGCACCCAACCACGTTAAATAGGGTGCAAAAACACAACTGCCAACGA

ATACGCCTACGCTTTGGCAGCCTAAGCGTGCTGCCACGCACCTTTAGACC

TTGCCTGTGGGTCTAAAGGTGTGTGACCTAACAGGCTTTGGGAGGCTTAA

TCGGTGGGGTTAAGCCTCCCGAGATTACATCCCACCTGGTAGGGTTGCTT

GGTGCCTGTGACAAGCACCCTACGAGATTTTCCCACAGGCTAAGCCTGTA

GCGGTTTAATCTGAACTATCTCCGGACGCGGGTTCGATTCCCGCCGCCTC

CCCACCA

TABLE 55 tmDNA Sequence for *Thermotoga neapolitana*
(Thermotogales)

(SEQ ID NO:63)
GGGGGCGGAAAGGATTCGACGGGGATGGAGTCCCCTGGGAAGCGAGCCGA

GGTCCCCACCTCCTCGTAAAAAAGGTGGGAACACGAATAAGTGCCAACGA

ACCTGTTGCTGTTGCCGCCTAATAGATAGGCGGCCGTCCTCTCCGGAGTT

GGCTGGGCTCCGGAAGAGGGCGTGAGGGATCCAGCCTACCGATCTGGGCT

CCGCCTTCCGGCCCGGATCGGGAAGGTTCAGGAAGGCTGTGGGAAGCGAC

ACCCTGCCCGTGGGGGGTCCTTCCCGAGACACGAAACACGGGCTGCGCTC

GGAGAAGCCCAGGGGCCTCCATCTTCNGACGCGGGTTCGATTCCCGCCAC

CTCCACCA

TABLE 56 tmDNA Sequence for *Deinococcus proteolyticus*

(SEQ ID NO:64)
GGGGGCGGAAAGGATTCGACGGGGGAACGGAAAGCGCTGCTGCGTGCCGA

GGAGCCGTTGGCCTCGTAAACAAACGGCAAAGCCATTAACTGGCGAAAAT

AACTACGCTCTCGCTGCTTAAGTGAGACAGTGACCACGTAGCCCCGCCTT

TGGCGACGTGTGAACTGAGACAAAAGAAGGCTAGCTTAGGTGAGGTTCCA

TAGCCAAAAGTGAAACCAAATGGAAATAAGGCGGACGGCAGCCTGTTTGC

TGGCAGCCCAGGCCCGACAATTTAAGAGCAGACTACGCACGTAGATGCAC

GCTGGATGGACCTTTGGACGCGGGTTCGATTCCCGCCAGCTCCACCA

TABLE 57 tmDNA Sequence for *Prosthecobacter fusformis*
(verrucomicrobia)

(SEQ ID NO:65)
GGGGCTGATTCTGGATTCGACGGGGAGTACAAGGATCAAAAGCTGCAAGC

CGAAGGTGCCGTTACCTCGTAAAACAACGGCAAAAAAGAAGTGCCAACACA

AATTTAGCATTAGCTGCTTAATTTAGCAGCTACGCTCTTCTAACCCGGGC

TABLE 57-continued tmDNA Sequence for *Prosthecobacter fusformis* (*verrucomicrobia*)

TGGCAGGGTTAGAAGGGTGTCATAATGAGCCAGCTGCCCCTTCCGACTCC

CCTAAGGAAGGGAAAGATGTAGGGGATAGGTGCTTACAGAATCCTGCGGG

AGGGAGTCTGTAAGTGCCGAAAAGTTAAAACTCCCGCTAAGCTTGTAGAG

GCTTTTGATTCTTGCTCTCTGGACGCGGGTTCAACTCCCGCCAGCTCCAC

CA

TABLE 58 tmDNA Sequence for *Verrucomicrobium spinosum* (*verrucomicrobium*)

(SEQ ID NO:66)
GGGNNNNATTTGGAATTCGCCGAATGCTAGAAGTGGAGGCTGCATGCCGC

GGATGATTCGTTGGCCGCTTTACCAATTCGGATCAAACAACTAAATGCGG

ACTCTAACGAGCTTGCCCTCGCCGCTTAATTGACGGTGACGTTCCTCCAG

TGAAGTCTGTGAATTGGAGGAGCGACTACTTACAGGCTGGCCAAAAGAGC

GGGCGACCGGCCCCAAGGCGAGATCTACAGGCCGCTGGATGGACGGCATC

CTGGCAGTAGGAGGCTGGACATCGAGATCAAATNATTGCCTGAGCATGGA

GACGCTTTCATAAAGGNGTTCGGACAGGG

Example 4

Alignment of tmRNA Sequences

The newly discovered tmRNA sequences and several known tmRNA sequences were aligned to identify target sites for drug development. The alignments of the sequences are shown in FIGS. 3A-11B. The nucleotides in the tmRNA sequences of these figures exist in several motifs (Felden et al., 1999). These motifs include nucleotides considered to be in RNA helices (Watson-Crick base-pairs GC or AU, or GU Wobble base-pairs). Nucleotides that are in single stranded RNA domains, hence not base-paired. Some nucleotides in the single stranded domains are universally conserved nucleotides. Other nucleotides are the exceptions to a quasi-sequence conservation in the sequences alignment. Several nucleotides exist in well established non-canonical structural motifs in RNA structures; for example AG-GA pairs, AA pairs, etc. Some nucleotides are universally conserved Wobble GU base-pairs.

All the gene sequences have been decomposed in several structural domains that have been indicated with names at the top of each block of sequences. These domains are respectively from the 5'-end to the 3'-end of the sequences: H1, H5, H2, PK1, H4, PK2, PK3, PK4, H5 and H6. The bars delineate all the structural domains. H means helices and PK means pseudoknot. A pseudoknot is made of the pairing of parts of an RNA-loop with an upstream sequence. Consequently, two helices are made (shown in Felden et al., 1999) for all the 4 pseudoknots PK1 to PK4 for each sequence. Moreover, the tRNA-like domain as well as the coding sequence, namely the two functional units of the molecule, have also been indicated for each sequence.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria.

Common Structural Features for Drug Targeting:

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. The PK1 structural domain is strictly conserved in the tmRNAs and is located upstream of the coding sequence. Since these pseudoknots are not found in all canonial transfer RNAs, they can also be targeted with specific drugs. Disruption of either PK1 or PK2 or PK3 with a specific drug would lead to inactive tmRNA molecules in vivo.

Specific Structural Features in Each Phylum that could be Targeted by Drugs:

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding, which has been shown for *Escherichia coli*, and thus, is also available for interaction with other drugs. Moreover, this is a critical functional domain of the molecule in its quality-control mechanism in cells. In addition, this coding sequence would be the ideal target to use for designing specific PCR-based diagnostic assays for infection diseases.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 base-pairs instead of 5 in the other species;

(3) for two sequences of chlorobium as well as *Bacteroides* thetaiotaomicron and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future antibacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Andersson, S. G. et al. (1998). *Nature* 396:133-140.
Ando, H. et al. (1996). *Genes & Genet. Syst.* 71:47-50.
Breithaupt, H. (1999). *Nature Biotechnol.* 17:1165-1169.
Felden, B. et al. (1996). *Biochimie* 78:979-983.
Felden, B. et al. (1997). *RNA* 3:89-103.
Felden, B. et al. (1998). *EMBO J.* 17:3188-3196.
Felden et al. (1999). *Biochim. Biophys. Acta* 1446:145-148.
Gray, M. W. and Spencer, D. F. (1996). In *Evolution of Microbial Life*, Cambridge University Press, pp. 109-126.
Hickerson, R. P. et al. (1998). *J. Mol. Biol.* 279:577-587.
Himeno, H. et al. (1997). *J. Mol. Biol.* 268:803-808.
Huang, C. et al. (2000). *EMBO J.* 19:1098-1107.
Julio, S. M et al. (2000). *J. Bacteriol.* 182:1558-1563.
Keiler, K. C. et al. (1996). *Science* 271:990-993.
Komine, Y. et al. (1994). *Proc. Natl. Acad. Sci. USA* 20:9223-9227.
Mateeva, O. et al. (1997). *Nucleic Acids Res.* 25:5010-5016.
Muto, A. et al. (1998). *Trends Biochem. Sci.* 1:25-29.
Nameki, N. et al. (1999). *J. Mol. Biol.* 286:733-744.
Nakemi, N. et al. (2000). *FEBS Lett.* 470:345-349. *Remington's Pharmaceutical Sciences,* 18th Ed., Mack Publishing Co., Easton, Pa., 1990.
Tu, G. F. et al. (1995). *J. Biol. Chem.* 270:9322-9326.
Ushida, C. et al. (1994). *Nucleic Acids Res.* 16:3392-3396.
Williams, K. P. (1999). *Nucleic Acids Res.* 27:165-166.
Williams, K. P. and Bartel, D. P. (1996). *RNA* 2:1306-1310.
Wower, J. and Zwieb, C. (1999). *Nucleic Acids Res.* 27:167.
Yang, D. et al. (1985). *Proc. Natl. Acad. Sci. USA* 82:4443-4447.

What is claimed is:

1. An isolated nucleic acid sequence selected from the group consisting of the tmRNA sequence for *Mycobacterium tuberculosis* set forth in SEQ ID NO: 134, a tmDNA sequence encoding said tmRNA sequence, and a full-length complement of said tmDNA sequence.

2. A method for diagnosing a bacterial infection associated with *Mycobacterium tuberculosis* comprising determining the presence of a bacterial nucleic acid sequence selected from the group consisting of the tmRNA sequence for *Mycobacterium tuberculosis* set forth in SEQ ID NO: 134, a tmDNA sequence encoding said tmRNA sequence, and a full-length complement of said tmDNA sequence.

3. The method of claim 2, wherein the determination is made by performing an amplification-based assay.

4. The isolated nucleic acid sequence of claim 1, wherein the nucleic acid sequence is the tmDNA sequence encoding the tmRNA sequence for *Mycobacterium tuberculosis* set forth in SEQ ID NO:134.

5. The method of claim 2, wherein the bacterial nucleic acid sequence is the tmDNA sequence encoding the tmRNA sequence for *Mycobacterium tuberculosis* set forth in SEQ ID NO:134.

6. The method of claim 3, wherein the bacterial nucleic acid sequence is the tmDNA sequence encoding the tmRNA sequence for *Mycobacterium tuberculosis* set forth in SEQ ID NO:134.

* * * * *